US011946047B2

(12) United States Patent
Zeng et al.

(10) Patent No.: US 11,946,047 B2
(45) Date of Patent: Apr. 2, 2024

(54) TREATMENT STRATEGIES AGAINST ANTHRAX BY INTERFERING WITH CRITICAL HOST FACTORS

(71) Applicant: Texas Tech University System, Lubbock, TX (US)

(72) Inventors: Mingtao Zeng, El Paso, TX (US); Lihong Wu, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 16/660,986

(22) Filed: Oct. 23, 2019

(65) Prior Publication Data

US 2020/0123545 A1 Apr. 23, 2020

Related U.S. Application Data

(60) Provisional application No. 62/749,216, filed on Oct. 23, 2018.

(51) Int. Cl.
*C12N 15/113* (2010.01)

(52) U.S. Cl.
CPC ........ *C12N 15/113* (2013.01); *C12N 2310/14* (2013.01); *C12N 2320/32* (2013.01)

(58) Field of Classification Search
CPC .............. C12N 15/113; C12N 2320/32; C12N 2310/14
See application file for complete search history.

(56) References Cited

U.S. PATENT DOCUMENTS

2006/0128650 A1* 6/2006 Xu .......................... A61P 25/16
514/44 A
2014/0068797 A1* 3/2014 Doudna ................... C12N 9/22
800/18

FOREIGN PATENT DOCUMENTS

WO WO-2017145165 A1 * 8/2017 .............. A61P 35/04
WO WO-2018112033 A1 * 6/2018

OTHER PUBLICATIONS

Farah et al (Journal of Hepatology 64: 370-379, 2016) (Year: 2016).*
Farah et al (Journal of Hepatology 64: Supplementary Material, 26 pages, 2016) (Year: 2016).*
Wang et al (PLoS ONE 9(11): e112150, 7 pages) (Year: 2014).*
Wu et al (Front. Immunol. 9:211, Feb. 2018) (Year: 2018).*
Arevalo, M.T. et al. "Targeted silencing of anthrax toxin receptors protects against anthrax toxins." The Journal of biological chemistry 289, (2014) 15730-15738.
Arsand, E. et al. "Using blood glucose data as an indicator for epidemic disease outbreaks."Studies in health technology and informatics 116, (2005) 217-222.
Bhattacharya, K. "Investigation and management of the hepatic glycogen storage diseases." Translational pediatrics 4, (2015) 240-248.
Bouschet, T. et al. "Receptor-activity-modifying proteins are required for forward trafficking of the calcium-sensing receptor to the plasma membrane." Journal of cell science 118, (2005) 4709-4720.
Croft, W. et al. (2013) "A physiologically required G protein-coupled receptor (GPCR)-regulator of G protein signaling (RGS) interaction that compartmentalizes RGS activity." The Journal of biological chemistry 288, (2013) 27327-27342.
Dal Molin, F. et al. "cAMP imaging of cells treated with pertussis toxin, cholera toxin, and anthrax edema toxin." Biochemical and biophysical research communications 376, (2008) 429-433.
De Vries, L. et al. "The regulator of G protein signaling family." Annual review of pharmacology and toxicology 40, (2000) 235-271.
Denecke, B. et al. "RGS1 is expressed in monocytes and acts as a GTPase-activating protein for G-protein-coupled chemoattractant receptors." The Journal of biological chemistry 274, (1999) 26860-26868.
Dostalova, G. et al. "Multiple thrombophilia mutations as a possible cause of premature myocardial infarction." Wiener klinische Wochenschrift 129, (2017) 503-508.
Edwards, M. et al. "Isolation of mouse hepatocytes." Methods Mol Biol 987, (2013) 283-293.
Faybik, P. et al. "Plasma disappearance rate of indocyanine green in liver dysfunction." Transplantation proceedings 38, (2006) 801-802.
Firoved, A.M. et al. "Bacillus anthracis edema toxin causes extensive tissue lesions and rapid lethality in mice." The American journal of pathology 167, (2005) 1309-1320.
Flevaris, P. et al. "The Role of Plasminogen Activator Inhibitor Type-1 in Fibrosis." Seminars in thrombosis and hemostasis 43, (2017) 169-177.
Gille, A. et al. "Differential inhibition of adenylyl cyclase isoforms and soluble guanylyl cyclase by purine and pyrimidine nucleotides." The Journal of biological chemistry 279, (2004) 19955-19969.
Grundmann, O. "The current state of bioterrorist attack surveillance and preparedness in the US." Risk management and healthcare policy 7, (2014) 177-187.
Han, J.I. et al. "RGS1 and RGS13 mRNA silencing in a human B lymphoma line enhances responsiveness to chemoattractants and impairs desensitization." Journal of leukocyte biology 79, (2006) 1357-1368.
Heiman, M. et al. "Complete Plasminogen Activator Inhibitor 1 Deficiency." In eneReviews(R), R.A. Pagon, M.P. Adam, H.H. Ardinger, S.E. Wallace, A. Amemiya, L.J.H. Bean, T.D. Bird, N. Ledbetter, H.C. Mefford, R.J.H. Smith, et al., eds. (Seattle (WA) (1993)).
Henderson, D.A. "John Bartlett and bioterrorism." Clinical infectious diseases: an official publication of the Infectious Diseases Society of America 59 Suppl 2, (2014) S76-79.

(Continued)

*Primary Examiner* — Richard A Schnizer
(74) *Attorney, Agent, or Firm* — Edwin S. Flores; Daniel J. Chalker; Chalker Flores, LLP

(57) ABSTRACT

The present invention includes a composition and method for decreasing *Bacillus anthracis* virulence or toxicity comprising: at least one inhibitor that decreases an expression of one or more host genes selected from G6pc, Rgs1, Fosl2, Hcar2, Cxcl2 and Cxcl3, or Serpine1 (PAI-1).

9 Claims, 19 Drawing Sheets

Specification includes a Sequence Listing.

(56) References Cited

OTHER PUBLICATIONS

Hepler, J.R. "Emerging roles for RGS proteins in cell signaling." Trends in pharmacological sciences 20, (1999) 376-382.

Houseman, L. et al. Isolation and Culture of Mouse Hepatocytes: Gender-Specific Gene Expression Responses to Chemical Treatments. Methods Mol Biol 1250, (2015) 3-12.

Jaswal, D.S. et al. "Bacillus anthracis Edema Toxin Increases Fractional Free Water and Sodium Reabsorption in an Isolated Perfused Rat Kidney Model." Infect Immun 85 (2017).

Liu, S. et al. "Anthrax lethal and edema toxins in anthrax pathogenesis." Trends in microbiology 22, (2014) 317-325.

Liu, S. et al. "Key tissue targets responsible for anthrax-toxin-induced lethality." Nature 501, (2013) 63-68.

Lubker, C. et al. "Different Roles of N-Terminal and C-Terminal Domains in Calmodulin for Activation of Bacillus anthracis Edema Factor." Toxins 7, (2015)2598-2614.

Lugli, E. et al. "Characterization of cells with different mitochondrial membrane potential during apoptosis." Cytometry Part A: the journal of the International Society for Analytical Cytology 68, (2005) 28-35.

Mithieux, G. et al. "A novel role for glucose 6-phosphatase in the small intestine in the control of glucose homeostasis." The Journal of biological chemistry 279, (2004) 44231-44234.

Mutel, E. et al. Control of blood glucose in the absence of hepatic glucose production during prolonged fasting in mice: Induction of renal and intestinal gluconeogenesis by glucagon. Diabetes 60, (2011) 3121-3131.

Oh, K.J. et al. "CREB and FoxO1: two transcription factors for the regulation of hepatic gluconeogenesis." BMB reports 46, (2013) 567-574.

Patel, K. et al. "The LKB1-salt-inducible kinase pathway functions as a key gluconeogenic suppressor in the liver." Nature communications 5, (2014) 4535.

Poole, L.G. et al. "Plasminogen Activator Inhibitor-1 is Critical in Alcohol-enhanced Acute Lung Injury in Mice." American journal of respiratory cell and molecular biology. (2017).

Sastalla, I. "Anthrax edema toxin impairs clearance in mice." Infect Immun 80, (2012) 529-538.

Serezani, C.H. et al. "Cyclic AMP: master regulator of innate immune cell function." American journal of respiratory cell and molecular biology 39, (2008) 127-132.

Vaghjiani, V. et al. "Hepatocyte-like cells derived from human amniotic epithelial cells can be encapsulated without loss of viability or function in vitro." Stem cells and development 23, (2014) 866-876.

Welkos, S.L. et al. "Differences in susceptibility of inbred mice to Bacillus anthracis." Infect Immun 51, (1986)795-800.

Duenas-Carrera, Santiago et al. "A truncated variant of the hepatitis C virus core induces a slow but potent immune response in mice following DNA immunization" Vaccine 19 (2001) 992-997.

Ma, Yunzhe et al. "Vaccine delivery to oral cavity using coated microneedles induces systemic and mucosal immunity" Pharm Zres. Sep. 2014; 31(9): 2393-2403.

Pattenden, Leonard K. et al. "Towards the preparative and large-scale precision manufacture of virus-like particles" Trends in Biotechnology vol. 23 No. Oct. 10, 2005 523-529.

McCaskill, A.C. et al. "Anaphylaxis following intranasal challenge of mice sensitized with ovalbumin" Immunology 1984 51 669-677.

Toebak, Mascha J. et al. "Dendritic cells: biology of the skin" Contact Dermatitis 2009: 60: 2-20.

* cited by examiner

TREATMENT STRATEGIES AGAINST ANTHRAX BY INTERFERING WITH CRITICAL HOST FACTORS

CROSS-REFERENCE TO RELATED APPLICATIONS

This application claims priority to U.S. Provisional Application Ser. No. 62/749,216, filed Oct. 23, 2018, the entire contents of which are incorporated herein by reference.

STATEMENT OF FEDERALLY FUNDED RESEARCH

This invention was made with government support under R21AI118228 awarded by the National Institutes of Health/National Institute of Allergy and Infectious Diseases. The government has certain rights in the invention.

TECHNICAL FIELD OF THE INVENTION

The present invention relates in general to the field of treatment strategies against anthrax by interfering with critical host factors.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Oct. 22, 2019, is named TECH1194_SeqList.txt and is 45, kilo bytes in size.

BACKGROUND OF THE INVENTION

Without limiting the scope of the invention, its background is described in connection with *Bacillus anthracis* infections and toxicity.

Anthrax is a serious infectious disease caused by the gram-positive, rod-shaped bacterium *Bacillus anthracis* (Grundmann, 2014), which is considered a potential biological warfare agent and poses a serious threat to human life (Henderson, 2014; Sugden and Katchmar, 2005). Although some antibiotics can be used to treat patients with anthrax by killing these bacteria, the outcomes remain poor, because what sickens and kills are not the bacteria themselves but the toxins they produce. Therefore, new therapeutic targets against anthrax toxins are urgently required.

*Bacillus anthracis* gains virulence through its three-component protein exotoxin, which is composed of protective antigen (PA), edema factor (EF), and lethal factor (LF). EF and LF are individually nontoxic but are toxic in combination with PA to form two A/B toxins, edema toxin (EdTx, EF+PA) and lethal toxin (LeTx, LF+PA), causing different pathogenic responses in cultured cells and animals. In these two toxins, the A components, EF and LF, have enzymatic activities. EF (in EdTx) is a calmodulin-dependent adenylate cyclase that increases intracellular cAMP concentrations, leading to subcutaneous edema and fluid accumulation in organs (Liu et al., 2014), while LF (in LeTx) is a zinc-dependent metalloprotease specifically cleaving the N-terminus of most mitogen-activated protein kinase kinases (e.g., MAPKK or MEK), resulting in disruptions of the signaling cascades essential for cell proliferation, cell cycle regulation, and immune function. The B component, PA, binds to cell surface anthrax toxin receptors, including tumor endothelium marker 8 (TEM8) and capillary morphogenesis protein 2 (CMG2) (Arevalo et al., 2014). Therefore, anthrax toxins are likely to have a wide range of toxic effects caused by the increase in intracellular cAMP and/or cleavage of MEK2. Although the signaling pathways involved in anthrax toxin-induced organ damage have been extensively investigated, the underlying mechanisms and downstream targets are poorly understood.

Liu et al. reported that anthrax toxins selectively induce damage in distinct cell types. They found that EdTx mainly targets the liver and induces a unique liver edema that does not occur in other internal organs, while LeTx targets cardiomyocytes and vascular smooth muscle cells, leading to LeTx-induced mortality (Liu et al., 2013).

Despite these observations and some understanding of the various targets for anthrax toxins, a need remains for improved compositions and methods for treating anthrax infections and exposure to anthrax toxins.

SUMMARY OF THE INVENTION

In one embodiment, the present invention includes a composition for decreasing *Bacillus anthracis* virulence or toxicity comprising: at least one inhibitor that decreases an expression of one or more host genes selected from G6pc, Rgs1, Fosl2, Hcar2, Cxcl2 and Cxcl3, or Serpine1 (PAI-1), wherein the composition decreases the virulence or toxicity of *Bacillus anthracis*. In one aspect, the inhibitor is an RNA molecule active for gene silencing through RNA interference (RNAi) or a small molecule inhibitor of the proteins. In another aspect, the composition further comprises a pharmaceutically acceptable carrier. In another aspect, the carrier is a lipid molecule or liposome. In another aspect, the inhibitor comprises a polynucleotide sense strand and a polynucleotide antisense strand that are connected as a single strand, and form a duplex region connected at one end by a loop. In another aspect, wherein at least one polynucleotide in any strand is at least chemically modified at one base. In another aspect, the inhibitor targets disruption or knockdown of the G6pc, Rgs1, Fosl2, Hcar2, Cxcl2 and Cxcl3, or Serpine1 (PAI-1) gene in a living cell. In another aspect, the composition further comprises a delivery system or expression system for antisense oligonucleotide, ribozyme or an inhibitory RNA. In another aspect, the inhibitory RNA is selected from the group consisting of an siRNA, shRNA, a bishRNA, and miRNA. In another aspect, the virulence is cardiotoxicity or hepatotoxicity. In another aspect, the inhibitors are polynucleotides selected from SEQ ID NOS: 1-58.

In another embodiment, the present invention includes a method of decreasing the virulence or toxicity of *Bacillus anthracis* comprising: identifying a subject in need of treatment for an infection with or exposure to one or more *Bacillus anthracis* spores, vegetative cells, toxins; and providing the subject with an effective amount of an inhibitor of an expression of one or more host genes selected from G6pc, Rgs1, Fosl2, Hcar2, Cxcl2 and Cxcl3, or Serpine1 (PAI-1) sufficient to decrease *Bacillus anthracis* virulence or toxicity. In one aspect, the inhibitor is an RNA molecule active for gene silencing through RNA interference (RNAi) or a small molecule inhibitor of the proteins. In another aspect, the composition further comprises a pharmaceutically acceptable carrier. In another aspect, the carrier is a lipid molecule or liposome. In another aspect, the inhibitor comprises a polynucleotide sense strand and a polynucleotide antisense strand that are connected as a single strand, and form a duplex region connected at one end by a loop. In another aspect, wherein at least one polynucleotide in any strand is at least chemically modified at one base. In another aspect, the inhibitor targets disruption or knockdown of the G6pc, Rgs1, Fosl2, Hcar2, Cxcl2 and Cxcl3, or Serpine1 (PAI-1) gene in a living cell. In another aspect, the composition further comprises a delivery system or expression system for antisense oligonucleotide, ribozyme or an inhibitory RNA. In another aspect, the inhibitory RNA is selected from the group consisting of an siRNA, shRNA, a bishRNA, and miRNA. In another aspect, the virulence is cardiotoxicity or hepatotoxicity. In another aspect, the inhibitors are polynucleotides selected from SEQ ID NOS: 1-58.

BRIEF DESCRIPTION OF THE DRAWINGS

For a more complete understanding of the features and advantages of the present invention, reference is now made to the detailed description of the invention along with the accompanying figures and in which:

(FIG. 1A) Animal experiment flow chart. (FIG. 1B) Survival curves (n=10). (FIG. 1C) The levels of cAMP in serum (left) and liver tissue (right) at different time points after EdTx (20 μg) challenge (n=15). (FIG. 1D) Blood glucose level at different time points after EdTx (20 μg) challenge. (FIG. 1E) H&E (top) and PAS (bottom) staining of liver tissues at 18 h after EdTx (20 μg) challenge. Scale bar, 30 μm. Red arrows indicate glycogen in the liver. The red star indicates hepatocellular necrosis in the liver. n=3. (FIG. 1F) Glycogen concentration in liver at 18 h after EdTx (20 μg) challenge. *P<0.05, **P<0.01 vs. PBS-treated control mice; n=3. FIG. 1G. The mRNA expression of anthrax toxin receptors in primary hepatocytes and cardiomyocytes, liver and heart tissues of mice. The mRNA expression of Tem8 (584 bp), Cmg2 (364 bp), and Gapdh (239 bp) was detected in liver tissues, primary hepatocytes (left panel), heart tissues, and primary cardiomyocytes (right panel) on an agarose gel. FIG. 1H. Cell viability of primary cardiomyocytes treated with a single dose of LeTx. The MTT assay was performed after primary cardiomyocytes were treated with PBS or LeTx (2 μg/ml) for 12 h (left) and 18 h (right). Representative results from three independent experiments are shown. Data are normalized to cell viability of PBS-treated control cells and expressed as mean±standard deviation; n=8.

(FIG. 2A) Flow cytometry analysis was performed to measure the expression of the anthrax toxin receptors TEM8 and CMG2 in primary hepatocytes. Representative plots (left panel) are shown for cell samples that were unstained, stained for TEM8 alone, for CMG2 alone, or dual-stained for TEM8 and CMG2. The results were quantified (right panel). (FIG. 2B) Primary hepatocytes were treated with 0.25, 0.5, 1, 2, or 4 μg/mL EdTx and then lysed with 0.5 mL of 0.1 M HCl at 0, 0.25, 0.5, 1, 2, 4, 6, 8, 16, or 24 h, with PBS used as a negative control. Cell lysates were diluted 8 fold for testing. The level of intracellular cAMP was measured using a commercial ELISA kit. Representative results from three independent experiments are shown. Data are expressed as mean±standard deviation. P<0.01 vs. control. (FIG. 2C) Primary hepatocytes were treated with PBS or EdTx (4 μg/ml) for 6 h, and cells were visualized using phase-contrast microscopy. Scale bar, 100 μm. (FIG. 2D) An MTT assay was performed after primary hepatocytes were treated with PBS or EdTx (4 μg/ml) for 6 h. Representative results from three independent experiments are shown. Data are normalized to the cell viability of PBS-treated control cells and expressed as mean±standard deviation. P<0.01 vs. control; n=8. (FIG. 2E) Mitochondrial membrane potential analysis using 5,5',6,6'-tetrachloro-1,1',3,3'-tetraethyl benzimidaloyl carbocyanine iodide (JC-1) mitochondrial membrane dye. Cells were treated with PBS or EdTx (4 μg/ml) for 6 h and then incubated with 10 μg/ml JC-1 in a $CO_2$ incubator at 37° C. for 30 min. Normal cells appear red with the J-aggregated stain, and apoptotic cells appear green with the J-monomer stain. Scale bar, 100 μm. (FIG. 2F) Indocyanine green (ICG) uptake-and-release assay. Cells were treated with PBS or EdTx (4 μg/ml) for 6 h and incubated with ICG in a $CO_2$ incubator at 37° C. for 2 h. Medium was refreshed after 24 h of incubation. Cells with a green-stained nucleus are ICG-positive hepatocytes. Scale bar, 100 μm. (FIG. 2G) PAS staining. Cells were treated with PBS or EdTx (4 μg/ml) for 6 h and stained for glycogen within the cells using the Sigma-Aldrich PAS kit. Scale bar, 100 μm. Red arrows indicate glycogen in the cells. (FIG. 2H) Quantification of (G). Data are expressed as mean±standard deviation. **P<0.01 vs. control; n=3.

FIGS. 3A to 3D show the identification of EdTx-induced, cytotoxicity-related genes. Total RNA was isolated from primary hepatocytes treated with PBS or EdTx (4 μg/mL) for 6 h, and the samples were subjected to microarray analysis using the GeneChips Mouse Transcriptome Assay 1.0. Some genes (218) were found to have significant expression changes in primary hepatocytes exposed to EdTx treatment compared with PBS-treated cells. The Partek Genomic Suite was used to analyze the signaling pathways associated with these differentially expressed genes. The pathways with enrichment score >2 and p-value <0.05 are shown in (FIG. 3A). The numbers at the top of each column show the number of genes that have expression changes in each pathway. In order to verify the microarray results, qPCR analyses were performed for 70 genes selected from these signaling pathways using RNA from the same samples that had been used for the microarray assay as well as RNA from liver tissues of mice receiving the same PBS or EdTx treatment as in the in vitro experiments. The microarray results for 35 genes that were confirmed to have significant expression changes in both primary hepatocytes and liver tissue are shown in (FIG. 3B). The results of a protein-protein network analysis among the 35 genes are shown in (FIG. 3C). Nine genes that are involved in glycogen metabolism, cAMP production, and cell apoptosis are marked with red circles and were further investigated in the following experiments. (FIG. 3D) These potential EdTx-induced cytotoxicity-related genes were knocked down individually or in combination in primary hepatocytes using the corresponding siRNAs. si-CMG2 was used as a positive control, and si-GFP and si-(no gene) were used as negative controls. Primary hepatocytes deficient in these genes were treated with PBS or EdTx (4 μg/mL) for 6 h. The intracellular concentration of cAMP was determined using ELISA. *P<0.05, **P<0.01 vs. si-GFP (n=3). 4 mix, Ramp3+Rgs1+Pck1+G6pc; 5 mix, Hcar2+Fosl2+Fos+Cxcl2+Cxcl3.

FIGS. 4A to 4E show that PAI-1 is associated with the in vivo toxicity of LeTx. (FIG. 4A) Survival curve of wild type (WT) C57BL/6J mice challenged with 0, 8.75, 12.5, 18.75, 25, or 50 μg of LeTx in 0.2 ml of PBS. (FIG. 4B) Western blot assay for cleaved MEK2 and β-actin expression in the heart and liver of WT C57BL/6J mice treated with 50 μg of LeTx for 24 h. (FIG. 4C) The serum levels of PAI-1 in WT Balb/c mice, WT C57BL/6J mice, and PAI-1 knockout (PAI-1$^{-/-}$) C57BL/6J mice treated with 0, 12.5, or 50 µg LeTx were determined by ELISA. **P<0.01 vs. control. (FIG. 4D) Survival curve of WT and PAI-1$^{-/-}$ C57BL/6J mice treated with PBS or 12.5 µg of LeTx. (FIG. 4E) H&E staining of liver sections from WT and PAI-1$^{-/-}$ C57BL/6J mice treated with PBS or 12.5 µg LeTx. Scale bar, 30 µm. Red arrows indicate anisonucleosis in the liver. Scale bar, 100 µm.

(FIG. 5A) Flow cytometry analysis was performed to measure the expression of the anthrax toxin receptors TEM8 and CMG2 in primary cardiomyocytes. Representative plots (left panel) are shown for cell samples that were unstained, stained for TEM8 alone, stained for CMG2 alone, or dual-stained for TEM8 and CMG2, and the results were quantified (right panel). Experiments were independently repeated at least three times. Data are expressed as mean±standard deviation (SD). (FIG. 5B) Two doses of LeTx (2 µg/mL) were administered with an 18-h interval between doses. An MTT assay was performed at 18 h after the second dose of LeTx to examine cell viability. The data are expressed as mean±SD. *P<0.05, P<0.01 vs. PBS-treated control cells; n=8. (FIG. 5C) Western blot assay for cleaved MEK2 and β-actin expression in primary cardiomyocytes and hepatocytes at 0, 6, 12, or 18 h after LeTx (2 µg/mL) treatment. (FIG. 5D) PAS staining assay. Primary cardiomyocytes were treated with PBS or LeTx (2 µg/ml) for 6 h and stained for glycogen within the cells using the Sigma-Aldrich PAS kit. Scale bar, 100 µm. (FIG. 5E) Indocyanine green (ICG) uptake-and-release assay. Primary cardiomyocytes were treated with PBS or LeTx (2 µg/ml) for 6 h and incubated with ICG in a $CO_2$ incubator at 37° C. for 2 h. Medium was refreshed after 18 h of incubation. Cells with green-stained nuclei are ICG-positive cardiomyocytes. Scale bar, 100 µm. (FIG. 5F) Quantification of (D). Data are expressed as mean±SD. P<0.01 vs. control; n=3.

FIG. 6A is a heat map of 18 genes that have significant expression changes (with log ratio >1.8 or log ratio <0.56) in LeTx-treated primary cardiomyocytes. The results of a protein-protein network analysis among these genes using STRING 10 software are shown in (FIG. 6B). Thick lines indicate strong associations. Serpine1 (encoding PAI-1), which is at the center of the network and marked with a red circle, was selected for knockout in subsequent experiments.

DETAILED DESCRIPTION OF THE INVENTION

Figure 1A:
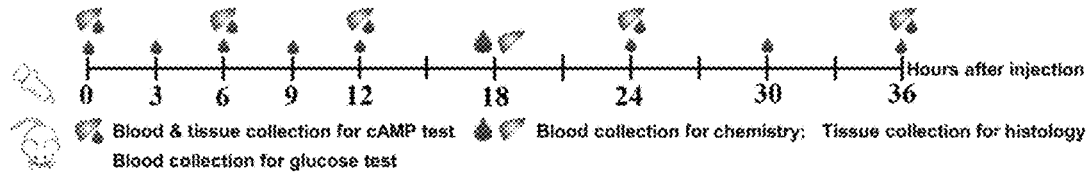
FIGS. 1A to 1H show that EdTx rapidly degrades liver function in A/J mice. A/J mice were intravenously injected with 20 μg EdTx (20 μg EF plus 40 μg PA) or 40 μg EdTx in 0.2 mL PBS, while mice in the control group were injected with PBS only.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

Anthrax and the need for an effective treatment. Anthrax is a disease resulting from infection by spores of the Gram-positive bacterium Bacillus anthracis, a Category A Select Agent as designated by Centers for Disease Control (CDC). The formation of spores protects B. anthracis, allowing it to remain dormant and survive harsh chemical and thermal stresses until the local environment becomes more suitable for growth. The disease manifests itself in three ways, resulting from three separate modes of infection. The most common occurrence of anthrax results from cutaneous exposure, where B. anthracis infects the host through a cut or abrasion on the skin. Secondly, digestive anthrax occurs upon consumption of contaminated food products by gaining entry into the gut. The final, and by far most deadly form of anthrax, is pulmonary or inhalational anthrax. Although there is a licensed anthrax vaccine (BioThrax™) available for public use in the USA, it is not realistic to have a national immunization program in place since anthrax is a naturally rare disease in humans; and the complicated vaccine regimen makes this approach unrealistic anyway. In order to develop a more effective anthrax vaccine, currently, anthrax toxin components, PA and detoxified EF and LF, have been used as the key antigens in the current anthrax vaccine and in next-generation anthrax vaccines. Administration of Bio-Thrax™ in combination with antibiotic may also provide certain benefit for post-exposure prophylaxis. Nevertheless, anthrax remains an imminent threat because it can be intentionally introduced by bioterrorists targeting individuals or the masses. A few antibiotics, such as ciprofloxacin, can be used in killing B. anthracis bacteria. However, antibiotics are effective only prior to the onset of symptoms resulting from anthrax septicemia and toxemia because the toxins remain active long after bacterial death. In addition, antibiotic-resistant B. anthracis strains may be generated by bioterrorists. Clearly, a different strategy to develop a new and effective treatment as proposed in this research is imperative, and targeting toxin entry pathways and downstream cell death pathways may prove a successful approach for prophylactic and post exposure treatment against anthrax. Although not actually evaluated by human challenge study, analysis of human cases of naturally occurred inhalation anthrax has shown that the estimated median time from exposure to onset of symptoms (incubation period) among untreated cases to be 9.9 days (7.7-13.1) for exposure to ID50 of *B. anthracis* spores. With advancement of the earlier and rapid detection technology for *B. anthracis* spore exposure and in the environment as well as intellectually information gathering (such as in biodefense), this incubation period gives us a sufficient time window for administration of our host-targeted siRNA therapeutics with possible high efficacy for treatment.

Anthrax, which is caused by the spore-forming bacterium *Bacillus anthracis*, is one of the major bio-threats to public health. Following exposure of *B. anthracis* spores, macrophages ingest anthrax spores and travel to the lymph node where these spores germinate. The *B. anthracis* bacteria are then released into the bloodstream and produce toxins that are key factors in the virulence of disease: protective antigen (PA), edema factor (EF), and lethal factor (LF). Combination of LF and PA or EF and PA are named anthrax lethal toxin (LeTx) and edema toxin (EdTx), respectively. PA is the receptor binding toxin component that attaches to either of two host cell receptors: anthrax toxin receptor 1 (ANTXR1 or tumor endothelial marker 8/TEM8) and anthrax toxin receptor 2 (ANTXR2 or capillary morphogenesis protein 2/CMG2). After binding, PA is cleaved and the receptor-bound portions form a heptameric pore that binds EF or LF. The toxin complexes are endocytosed and delivered into the cytosol. The activities of LeTx and EdTx result in malfunction of the immune system, edema, shock, and death.

The current US human anthrax vaccine, BioThrax™, consists of aluminum hydroxide-adsorbed supernatant material, primarily protective antigen (PA) and undefined quantities of LF and EF, from fermentor cultures of a toxigenic, non-encapsulated strain of *B. anthracis*. Human vaccination with BioThrax™, requires six immunizations followed by annual boosters. A relatively high local reaction rate of 3.6% in humans has been reported. This underscores the need for development of new, improved anthrax vaccines. To date, there have been many attempts including research in the PI's lab to improve the safety profile and immunogenicity of the anthrax vaccine, including using multiple antigens. However, none of the candidate vaccines is close to be licensed for public use in the near future. Since anthrax is a disease that rarely occurs naturally in humans, it is more realistic to develop a post exposure prophylaxis instead of mass immunization with the licensed vaccine. It is shown herein that inhibition of ANTXR expression by RNA interference (RNAi) technology using specific anti-ANTXR small interfering RNA (siRNA) prevents cytotoxicity of anthrax toxins. The novel host-targeted treatment shown herein against anthrax, is an example of a composition and method that can be used to overcome the weakness of the current antibiotic treatment in case of antibiotic resistant bacterial infection.

Target-specific RNAi is a safe and effective approach to treat severe infectious diseases. Despite recent advances in anti-pathogen approaches, host-side therapeutic intervention remains largely unexplored. RNA interference (RNAi) can be used to target several important host factors to block anthrax toxin endocytosis and the downstream activation of the inflammasome. This approach may work alone, or complement currently available antibiotic treatment for improved post-exposure prophylaxis of anthrax. RNAi is a recently discovered phenomenon in which small double-stranded RNAs (dsRNAs) regulate specific gene expression. RNAi can be induced by either endogenously encoded small RNAs called microRNAs (miRNAs) or exogenously introduced small interfering RNAs (siRNAs). In either case, the 21-23 nucleotide dsRNAs associate in the cytoplasm with a protein complex called the RNA-induced silencing complex (RISC). One of the two RNA strands is degraded, and the other guiding strand guides the RISC to mediate the sequence-specific degradation of the corresponding mRNA (in the case of siRNAs) and/or translational repression by binding to the 3' untranslated region (UTR) (in the case of miRNAs). The existence of RNAi machinery makes it possible for exotic designer small RNAs [synthetic siRNA or small hairpin RNA (shRNA)] to be used for silencing virtually any gene of interest in a sequence-specific manner. Ever since externally introduced double-stranded siRNAs were shown to silence specific gene expression in mammalian cells, there has been tremendous interest in using them as a research tool as well as applying them as novel drugs for the treatment of disease. RNAi may be useful in treating a variety of infectious diseases, including HIV, dengue, West Nile, St. Louis encephalitis, and respiratory syncytial virus (RSV) infections [48-54]. Furthermore, recent results from phase I clinical studies of siRNA targeting RSV nucleo-capsid (N) protein as a treatment against RSV infection have demonstrated the safety and therapeutic potential of RNAi for human use. Therefore, RNAi can readily be transformed to an effective therapeutic strategy in combating anthrax, a disease that could otherwise result in considerable morbidity and mortality even with antibiotic treatment.

As used herein, the term "RNA interference" refers to a process in which a double-stranded RNA molecule changes the expression of a nucleic acid sequence with which the double-stranded or short hairpin RNA molecule shares substantial or total homology. While not being bound by theory, the mechanism of action may include, but is not limited to, direct or indirect down regulation of the expression of the critical genes involved in anthrax toxin-induced cell and organ damage cell surface receptor genes, decrease in the critical genes involved in anthrax toxin-induced cell and organ damage mRNA. The term "RNAi" includes an RNA sequence that elicits RNA interference, which can also be transcribed from a vector. Also used herein, the terms "short hairpin RNA" or "shRNA" refer to an RNA structure having a duplex region and a loop region that may be used to target the critical genes involved in anthrax toxin-induced cell and organ damage genes, in which the RNAis are expressed initially as shRNAs. Both shRNA and RNAi are encompassed by the present invention.

As used herein, the term "RNAi expression cassette" refers to a cassette having at least one romoter that drives the transcription of the RNAi, which can also be followed by a termination sequence or unit. In some instances, a vector for use with the present invention may include multiple promoters upstream from the RNAi expression cassette. Thus, the terms "RNAi expression construct" or "RNAi expression vector" refer to vectors that include at least one RNAi expression cassette that targets the critical genes involved in anthrax toxin-induced cell and organ damage genes.

Often, RNAi is optimized by using identical sequences between the target and the RNAi, however, RNA interference can be found with less than 100% homology. If there is less than 100% homology, e.g., 99%, 98%, 97%, 96%, or even 95%, 94%, 93%, 92%, 91% or even 90%, the complementary regions must be sufficiently homologous to each other to form the specific double stranded regions. The precise structural rules to achieve a double-stranded region effective to result in RNA interference have not been fully identified, but approximately 70% identity is generally sufficient. Accordingly, in some embodiments of the invention, the homology between the RNAi and critical genes involved in anthrax toxin-induced cell and organ damage genes is at least 70%, 80%, 85%, 90%, or even 95% nucleotide sequence identity, so long as the cell surface expression of the critical genes involved in anthrax toxin-induced cell and organ damage is significantly lowered.

A common consideration for designing RNAi for targeting critical genes involved in anthrax toxin-induced cell and organ damage, is the length of the nucleic acid or the insert of a vector, for example, it is known that 17 out of 21 nucleotides is sufficient to initiate RNAi, but in other circumstances, identity of 19 or 20 nucleotides out of 21 may be required. While not being bound by theory, greater homology is commonly used in the central portion of a double stranded region than at its ends.

The RNA expression products of the RNAi expression cassette lead to the generation of a double-stranded RNA (dsRNA) complex for inducing RNA interference and thus down-regulating or decreasing expression of the critical genes involved in anthrax toxin-induced cell and organ damage genes.

As used herein, the critical genes involved in anthrax toxin-induced cell and organ damage include, one or more host genes selected from G6pc, Rgs1, Fosl2, Hcar2, Cxcl2 and Cxcl3, or Serpine1 (PAI-1).

RNAi approach. Building upon the present inventors previous work with RNAi technology and anthrax research, an RNAi strategy was developed focus on the in vitro and in vivo effects of anthrax toxins on the cellular functions and signaling pathways in mouse liver and heart, and compositions and methods for preventing and/or treating the same after exposure. The present inventors identified critical genes involved in anthrax toxin-induced cell and organ damage using bioinformatics methods, and demonstrate herein an effective treatment based on these findings. Small interfering RNA (siRNA)-mediated gene silencing and knockout mice were utilized to demonstrate a novel protective strategy against anthrax toxins.

Figure 1B:
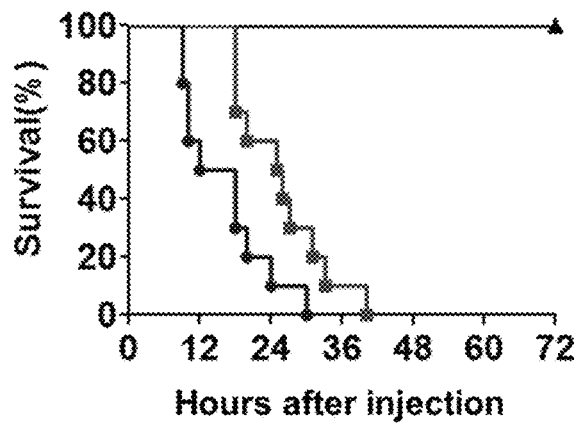

Anthrax EdTx rapidly impairs liver function in A/J mice. To examine the effects of EdTx on liver function in vivo, the present inventors injected 20 or 40 μg of EdTx into each A/J mouse and collected blood and tissue samples at various time points, as shown in FIG. 1A. The present inventors found that A/J mice were extremely sensitive to EdTx and showed initial signs of malaise at 30-60 min after injection. Mice receiving 20 or 40 μg of EdTx started to die within 40 h and 30 h after injection, respectively (FIG. 1B). Thus, the dose of 20 μg EdTx/mouse was used in subsequent studies, due to the relatively short period of time to death caused by 40 μg EdTx.

Figure 1C:
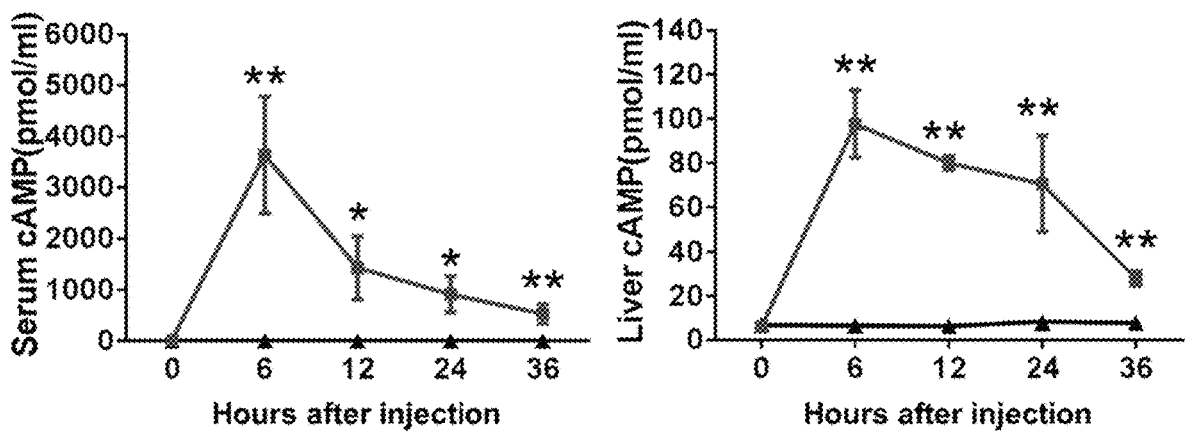
Figure 1D:
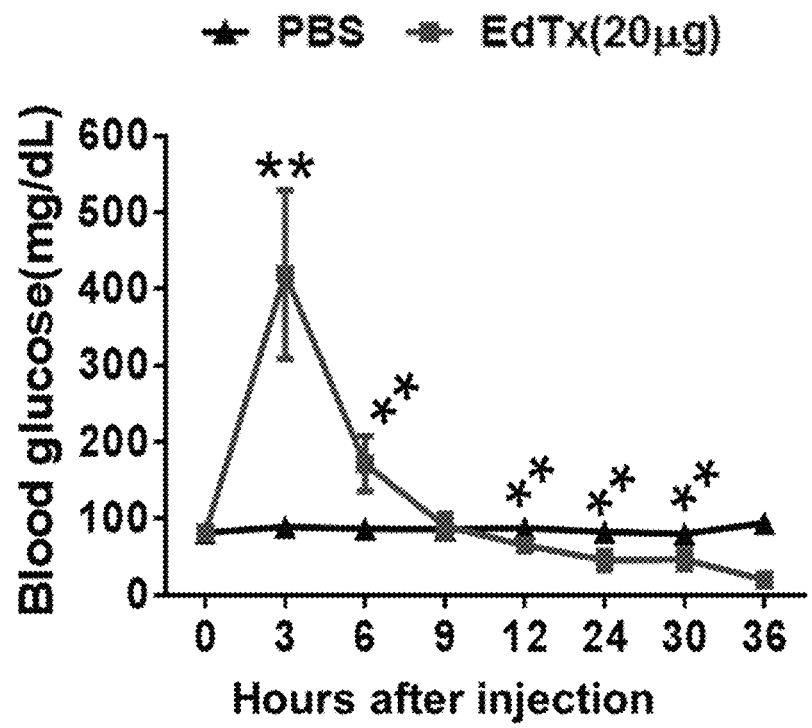

To evaluate the liver function of A/J mice challenged with EdTx, the present inventors monitored the levels of cAMP in serum and liver tissues. As shown in FIG. 1C, compared with those observed in PBS-injected control mice, the cAMP levels in EdTx-injected mice rapidly increased, peaking at 6 h (3636.8 pmol/mL vs. 3.2 pmol/mL in serum, P<0.01; 780.8 pmol/mL vs. 52.7 pmol/mL in liver, P<0.01), and gradually decreasing thereafter but remaining significantly higher than in control mice until death. Similarly, the level of blood glucose also rapidly increased, peaked at 3 h (419.4 mg/dL vs. 89.4 mg/dL in control, P<0.01), quickly decreased to the same level as in control mice (85.7 mg/dL) at nearly 9 h, and further declined until death (FIG. 1D).

To further evaluate the effects of EdTx on liver function, the present inventors conducted blood chemistry analyses at 18 h post-EdTx challenge. As shown in Table 1, the blood levels of biomarkers for liver function, such as aspartate aminotransferase (AST), alanine aminotransferase (ALT), alkaline phosphatase (ALP), and creatine kinase (CK), were found to be significantly higher in EdTx-challenged mice than in control mice. Albumin (ALB), globulin (GLB), and total protein (TP), which are mainly synthesized in liver, were found to be markedly lower in EdTx-challenged mice than in control mice. Moreover, blood urea nitrogen (BUN), creatinine (CREA), phosphorous (P), and potassium (K) in the renal panel were significantly elevated, while calcium (Ca) was notably reduced in EdTx-treated mice. Taken together, these results suggest that EdTx challenge leads to an acute deterioration of liver function in A/J mice.

TABLE 1

The effect of anthrax toxins on blood chemistry in mice.

| Blood Chemistry | Unit | PBS (A/J) | 20 μg EdTx (A/J) | PBS (Balb/c) | 50 μg LeTx (Balb/c) |
|---|---|---|---|---|---|
| Alanine Aminotransferase (ALT/SGPT) | U/L | 56.25 ± 22.90 | 242.60 ± 37.79** | 42.75 ± 8.88 | 172.50 ± 40.12** |
| Aspartate Aminotransferase (AST/SGOT) | U/L | 141.75 ± 42.30 | 281.00 ± 24.19** | 66.75 ± 8.62 | 398.00 ± 162.01** |
| Albumin (ALB) | g/dL | 3.08 ± 0.10 | 2.74 ± 0.21* | 2.68 ± 0.05 | 1.13 ± 0.30** |
| Globulin | g/dL | 1.90 ± 0.08 | 1.58 ± 0.08** | 2.25 ± 0.06 | 1.00 ± 0.28** |
| Albumin/Globulin (A/G) | | 1.63 ± 0.07 | 1.74 ± 0.15 | 1.20 ± 0.00 | 1.15 ± 0.13 |
| Alkaline Phosphatase (ALP) | U/L | 157.75 ± 40.42 | 240.40 ± 31.20* | 163.50 ± 18.64 | 142.00 ± 4.54 |
| Bicarbonate (TCO$_2$) | mmol/L | 19.00 ± 3.56 | 10.80 ± 4.02* | 22.00 ± 1.63 | 17.25 ± 7.75* |
| Blood Urea Nitrogen (BUN) | mg/dL | 25 ± 4.69 | 118.80 ± 20.86** | 30.25 ± 1.26 | 90.25 ± 36.70* |
| BUN: Creatinine ratio (B/C) | | 125.00 ± 23.45 | 180.66 ± 46.95 | 302.50 ± 12.58 | 546.67 ± 270.06 |
| Calcium (Ca) | mg/dL | 9.40 ± 0.18 | 6.88 ± 0.58** | 9.78 ± 0.17 | 7.75 ± 0.51** |
| Chloride (Cl) | mmol/L | 117.50 ± 1.73 | 113.00 ± 3.16* | 112.50 ± 3.00 | 120.50 ± 3.11* |
| Cholesterol (CHOL) | mg/dL | 78 ± 5.48 | 41.20 ± 3.19** | 125.50 ± 9.00 | 34.50 ± 11.00** |
| Creatine Kinase (CK) | U/L | 1699.25 ± 1108.74 | 7300.00 ± 3210.72* | 616.50 ± 109.42 | 1960.50 ± 980.46* |
| Creatinine (CREA) | mg/dL | 0.20 ± 0.00 | 0.68 ± 0.16** | 0.10 ± 0.00 | 0.10 ± 0.08 |
| Phosphorous (P) | mg/dL | 8.80 ± 1.03 | 19.94 ± 0.91** | 9.08 ± 1.02 | 9.30 ± 1.68 |
| Calcium: Phosphorous (Ca/P) | | 1.08 ± 0.13 | 0.35 ± 0.04** | 1.09 ± 0.14 | 0.85 ± 0.15 |
| Potassium (K) | mmol/L | 6.20 ± 0.54 | 9.40 ± 0.87** | 6.25 ± 0.42 | 6.38 ± 1.25 |
| Sodium (Na) | mmol/L | 154.25 ± 2.36 | 150 ± 3.40 | 154.50 ± 1.91 | 153.75 ± 0.96 |
| Sodium:Potassium Ratio (Na/K) | | 25.00 ± 2.45 | 16.00 ± 1.973** | 24.81 ± 1.74 | 24.73 ± 4.15 |
| Total Protein (TP) | g/dL | 4.98 ± 0.10 | 4.32 ± 0.21** | 4.93 ± 0.10 | 2.13 ± 0.57** |

Blood samples from all mice were collected at 18 hours after EdTx (20 μg/per mouse) or 24 hours after LeTx (50 μg/per mouse) challenging. The mean±S.D. for 4 replicates (n=4) from each group.*P<0.05 versus PBS group;**P<0.01 versus PBS group.

Figure 1E:
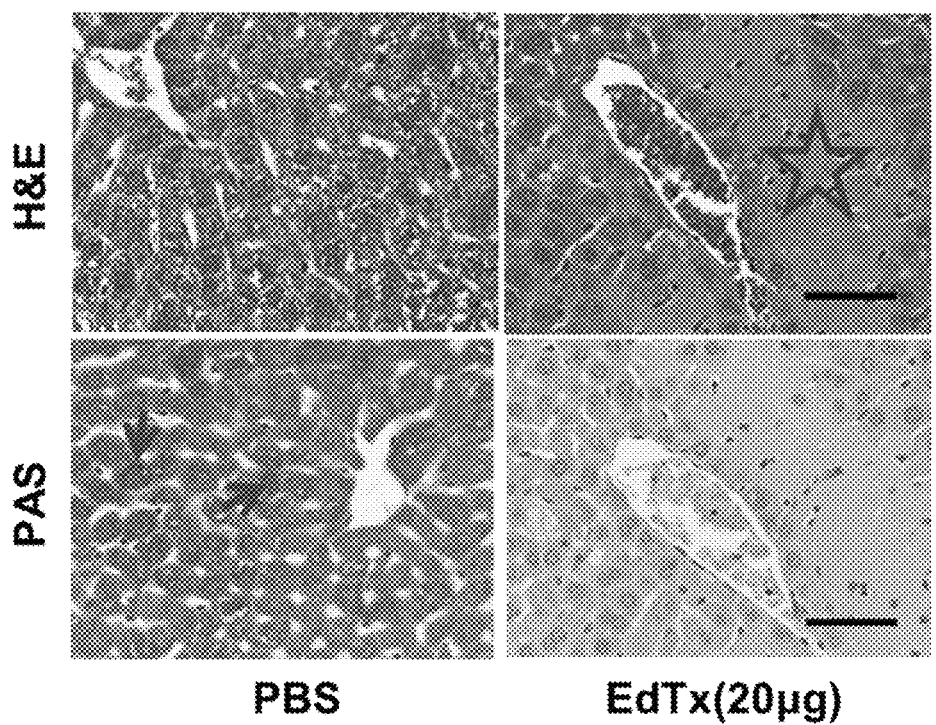
Figure 1F:
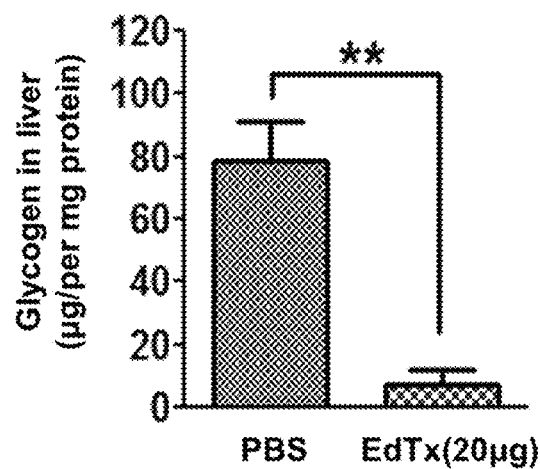

The present inventors further evaluated whether EdTx induced hepatic damage in A/J mice by performing H&E staining in the liver tissues collected from mice at 18 h after challenge with 20 μg of EdTx. As shown in FIG. 1E, characteristic signs of hepatocellular necrosis, such as "geographic-shape", eosinophilia, islands around the central hepatic veins, and a thin rim of surviving (viable) hepatocytes in close approximation to the vein wall, were found in the livers of EdTx-treated mice. Many of these lesions were asymmetrically distributed around the circumference of the vein. PAS staining showed less fuchsia staining within the livers of EdTx-treated mice than in control mice, suggesting a decrease in liver glycogen storage in response to EdTx challenge, which was further confirmed by glycogen assay (FIG. 1F). Collectively, these results show that EdTx induces acute hepatic damage in vivo, leading to a deterioration in liver function in A/J mice.

Figure 1G:
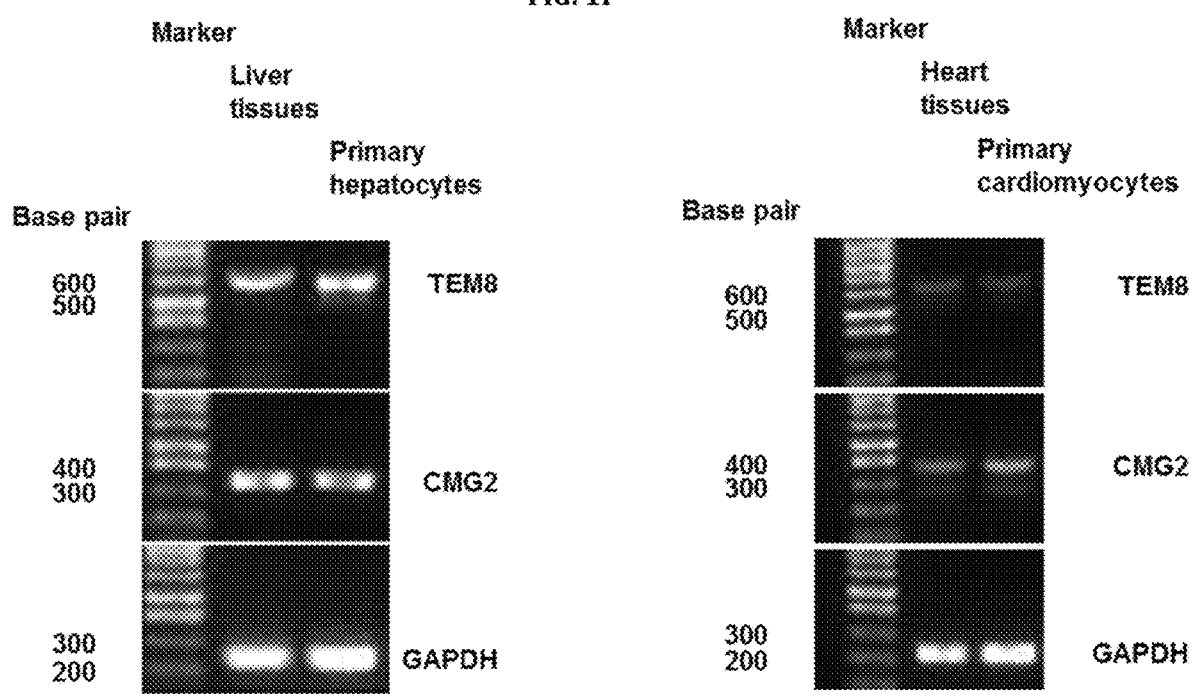
Figure 2A:
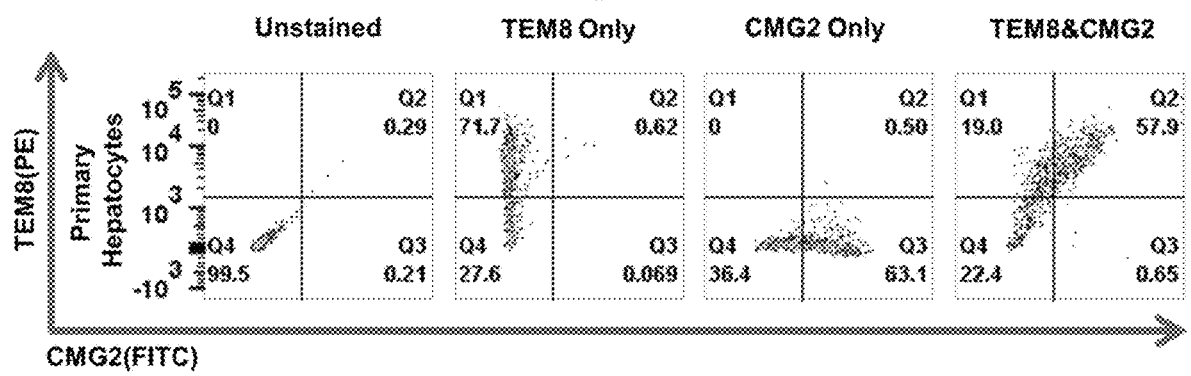
FIGS. 2A to 2H show that EdTx inhibited cell growth, promoted cell apoptosis, and induced cytotoxicity in primary hepatocytes.

Anthrax toxin receptors are expressed in mouse liver tissues and primary hepatocytes. Since anthrax toxin receptors are the entry channels required for anthrax toxin delivery into cells, RT-PCR and flow cytometry analyses were performed to assess the expression of two genes encoding anthrax toxin receptors, Tem8 and Cmg2, in primary hepatocytes and liver tissues of mice. As shown in FIG. 1G, transcripts of both Tem8 and Cmg2 were detectable in primary hepatocytes and liver tissues of A/J mice. Consistent with this finding, the results of flow cytometry also showed the presence of both TEM8 and CMG2 proteins on the surface of primary hepatocytes (FIG. 2A). These results suggest the presence of anthrax toxin receptors on the cell surface of hepatocytes, which provides the necessary mechanism for anthrax toxin delivery into the liver.

Figure 2B:
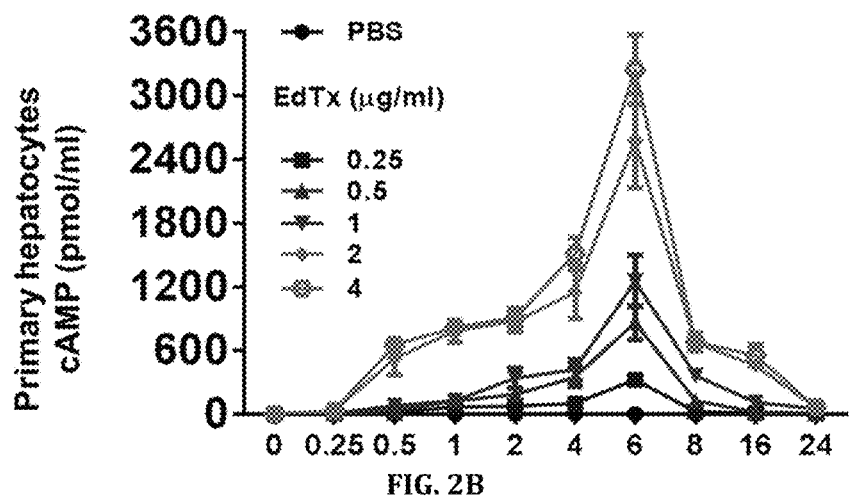
Figure 2C:
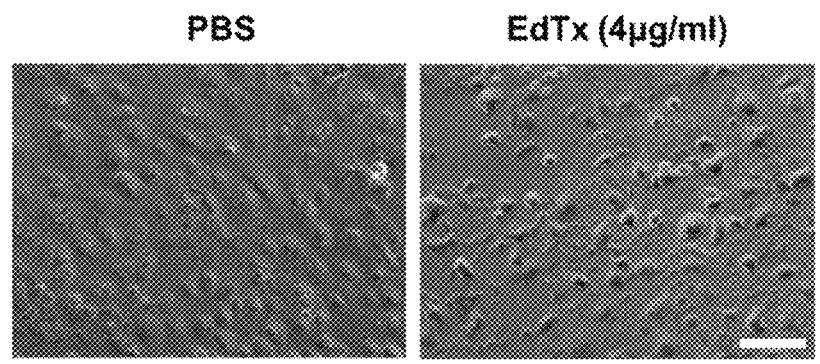
Figure 2D:
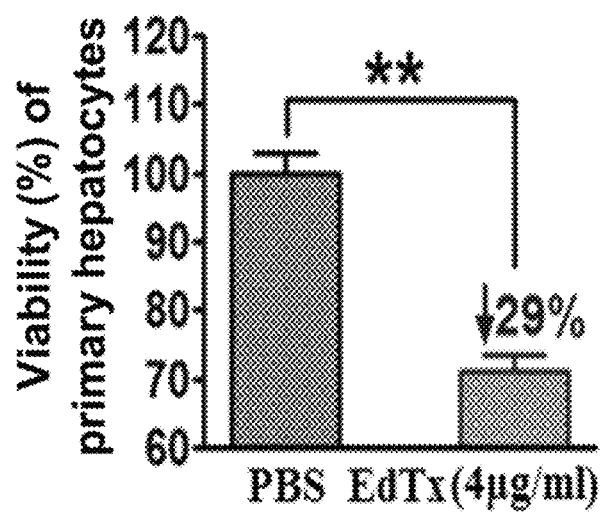

Anthrax EdTx inhibits cell growth, promotes cell apoptosis, and induces cytotoxicity in primary hepatocytes. To examine the effects of EdTx on primary hepatocytes in vitro, the intracellular levels of cAMP were determined at various time points within 24 h of treatment with 0.25, 0.5, 1, 2, and 4 ug/mL EdTx. PBS was used as a negative control. As shown in FIG. 2B, compared with that observed in control cells, the level of cAMP was dramatically increased (up to 3249.0±324.5 pmol/mL) within 6 h of EdTx treatment in a dose-dependent manner, and the peaks occurred at 6 h regardless of the dose. The level of cAMP then started to rapidly decrease at 6 h of EdTx treatment and finally reached the same level as in control cells at 24 h of treatment. Abnormal cell morphology, granulation of cytoplasm, contraction, disconnection, and cellular debris were observed by phase-contrast microscopy at 6 h after treatment with 4 μg/mL EdTx (FIG. 2C). Consistent with these observations, an MTT assay showed that the cell viability of primary hepatocytes treated with 4 μg/mL EdTx for 6 h was significantly reduced compared with PBS-treated cells (by 71%, P<0.01 vs. control, FIG. 2D). These results indicate that EdTx quickly induces cytotoxicity in primary hepatocytes and suppresses cell growth in vitro.

Figure 2E:
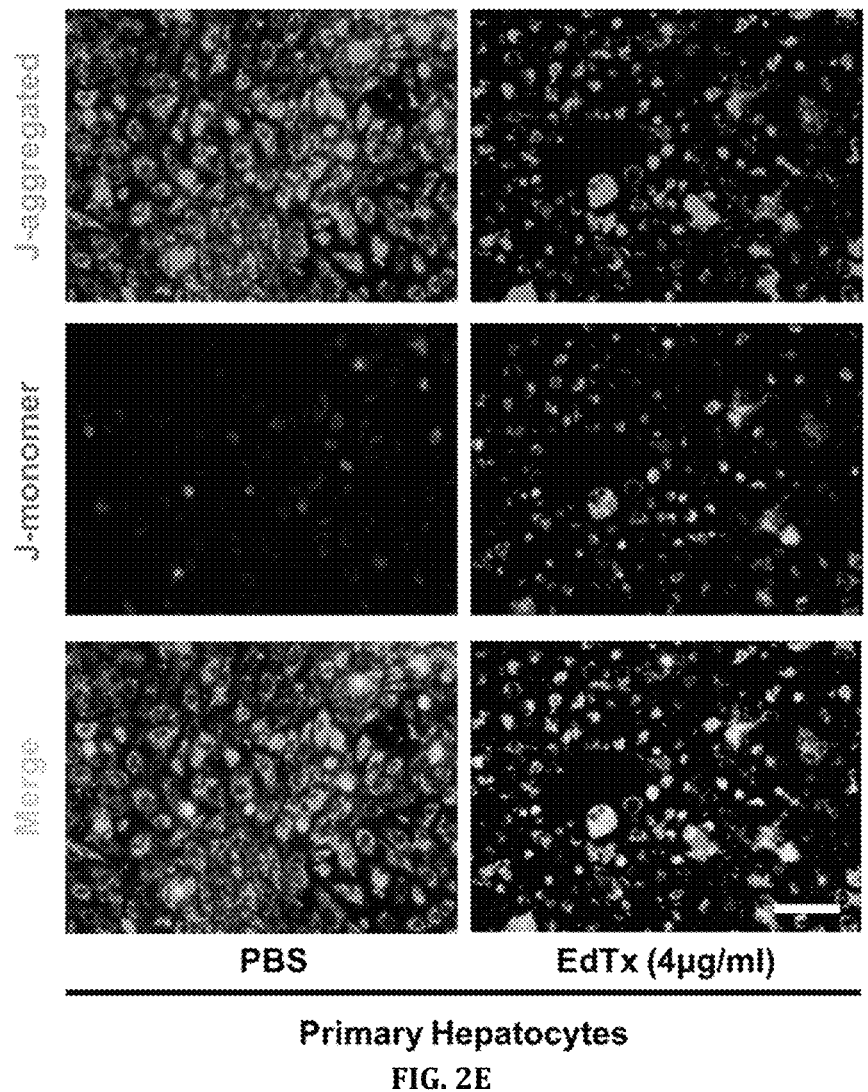

To investigate whether the reduction of primary hepatocyte growth was related to enhanced cell apoptosis, a mitochondrial membrane potential assay was performed, as mitochondria are the major energy generators in cells and play a critical role in stimulus-induced cell apoptosis. As shown in FIG. 2E, EdTx caused a decrease in red fluorescence (J-aggregates) and an increase in green fluorescence (J-monomers), due to the selective entry of J-monomers into the mitochondria, indicating a decrease in mitochondrial membrane potential in response to EdTx treatment. These results demonstrate that EdTx induces cell apoptosis in primary hepatocytes, resulting in suppression of cell growth and survival (FIG. 2E).

Figure 2F:
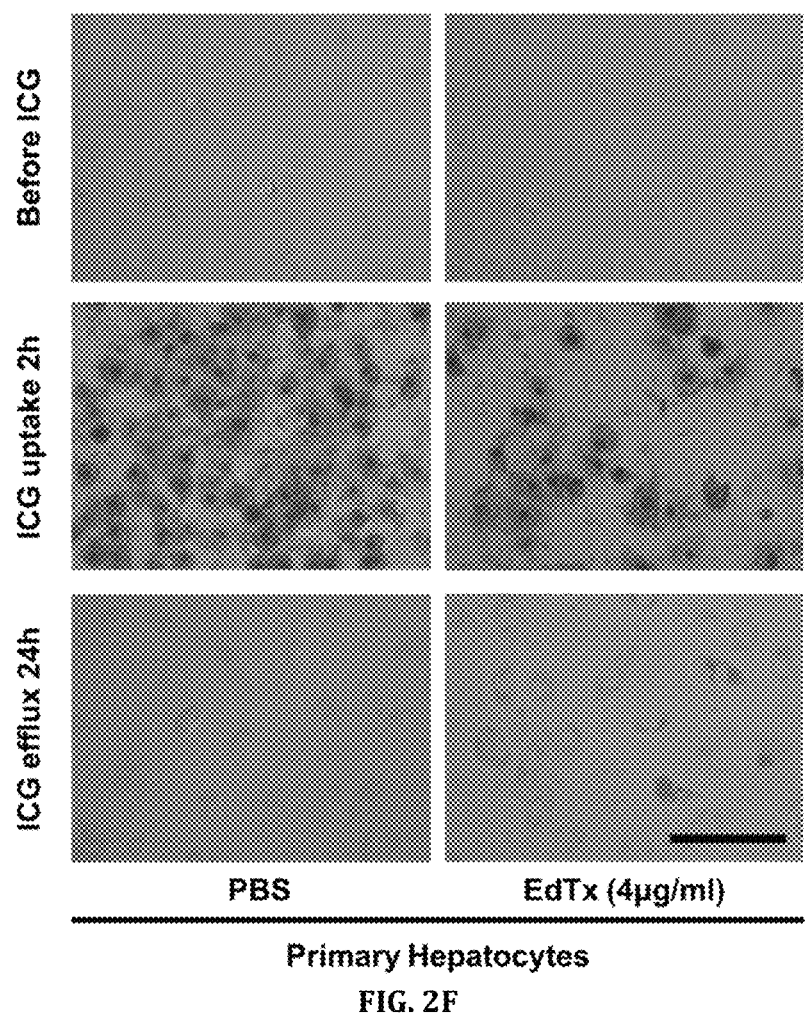
Figure 2G:
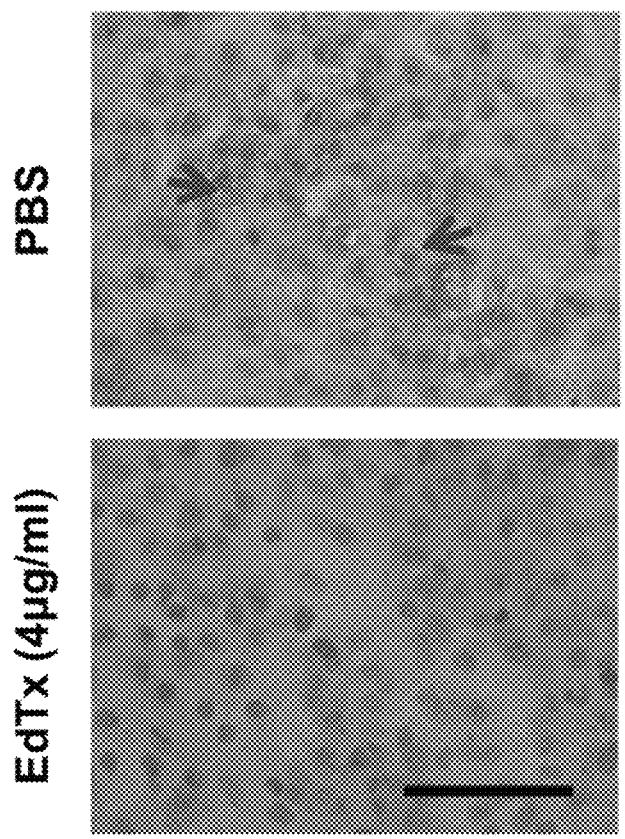
Figure 2H:
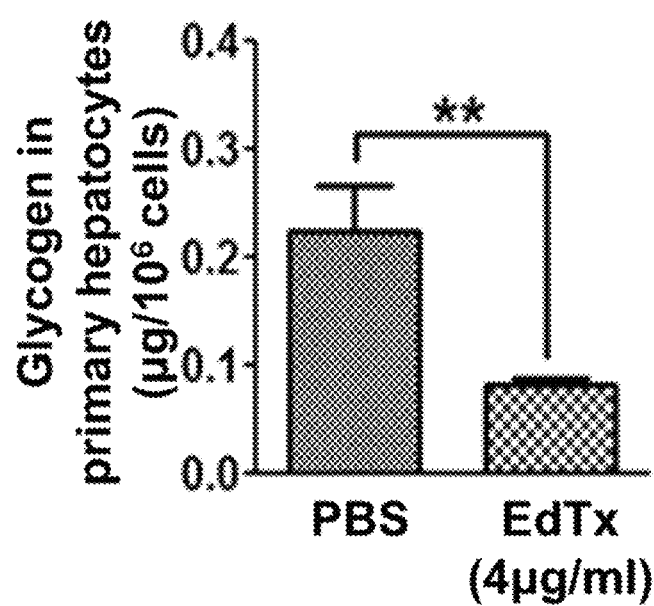

The metabolism of diverse compounds, involving their uptake, conjugation, and release, is an important function of hepatocytes. To further explore the effect of EdTx on liver function, an indocyanine green (ICG) uptake-and-release assay was performed. As shown in the middle panel of FIG. 2F, at 2 h after treatment with PBS or 4 mg/mL of EdTx approximately 84.00% of the PBS-treated cells absorbed ICG and exhibited a green-stained nucleus, whereas only 38.94% of the EdTx-treated cells had the ability to take up ICG (P<0.01). After 24 h of treatment, the number of ICG-positive cells dramatically decreased in both groups, but the green color in the EdTx-treated cells was more intense than in the PBS-treated cells (FIG. 2F, lower panel), suggesting an impaired ability of EdTx-treated hepatocytes to take up and release ICG. Furthermore, whether the primary hepatocytes could store glycogen was also examined, a characteristic of functional hepatocytes, using PAS staining. As shown in FIGS. 2G, 2H, EdTx-treated cells exhibited less storage of glycogen than PBS-treated cells (P<0.01 vs. control). Taken together, these results demonstrate that EdTx rapidly induces cytotoxicity in primary hepatocytes, leading to impaired uptake, release, and storage of diverse compounds.

Figure 3A:
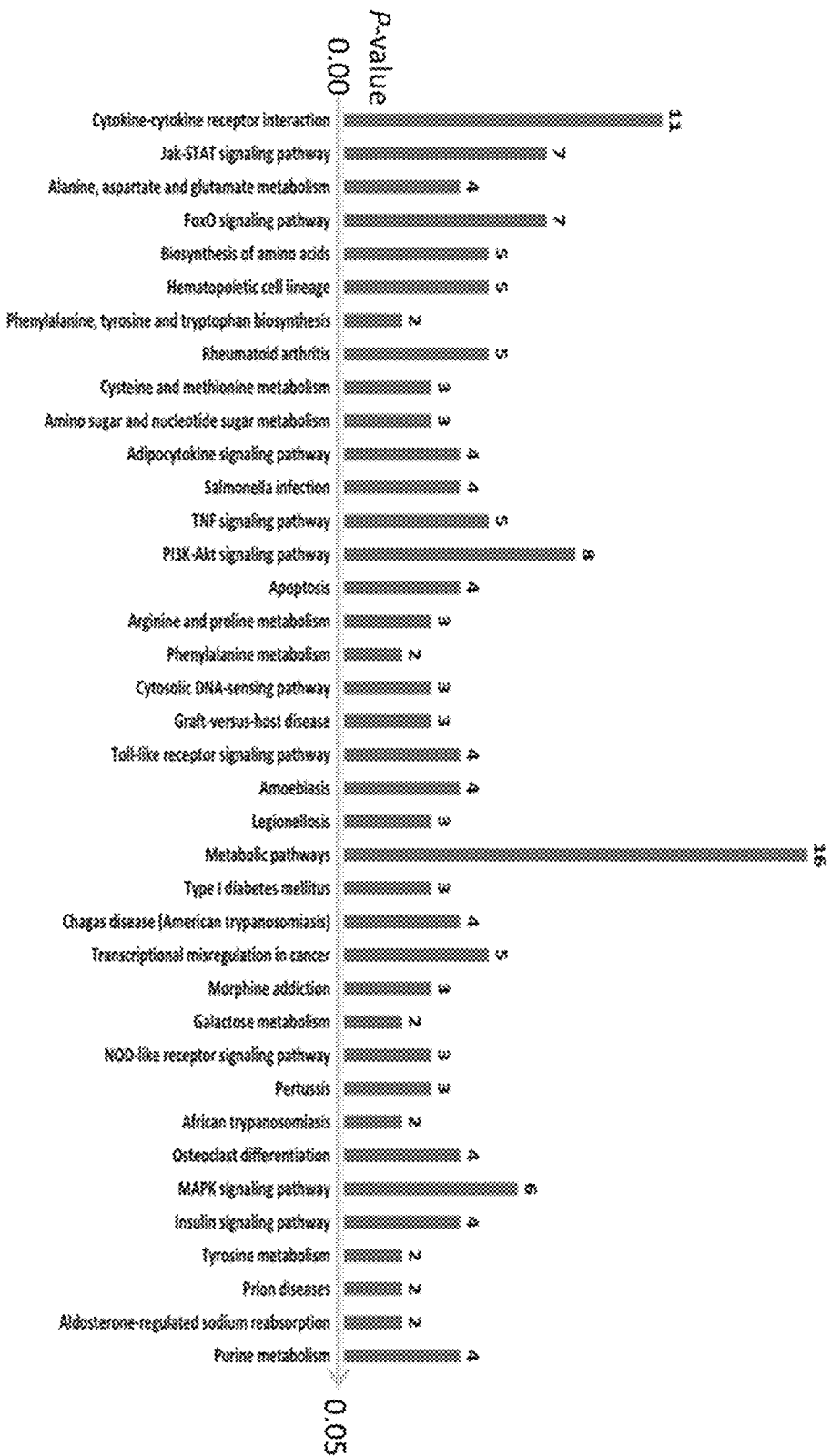

Identification of EdTx-mediated, cytotoxicity-related genes, and knockdown of these genes protects primary hepatocytes from EdTx-induced cytotoxicity. To investigate the mechanism underlying the toxicity of EdTx for hepatocytes, the present inventors conducted a microarray assay to identify potential genes related to impaired liver function induced by EdTx treatment. The results showed that 218 genes underwent a significant change in gene expression (log ratio >2 or log ratio <0.5, P<0.05) in primary hepatocytes exposed to EdTx compared with PBS-treated cells (Table 2). Based on these differentially expressed genes, 38 signaling pathways were identified as significantly changed (enrichment score >2, P<0.05, FIG. 3A). The microarray data had been submitted to GEO and the accession numbers is GSE115844.

TABLE 2

EdTx-mediated effects on the expression of genes in mouse primary hepatocytes and livers.

| Gene name (218) | Gene bank ID | Mouse primary hepatocytes Microarray (log ratio) | qPCR (fold change) | Mouse Livers qPCR (fold change) |
|---|---|---|---|---|
| Amino Acid Metabolism (9) | | | | |
| *Mus musculus* arginase type II (Arg2) | NM_009705 | 4.311* | 27.939* | 28.806* |
| *Mus musculus* argininosuccinate synthetase 1 (Ass1) | NM_007494 | 2.310** | 3.17 | 1.062 |
| *Mus musculus* cystathionine beta-synthase (Cbs), transcript variant 3 | NM_001271353 | 2.557* | 5.854 | 0.454* |
| *Mus musculus* carbamoyl-phosphate synthetase 1 (Cps1) | NM_001080809 | 2.186* | 11.582** | 0.945 |
| *Mus musculus* glutamate oxaloacetate transaminase 1, soluble (Got1) | NM_010324 | 2.118* | 2.957* | 6.584** |
| *Mus musculus* phenylalanine hydroxylase (Pah) | NM_008777 | 3.618 | 4.021* | 0.609 |
| *Mus musculus* tyrosine aminotransferase (Tat) | NM_146214 | 7.949* | 34.729** | 8.537* |
| *Mus musculus* glutamine fructose-6-phosphate transaminase 1 (Gfpt1) | NM_013528 | 2.720** | 1.622 | 0.858 |
| *Mus musculus* glutamine fructose-6-phosphate transaminase 2 (Gfpt2) | NM_013529 | 3.056** | 4.686** | 8.546** |
| Glucose Metabolism (30) | | | | |
| *Mus musculus* aldo-keto reductase family 1, member B7 (Akr1b7) | NM_009731 | 3.731** | 9.450** | 12.204* |
| *Mus musculus* UDP-GlcNAc:betaGal beta-1,3-N-acetylglucosaminyltransferase 5 (B3gnt5), transcript variant 1 | NM_001159407 | 2.472** | 0.684 | 2.061 |
| *Mus musculus* cAMP responsive element modulator (Crem), transcript variant 4 | NM_001110850 | 2.664** | 1.431 | 1.04 |
| *Mus musculus* colony stimulating factor 2 receptor, beta, low-affinity (granulocyte-macrophage) (Csf2rb) | NM_007780 | 2.049* | 3.004** | 2.169* |
| *Mus musculus* colony stimulating factor 2 receptor, beta 2, low-affinity (granulocyte-macrophage) (Csf2rb2), transcript variant 2 | NM_001287389 | 2.243* | 2.159 | 1.041 |
| *Mus musculus* cytochrome P450, family 17, subfamily a, polypeptide 1 (Cyp17a1), mRNA | NM_007809 | 5.090* | 4.367** | 8.945 |
| *Mus musculus* diacylglycerol O-acyltransferase 1 (Dgat1) | NM_010046 | 2.821** | 3.342** | 1.027 |
| *Mus musculus* ectonucleoside triphosphate diphosphohydrolase 1 (Entpd1) | NM_009848 | 2.625* | 5.781 | 0.389* |
| *Mus musculus* ethanolamine phosphate phospholyase (Etnppl), transcript variant 2 | NM_001163587 | 3.003* | 13.436 | 1.816 |
| *Mus musculus* glucose-6-phosphatase, catalytic (G6pc) | NM_008061 | 9.942** | 15.496* | 3.395* |
| *Mus musculus* GTP binding protein (gene overexpressed in skeletal muscle) (Gem) | NM_010276 | 2.322* | 3.356 | 2.211 |
| *Mus musculus* hematopoietic prostaglandin D synthase (Hpgds) | NM_019455 | 0.465** | 0.39 | 1.052 |
| *Mus musculus* leptin receptor (Lepr), transcript variant 3 | NM_001122899 | 2.258* | 2.051 | 2.126 |
| *Mus musculus* phosphoenolpyruvate carboxykinase 1, cytosolic (Pck1) | NM_011044 | 4.020* | 42.022** | 3.935* |
| *Mus musculus* phosphodiesterase 3B, cGMP-inhibited (Pde3b) | NM_011055 | 2.010* | 3.044** | 0.523 |
| *Mus musculus* phosphodiesterase 4B, cAMP specific (Pde4b) | NM_001177980 | 2.059** | 5.780** | 3.734* |
| *Mus musculus* peroxisome proliferative activated receptor, gamma, coactivator 1 alpha (Ppargc1a), transcript variant 1 | NM_008904 | 3.345** | 0.637 | 1.603 |
| *Mus musculus* protein tyrosine phosphatase, receptor type, N (Ptprn) | NM_008985 | 2.077* | 3.130* | 3.954* |
| *Mus musculus* receptor (calcitonin) activity modifying protein 3 (Ramp3) | NM_019511 | 3.449** | 20.345* | 9.753* |
| *Mus musculus* retinol dehydrogenase 12 (Rdh12) | NM_030017 | 2.524** | 4.434** | 9.536** |
| *Mus musculus* regulator of G-protein signaling 1 (Rgs1) | NM_015811 | 6.364** | 15.230* | 21.550* |
| *Mus musculus* regulator of G-protein signaling 2 (Rgs2) | NM_009061 | 2.205** | 3.106* | 2.363* |
| *Mus musculus* serum/glucocorticoid regulated kinase 1 (Sgk1) | NM_001161845 | 2.375** | 6.049* | 3.990* |
| *Mus musculus* salt inducible kinase 1 (Sik1) | NM_010831 | 3.464** | 3.944* | 8.057** |
| *Mus musculus* solute carrier family 25 (mitochondrial carrier, phosphate carrier), member 25 (Slc25a25) | NM_001164357 | 2.593** | 3.403** | 4.928* |
| *Mus musculus* thromboxane A synthase 1, platelet (Tbxas1) | NM_011539 | 0.496* | 0.085** | 0.303* |
| *Mus musculus* transforming growth factor, beta receptor I (Tgfbr1) | NM_009370 | 2.065** | 1.808 | 0.608 |
| *Mus musculus* transglutaminase 2, C polypeptide (Tgm2) | NM_009373 | 2.419** | 3.422* | 7.330* |
| *Mus musculus* UDP-N-acetylglucosamine pyrophosphorylase 1 (Uap1) | NM_133806 | 3.069** | 2.926 | 0.87 |
| *Mus musculus* uridine-cytidine kinase 2 (Uck2) | NM_030724 | 2.112** | 3.309* | 4.623 |
| Inflammation and Apoptosis (31) | | | | |
| *Mus musculus* bone morphogenetic protein 7 (Bmp7) | NM_007557 | 2.182* | 7.021* | 0.839 |
| *Mus musculus* complement component 3a receptor 1 (C3ar1) | NM_009779 | 0.405* | 0.257 | 0.948 |
| *Mus musculus* CD180 antigen (Cd180) | NM_008533 | 0.251** | 0.051 | 0.793 |
| *Mus musculus* CD55 antigen (Cd55) | NM_010016 | 2.243** | 4.209 | 0.387** |
| *Mus musculus* CD86 antigen (Cd86) | NM_019388 | 2.021** | 2.673 | 0.605 |
| *Mus musculus* chemokine (C-X-C motif) ligand 2 (Cxcl2) | NM_009140 | 3.897** | 9.148* | 47.234** |
| *Mus musculus* chemokine (C-X-C motif) ligand 3 (Cxcl3) | NM_203320 | 2.694** | 30.073* | 57.163** |
| *Mus musculus* cysteine rich protein 61 (Cyr61) | NM_010516 | 0.388* | 0.149** | 1.609 |
| *Mus musculus* egl-9 family hypoxia-inducible factor 3 (Egln3) | NM_028133 | 3.045** | 5.595** | 0.822 |
| *Mus musculus* coagulation factor V (F5) | NM_007976 | 2.061* | 6.505** | 7.324* |
| *Mus musculus* FBJ osteosarcoma oncogene (Fos) | NM_010234 | 3.521* | 3.402** | 44.446** |
| *Mus musculus* fos-like antigen 2 (Fosl2) | NM_008037 | 2.162** | 3.398** | 5.561* |
| *Mus musculus* hydroxycarboxylic acid receptor 2 (Hcar2) | NM_030701 | 2.371** | 2.935* | 35.325** |
| *Mus musculus* hypoxia inducible lipid droplet associated (Hilpda) | NM_001190461 | 3.106** | 5.851* | 28.508** |
| *Mus musculus* insulin-like growth factor 1 (Igf1) | NM_001111274 | 0.482** | 0.373** | 0.435** |
| *Mus musculus* interleukin 11 (Il11) | NM_008350 | 2.535* | 12.214* | 4.905* |

TABLE 2-continued

EdTx-mediated effects on the expression of genes in mouse primary hepatocytes and livers.

| Gene name (218) | Gene bank ID | Mouse primary hepatocytes Microarray (log ratio) | qPCR (fold change) | Mouse Livers qPCR (fold change) |
|---|---|---|---|---|
| *Mus musculus* interleukin 1 beta (Il1b) | NM_008361 | 13.017** | 21.006* | 4.225* |
| *Mus musculus* interleukin 1 receptor, type II (Il1r2) | NM_010555 | 3.212** | 5.765** | 76.847* |
| *Mus musculus* interleukin 33 (Il33), transcript variant 1 | NM_001164724 | 5.614** | 3.925* | 2.605 |
| *Mus musculus* interleukin 6 (Il6) | NM_031168 | 4.242** | 1.548 | 3.711 |
| *Mus musculus* interleukin 7 receptor (Il7r) | NM_008372 | 2.036* | 4.15 | 1.768 |
| *Mus musculus* nerve growth factor (Ngf), transcript variant 2 | NM_01112698 | 2.220* | 4.430* | 1.56 |
| *Mus musculus* nuclear receptor subfamily 4, group A, member 2 (Nr4a2) | NM_001139509 | 6.330* | 8.035* | 4.372** |
| *Mus musculus* nuclear receptor subfamily 4, group A, member 3 (Nr4a3) | NM_015743 | 4.432* | 2.943* | 4.231** |
| *Mus musculus* protein C receptor, endothelial (Procr) | NM_011171 | 2.473* | 8.688 | 1.755 |
| *Mus musculus* RasGEF domain family, member 1B (Rasgef1b) | NM_145839 | 2.210* | 3.493* | 8.485** |
| *Mus musculus* steroidogenic acute regulatory protein (Star) | NM_011485 | 3.116* | 9.675* | 1.125 |
| *Mus musculus* toll-like receptor 7 (Tlr7), transcript variant 3 | NM_133211 | 0.309* | 0.237 | 0.795 |
| *Mus musculus* tumor necrosis factor alpha induced protein 6 (Tnfaip6) | NM_009398 | 2.886** | 3.496* | 8.212* |
| *Mus musculus* triggering receptor expressed on myeloid cells 1 (Trem1) | NM_021406 | 6.643* | 7.024* | 6.629** |
| *Mus musculus* vascular endothelial growth factor A (Vegfa), transcript variant 1 | NM_001025250 | 2.085** | 3.234* | 0.599 |
| Others (55) | | | | |
| Gm20412: havana: putative chromosome | ENSMUST00000173249 | 2.74** | | |
| *Mus musculus* achaete-scute complex homolog 1 (*Drosophila*) (Ascl1) | NM_008553 | 5.083** | | |
| *Mus musculus* microRNA 223 (Mir223) | NR_029801 | 0.444** | | |
| *Mus musculus* RIKEN cDNA 9930111J21 gene 1 (9930111J21Rik1) | NM_001114679 | 0.365** | | |
| *Mus musculus* protein phosphatase 1K (PP2C domain containing) (Ppm1k) | NM_175523 | 2.400** | | |
| *Mus musculus* RIKEN cDNA 9930111J21 gene 2 (9930111J21Rik2) | NM_173434 | 0.359* | | |
| *Mus musculus* klotho beta (Klb) | NM_031180 | 2.023** | | |
| *Mus musculus* ATP-binding cassette, sub-family D (ALD), member 2 (Abcd2) | NM_011994 | 0.471** | | |
| *Mus musculus* expressed sequence AI607873 (AI607873) | NM_001204910 | 0.372** | | |
| *Mus musculus* hyaluronan synthase1 (Has1) | NM_008215 | 2.396** | | |
| Gm5424:ensembl:known chromosome | ENSMUST00000053865 | 2.547** | | |
| *Mus musculus* cytohesin 1 interacting protein (Cytip) | NM_139200 | 5.391** | | |
| *Mus musculus* synaptotagmin-like 2 (Sytl2), transcript variant 2 | NM_001040085 | 2.817** | | |
| *Mus musculus* apolipoprotein B mRNA editing enzyme, catalytic polypeptide 1 (Apobec1), transcript variant 2 | NM_001134391 | 0.342** | | |
| *Mus musculus* predicted gene 5431 (Gm5431) | NM_001024230 | 0.434** | | |
| Gm15675: havana: known chromosome | ENSMUST00000130486 | 2.246** | | |
| *Mus musculus* sestrin 1 (Sesn1), transcript variant 2 | NM_001013370 | 0.482** | | |
| *Mus musculus* neurofilament, light polypeptide (Nefl) | NM_010910 | 2.259** | | |
| Gm24060: ncrna: known chromosome | ENSMUST00000157494 | 2.245** | | |
| *Mus musculus* glycerophosphocholine phosphodiesterase GDE1 homolog (*S. cerevisiae*) (Gpcpd1), transcript variant 3 | NM_001042671 | 2.071** | | |
| Gm379: ensembl: known chromosome | ENSMUST00000178160 | 2.263** | | |
| *Mus musculus* placenta expressed transcript 1 (Plet1) | NM_029639 | 2.172** | | |
| *Mus musculus* vitamin D receptor (Vdr) | NM_009504 | 2.156** | | |
| *Mus musculus* solute carrier family 15, member 3 (Slc15a3) | NM_023044 | 2.250** | | |
| *Mus musculus* neuromedin U (Nmu) | NM_019515 | 2.005** | | |
| *Mus musculus* synaptosomal-associated protein 25 (Snap25), transcript variant 1 | NM_011428 | 2.090** | | |
| *Mus musculus* tetratricopeptide repeat domain 39B (Ttc39b) | NM_027238 | 2.077** | | |
| Gm27031: havana: known chromosome | ENSMUST00000181988 | 2.029** | | |
| *Mus musculus* serine palmitoyltransferase, small subunit B (Sptssb), transcript variant 1 | NM_001164210 | 3.770** | | |
| *Mus musculus* CD83 antigen (Cd83), transcript variant 1 | NM_001289915 | 2.253* | | |
| *Mus musculus* hect domain and RLD 4 (Herc4), transcript variant 2 | NM_026101 | 2.200* | | |
| *Mus musculus* C-type lectin domain family 5, member a (Clec5a), transcript variant 1 | NM_001038604 | 0.425* | | |
| *Mus musculus* immediate early response 3 (Ier3) | NM_133662 | 2.024* | | |
| *Mus musculus* phosphodiesterase 10A (Pde10a), transcript variant 2 | NM_011866 | 2.241* | | |
| *Mus musculus* ring finger protein 125 (Rnf125) | NM_026301 | 2.789* | | |
| *Mus musculus* ISY1 splicing factor homolog (*S. cerevisiae*) (Isy1) | NM_133934 | 2.157* | | |
| *Mus musculus* solute carrier family 7 (cationic amino acid transporter, y+ system), member 2 (Slc7a2), transcript variant 2 | NM_001044740 | 3.455* | | |
| *Mus musculus* solute carrier family 25 (mitochondrial carrier ornithine transporter), member 15 (Slc25a15) | NM_181325 | 2.465* | | |
| PREDICTED: *Mus musculus* uncharacterized LOC100503338 (LOC100503338), ncRNA | XR_106025 | 0.412* | | |
| *Mus musculus* hepatitis A virus cellular receptor 2 (Havcr2) | NM_134250 | 2.201* | | |
| *Mus musculus* microRNA 493 (Mir493) | NR_030573 | 2.108* | | |
| *Mus musculus* olfactory receptor 111 (Olfr111) | NM_001005485 | 0.388* | | |

TABLE 2-continued

EdTx-mediated effects on the expression of genes in mouse primary hepatocytes and livers.

| Gene name (218) | Gene bank ID | Mouse primary hepatocytes Microarray (log ratio) | qPCR (fold change) | Mouse Livers qPCR (fold change) |
|---|---|---|---|---|
| *Mus musculus* keratin 23 (Krt23) | NM_033373 | 2.267* | | |
| *Mus musculus* toll-like receptor 13 (Tlr13) | NM_205820 | 0.358* | | |
| n-R5s54: ncrna: known chromosome | ENSMUST00000083837 | 3.603* | | |
| *Mus musculus* uncharacterized LOC102631757 (LOC102631757), transcript variant 2, long non-coding RNA | NR_110502 | 2.096* | | |
| *Mus musculus* nuclear factor, interleukin 3, regulated (Nfil3) | NM_017373 | 2.113* | | |
| *Mus musculus* protein tyrosine phosphatase-like A domain containing 2 (Ptplad2) | NM_025760 | 0.420* | | |
| *Mus musculus* insulin-like growth factor binding protein 1 (Igfbp1) | NM_008341 | 2.372* | | |
| *Mus musculus* tandem C2 domains, nuclear (Tc2n), transcript variant 2 | NM_001082976 | 2.177* | | |
| *Mus musculus* osteoglycin (Ogn) | NM_008760 | 0.361* | | |
| *Mus musculus* lumican (Lum) | NM_008524 | 0.436* | | |
| *Mus musculus* elongation of very long chain fatty acids (FEN1/Elo2, SUR4/Elo3, yeast)-like 2 (Elovl2) | NM_019423 | 2.100* | | |
| *Mus musculus* CD84 antigen (Cd84), transcript variant 2 | NM_001252472 | 0.448* | | |
| *Mus musculus* C-type lectin domain family 4, member d (Clec4d), transcript variant 2 | NM_001163161 | 2.031* | | |
| Unknown (93) | | | | |

Data not shown.

The log ratio is defined as log2 (EdTx-treated group/PBS-treated group).
*$P < 0.05$ and **$P < 0.01$ versus PBS-treated group.

Figure 3B:
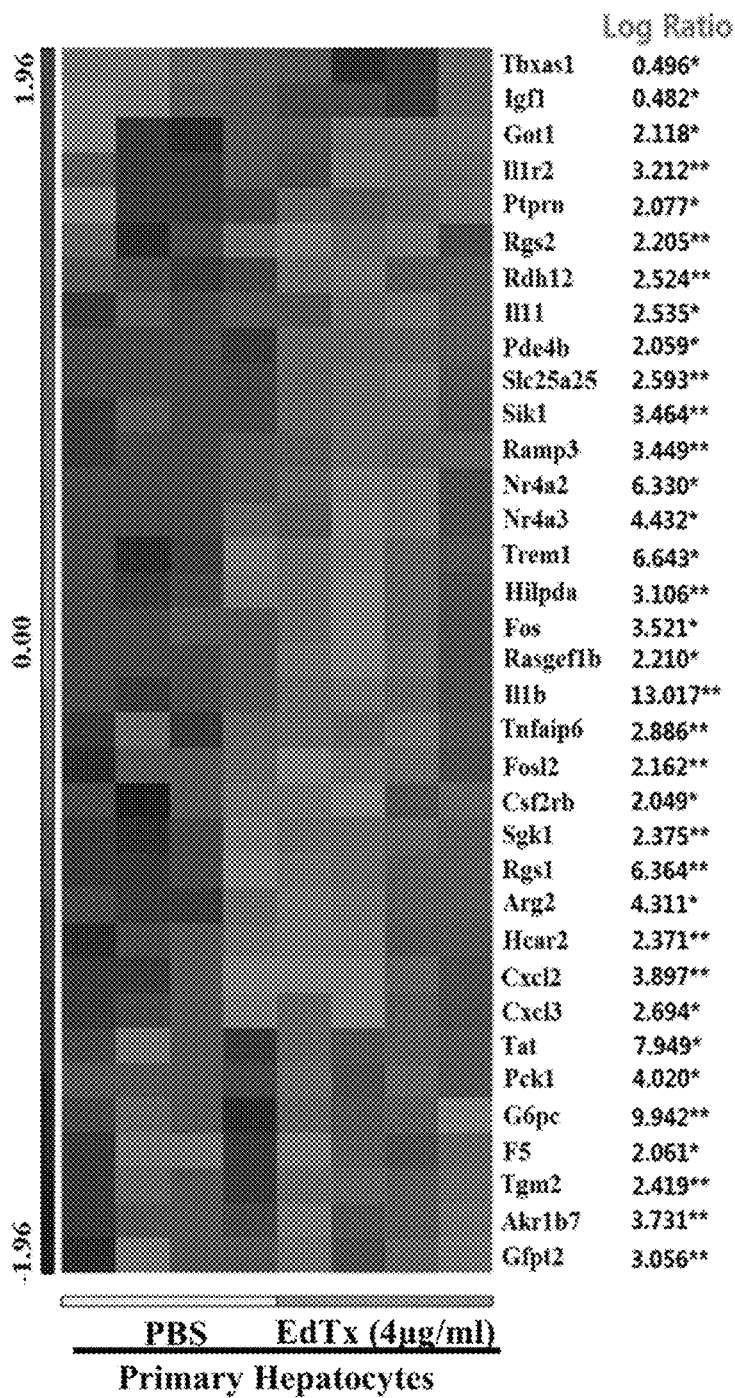
Figure 3C:
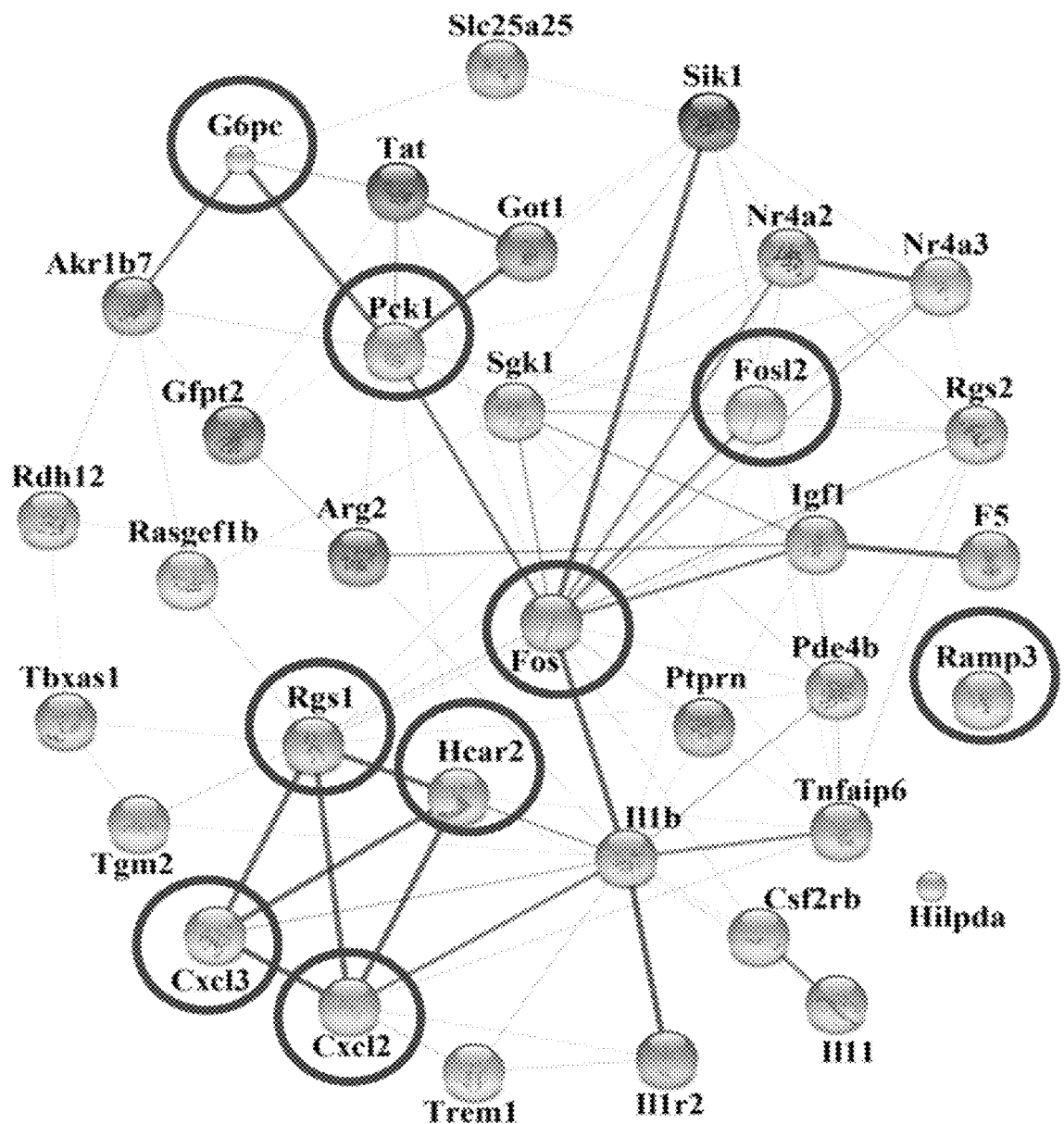

In order to verify the microarray results, the present inventors performed qPCR analyses for 70 genes selected from these signaling pathways using RNA from the same samples that had been used for the microarray assay as well as RNA from liver tissues of mice receiving the same PBS or EdTx treatment. Of note, the expression changes of 35 genes were confirmed (P<0.05, vs. control) in both primary hepatocytes and liver tissue (Table 2). The microarray results for these 35 genes are shown in FIG. 3B. To further understand the association among these 35 genes, a protein-protein network analysis was conducted using STRING 10 software. The results showed strong associations among the Akrlb7, G6pc, Pck1, Got, Fos, Fosl2, Sik1, Nr4a2, Nr4a3, Igf1, F5, Il1b, Tnfaip6, Il1r2, Rgs1, Hcar2, Cxcl2, and Cxcl3 genes (FIG. 3C). Nine genes, including G6pc, Pck1, Fosl2, Ramp3, Fos, Rgs1, Hcar2, Cxcl2, and Cxcl3, that are involved in glycogen metabolism, cAMP production, and cell apoptosis for further evaluation. To investigate whether these nine genes are related to the cytotoxicity induced by EdTx in primary hepatocytes, these genes were knocked down in hepatocytes using the corresponding siRNAs, and the knockdown efficiency for each gene determined.

Figures 3D, 4A:
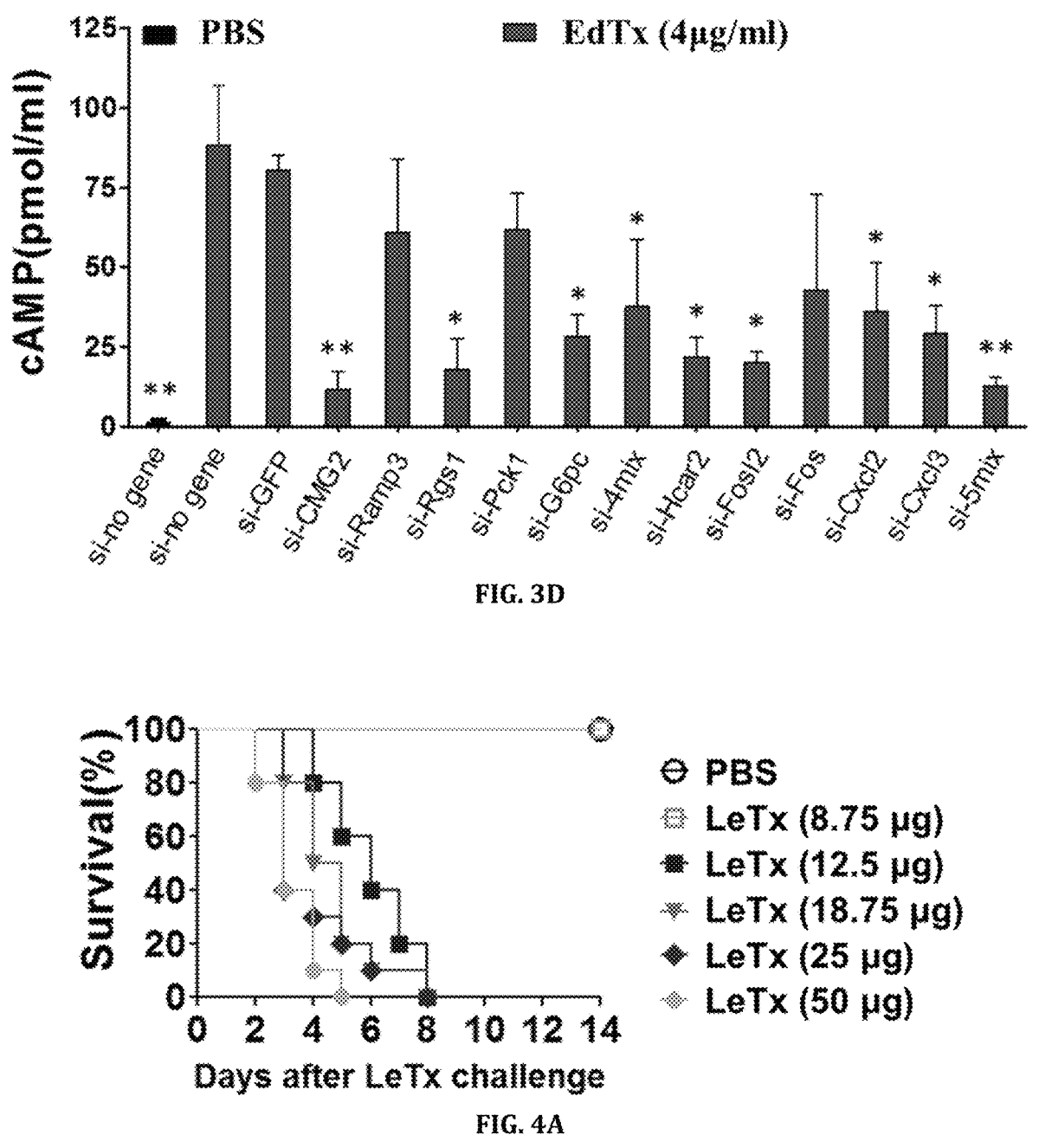

Since it is well established that EdTx induces a rise in the intracellular concentration of cAMP, which is commonly considered an indicator of EdTx-induced cytotoxicity (Jaswal et al., 2017), the level of cAMP using cAMP-specific ELISA was used to explore whether silencing of Cmg2, a positive control, or any of the 9 genes protects primary hepatocytes from EdTx-induced injury. As shown in FIG. 3D, after treating with EdTx for 1 h, the intracellular level of cAMP was significantly increased (by up to 88.4 pmol/ml) in si-(no gene)- or si-GFP-transfected cells compared with PBS-treated cells. Interestingly, in EdTx-treated cells, knockdown of Cmg2, Rgs1, Hcar2, Fosl2, Cxcl2, Cxcl3, Ramp3+Rgs1+Pck1+G6pc, or Ramp3+Rgs1+Pck1+G6pc significantly reversed the inductive effect of EdTx on the cAMP level, showing that these genes are essential in EdTx-induced cytotoxicity and that knockdown of these genes, individually or in combination, protects primary hepatocytes against the toxicity induced by EdTx in vitro.

Figure 4B:
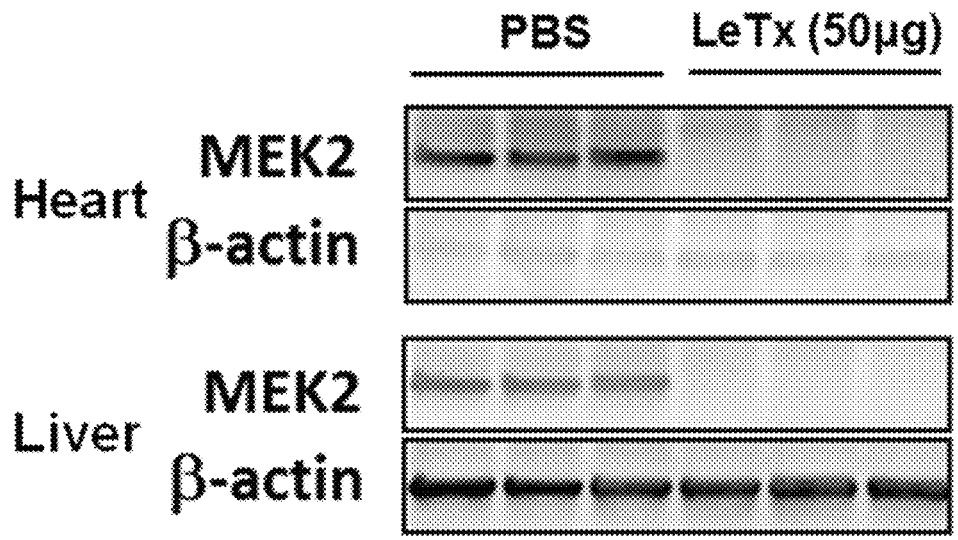

Anthrax LeTx induces liver toxicity. To examine the toxicity of LeTx in vivo, each C57BL/6J mouse (n=10) with PBS or different doses of LeTx (8.75, 12.5, 18.75, 25, or 50 μg/mouse) were injected. As shown in FIG. 4A, all mice died within 2-8 days except those treated with PBS or the lowest dose of LeTx (8.75 μg/mouse), suggesting that LeTx is toxic and lethal to mice in a dose-dependent manner. Because LeTx cleaves the N-terminal portion of MEK2, western blot analysis to detect MEK2 cleavage using an antibody against the N-terminus was performed (Arevalo et al., 2014). As shown in FIG. 4B, in the heart and liver samples isolated from mice that were challenged with LeTx for 24 h, the protein expression of cleaved MEK2 was absent in both tissues compared with those treated with PBS, suggesting that LeTx is biologically functional in vivo.

To further evaluate the effects of LeTx on liver function, the present inventors conducted blood chemistry analyses at 24 h post LeTx (50 μg/mouse) challenge. The results are shown in Table 1. For example, the most important liver injury biomarkers, AST and ALT, were both significantly higher in LeTx-treated mice than in PBS-treated animals (AST, 398.00±162.01 vs. 66.75±8.62; ALT, 172.50±40.12 vs. 42.75±8.88; P<0.01). By contrast, ALB, GLB, and total protein (TP), which are mainly synthesized in the liver, were found to be significantly lower in LeTx-challenged mice than in control mice. Furthermore, creatine phosphokinase (CPK), which is mainly found in the heart, brain, and skeletal muscle, and BUN in the renal panel were significantly elevated in LeTx-treated mice compared with control mice. These results demonstrate that LeTx induces liver injury in C57BL/6J mice, resulting in impaired biosynthesis and waste removal function.

Figure 5A:
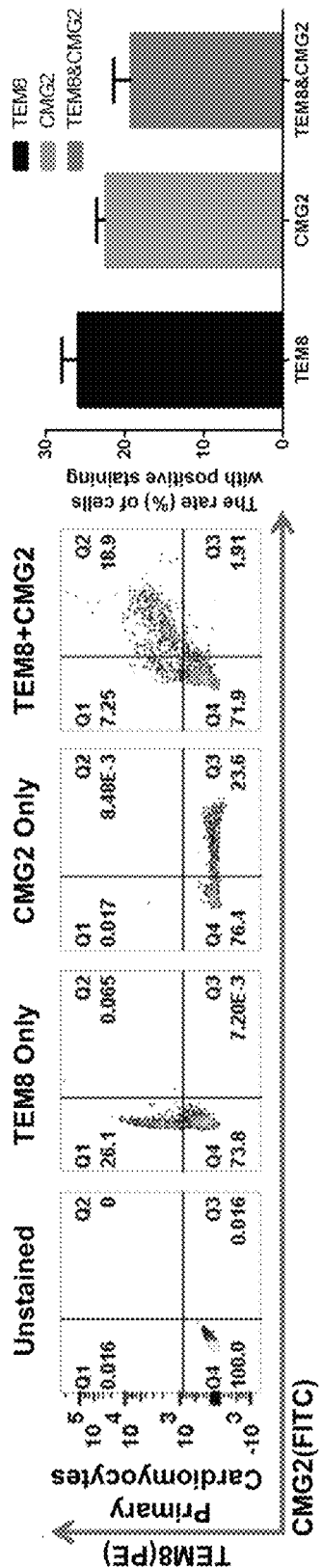
FIGS. 5A to 5F show that LeTx suppresses cell growth and induces cytotoxicity in vitro.

Anthrax toxin receptors are expressed in mouse heart tissues and primary cardiomyocytes. To confirm the existence of anthrax toxin receptors on the cell surface of cardiomyocytes, RT-PCR and flow cytometry analyses were performed using primary cardiomyocytes and heart tissues of Balb/c mice. As shown in FIG. 1G, both the Tem8 and Cmg2 transcripts were detectable in primary cardiomyocytes and heart tissues of Balb/c mice. Consistent with this, the results of flow cytometry also showed the presence of both TEM8 and CMG2 proteins on the surface of primary cardiomyocytes (FIGS. 2A and 5A). These results demonstrate the existence of anthrax toxin receptors on the cell surface of cardiomyocytes, which provide the necessary components for anthrax toxin delivery to the heart.

Figure 1H:
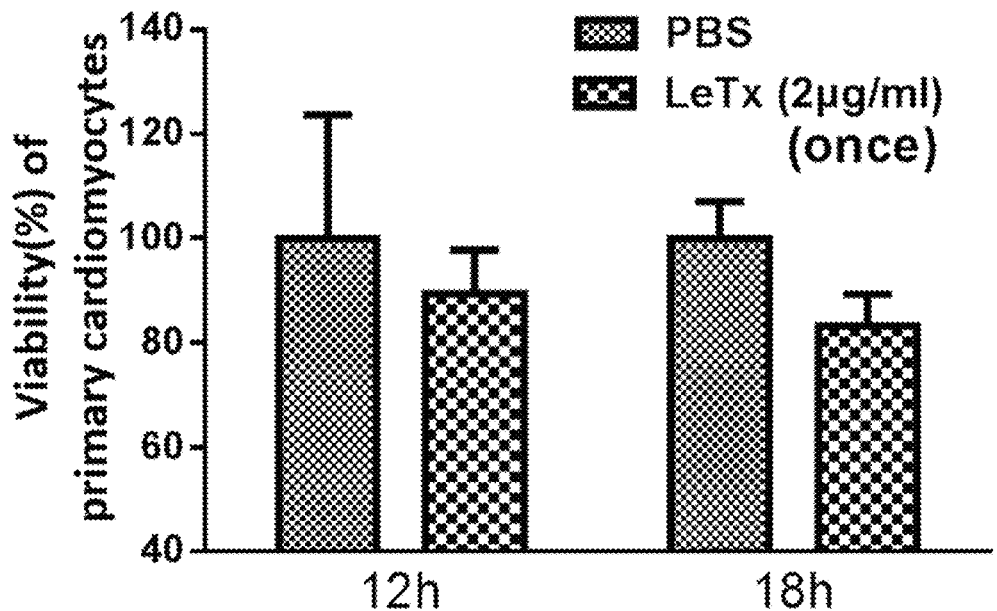
Figures 5B, 5C, 5D:
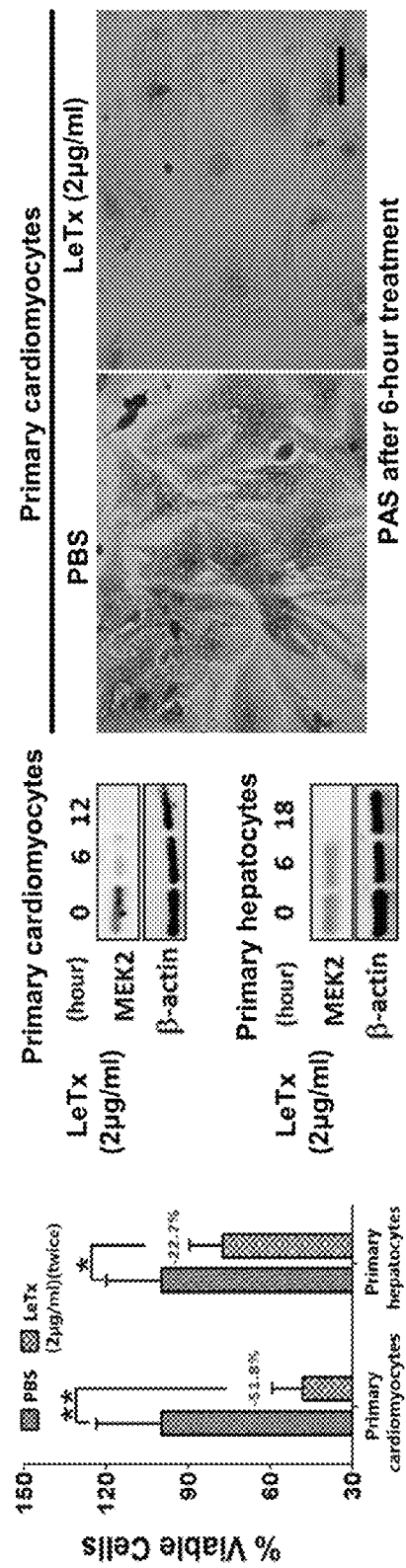
Figure 5E:
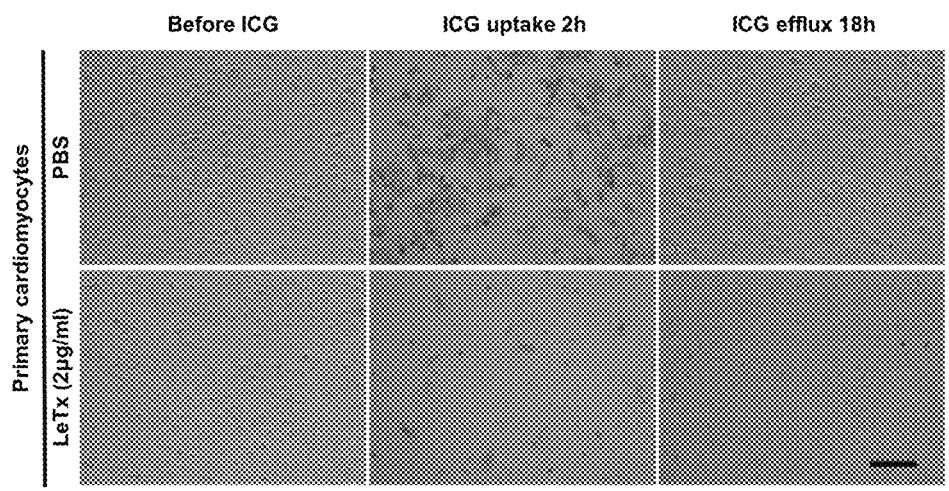
Figure 5F:
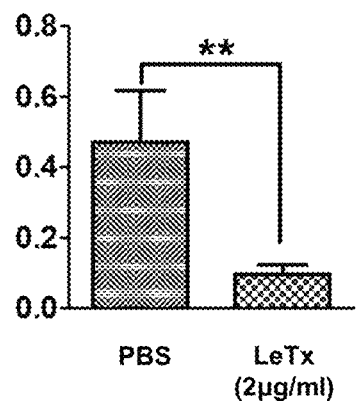

Anthrax LeTx suppresses cell growth and induces cytotoxicity in primary hepatocytes and primary cardiomyocytes in vitro. Next, the inventors determined whether anthrax LeTx is toxic to primary hepatocytes and primary cardiomyocytes in vitro using the MTT assay. As no useful data was obtained by treating cells with a single dose of LeTx (2 µg/mL) for 12 h or 18 h (FIG. 1H), two doses of LeTx (at 2 µg/mL) were administered, with an 18-h interval between doses. The results showed that, at 18 h after the second dose of LeTx, when compared with PBS-treated cells, the cell viabilities of primary cardiomyocytes and hepatocytes were significantly inhibited, by 51.8% (P<0.01, vs. control) and by 22.7% (P<0.05 vs. control), respectively, suggesting an inhibitory effect of LeTx on cell growth in vitro. To further investigate the effects of LeTx on cardiomyocyte and hepatocyte function involving the metabolism of diverse compounds, the present inventors performed the MEK2 cleavage assay, the ICG uptake-and-release assay, and the PAS staining assay in LeTx-treated cells. As shown in FIG. 5C, MEK2 was completely cleaved within 12 h and 18 h post-LeTx treatment (2 µg/mL) in primary cardiomyocytes and hepatocytes, respectively. The results of PAS staining showed that, after treating with LeTx (2 µg/mL) for 6 h, glycogen storage (fuchsia staining) in primary cardiomyocytes was dramatically decreased by nearly 90% compared with cells treated with PBS (FIG. 5D, 5F). In addition, the results of the ICG uptake-and-release assay demonstrated that LeTx-treated (at 4 µg/mL) primary cardiomyocytes had less ability to take up ICG than PBS-treated cells. Collectively, these results indicate that LeTx induces cytotoxicity in both primary hepatocytes and cardiomyocytes, leading to suppressed cell growth as well as impaired cell functions involving the metabolism of a variety of biological compounds.

Figure 6A:
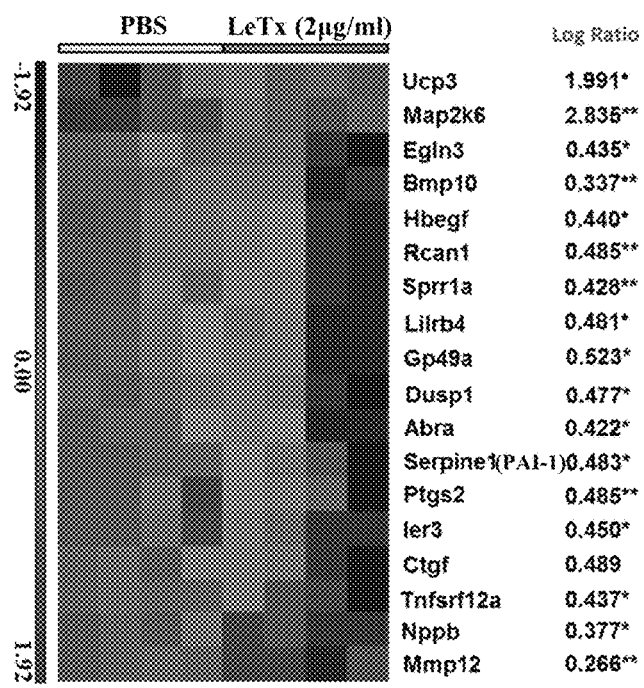
FIGS. 6A and 6B show the identification of LeTx-induced, cytotoxicity-related genes.
Figure 6B:
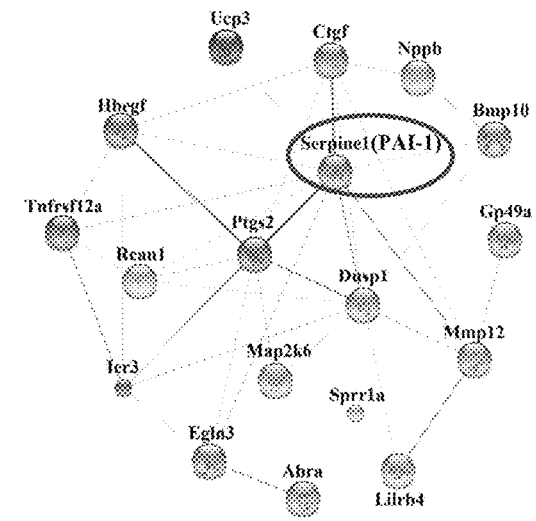

Anthrax LeTx-mediated effects on gene expression. To identify the genes that are potentially associated with the toxicity of LeTx in primary cardiomyocytes, a microarray assay was conducted using RNA samples isolated from primary cardiomyocytes exposed to either PBS or 2 µg/mL LeTx for 18 h. The microarray data had been submitted to GEO and the accession numbers is GSE116755. As shown in FIG. 6A, the expression of 18 genes (Abra, Bmp10, Ctgf, Dusp1, Egln3, Gp49a, Hbegf, Ier3, Lilrb4, Map2k6, Mmp12, Nppb, Ptgs2, Rcan1, Serpine1, Sprr1a, Tnfrsf12a, and Ucp3) was significantly changed (log ratio >1.8 or log ratio <0.56, P<0.05) in LeTx-treated cells compared with PBS-treated cells. A protein-protein network analysis was conducted using STRING 10 software, and the results demonstrated that these 18 genes were associated with MAPK, HIF-1, and TNF signaling pathways (FIG. 6B). Next, qPCR analyses were performed to verify the microarray results using the same RNA samples. The qPCR results are shown in Table 3 and are consistent with the microarray analysis. Moreover, the mRNA expression of these 18 genes was detected in LeTx-treated mouse hearts, primary hepatocytes, and mouse livers. As shown in Table 3, Map2k6 was the only gene that was significantly upregulated by LeTx at the transcriptional level in all cells and tissues. On the other hand, the mRNA expression of Gp49a, Hbegf, Lilrb4, and Tnfrsf12a was significantly downregulated by LeTx in all cells and tissues. Of note, the mRNA expression of three genes, Dusp1, Ier3, and Serpine1 (encoding PAI-1), was significantly lower in LeTx-treated primary cardiomyocytes than in PBS-treated cells, but notably upregulated in LeTx-treated mouse livers compared with the control group. Importantly, Serpine1 was the most significantly upregulated gene, whose mRNA level was dramatically increased (by 377-fold) by LeTx in mouse liver compared with the control group, which prompted us to further investigate its gene product (PAI-1) in subsequent experiments. Table 4 summarizes the LeTx-mediated effects on the expression of selected genes in mouse primary cardiomyocytes, HL-1 cells and mouse heart. The expression changes(log ratio) in comparison to the untreated controls are given(*P<0.05; **P<0.01).

TABLE 3

LeTx-mediated effects on the expression of selected genes in primary cardiomyocytes and primary hepatocytes as well as mouse hearts and livers.

| Gene name | Primary cardiomyocytes | | Mouse heart | Primary hepatocytes | Mouse liver |
|---|---|---|---|---|---|
| | Microarray | qPCR | qPCR | qPCR | qPCR |
| Mus musculus actin-binding Rho activating protein (Abra) | 0.422* | 0.282* | 0.678* | 1.251 | 1.003 |
| Mus musculus bone morphogenetic protein 10 (Bmp10) | 0.337** | 0.278** | 0.280 | 1.408 | 0.421** |
| Mus musculus connective tissue growth factor (Ctgf) | 0.489* | 0.339** | 0.378** | 0.467* | 0.763 |
| Mus musculus dual specificity phosphatase 1 (Dusp1) | 0.477* | 0.392* | 0.496** | 0.481* | 3.282** |
| Mus musculus egl-9 family hypoxia-inducible factor 3 (Egln3) | 0.435* | 0.500** | 0.568** | 1.528 | 1.451 |
| Mus musculus glycoprotein 49 A (Gp49a), transcript variant 1 | 0.523* | 0.367* | 0.371** | 0.145** | 0.425* |
| Mus musculus heparin-binding EGF-like growth factor (Hbegf) | 0.440* | 0.404* | 0.497* | 0.476* | 0.410** |
| Mus musculus immediate early response 3 (Ier3) | 0.450* | 0.409* | 0.480* | 0.499** | 7.247** |
| Mus musculus leukocyte immunoglobulin-like receptor, subfamily B, member 4 (Lilrb4) | 0.481* | 0.469* | 0.186** | 0.046* | 0.201* |
| Mus musculus mitogen-activated protein kinase kinase 6 (Map2k6) | 2.835** | 5.554** | 4.069** | 2.174* | 4.121** |
| Mus musculus matrix metallopeptidase 12 (Mmp12) | 0.266** | 0.414* | 1.533 | 2.155 | 1.3340 |
| Mus musculus natriuretic peptide type B (Nppb), transcript variant 2 | 0.377* | 0.240** | 0.008** | 0.233* | 1.179 |
| Mus musculus prostaglandin-endoperoxide synthase 2 (Ptgs2) | 0.485** | 0.301* | 0.647 | 0.996 | 0.937 |
| Mus musculus regulator of calcineurin 1 (Rcan1), transcript variant 1 | 0.485** | 0.350** | 0.425** | 1.252 | 0.298** |

TABLE 3-continued

LeTx-mediated effects on the expression of selected genes in primary cardiomyocytes and primary hepatocytes as well as mouse hearts and livers.

| Gene name | Primary cardiomyocytes | | Mouse heart | Primary hepatocytes | Mouse liver |
|---|---|---|---|---|---|
| | Microarray | qPCR | qPCR | qPCR | qPCR |
| *Mus musculus* serine (or cysteine) peptidase inhibitor, clade E, member 1 (Serpine1) | 0.483* | 0.423* | 0.389* | 0.580 | 327.778** |
| *Mus musculus* small proline-rich protein 1A (Sprr1a) | 0.428** | 0.331* | 0.597 | 0.132** | 0.344* |
| *Mus musculus* tumor necrosis factor receptor superfamily, member 12a (Tnfrsf12a), transcript variant 2 | 0.437* | 0.480* | 0.119** | 0.401** | 0.397* |
| *Mus musculus* uncoupling protein 3 (mitochondrial, proton carrier) (Ucp3) | 1.911* | 3.723* | 4.636* | 2.891 | 0.518 |

*$P < 0.05$ and **$P < 0.01$ versus the PBS-treated group.

TABLE 4

LeTx-mediated effects on the expression of selected genes in mouse primary cardiomyocytes, HL-1 cells and mouse heart. The expression changes (log ratio) in comparison to the untreated controls are given (*$P < 0.05$; **$P < 0.01$)

| Gene name | Genebank ID | Mouse primary cardiomyocytes | | HL-1 | Mouse heart |
|---|---|---|---|---|---|
| | | Microarray | qPCR | qPCR | qPCR |
| *Mus musculus* actin-binding Rho activating protein (Abra), mRNA | NM_175456 | 0.422* | 0.282* | 0.776 | 0.678* |
| *Mus musculus* bone morphogenetic protein 10 (Bmp10), mRNA | NM_009756 | 0.337** | 0.278** | 0.847 | 0.280** |
| *Mus musculus* connective tissue growth factor (Ctgf), mRNA | NM_010217 | 0.489* | 0.339** | 0.858 | 0.378** |
| *Mus musculus* dual specificity phosphatase 1 (Dusp1), mRNA | NM_013642 | 0.477* | 0.392* | 0.461* | 0.496** |
| *Mus musculus* egl-9 family hypoxia-inducible factor 3 (Egln3), mRNA | NM_028133 | 0.435* | 0.500** | 0.487* | 0.568** |
| *Mus musculus* glycoprotein 49 A (Gp49a), transcript variant 1, mRNA | NM_008147 | 0.523* | 0.367* | 0.912 | 0.371** |
| *Mus musculus* heparin-binding EGF-like growth factor (Hbegf), mRNA | NM_010415 | 0.440* | 0.404* | 0.433** | 0.497* |
| *Mus musculus* immediate early response 3 (Ier3), mRNA | NM_133662 | 0.450* | 0.409* | 1.395 | 0.480* |
| *Mus musculus* leukocyte immunoglobulin-like receptor, subfamily B, member 4 (Lilrb4), transcript variant 1, mRNA | NM_013532 | 0.481* | 0.469* | 0.879 | 0.186** |
| *Mus musculus* mitogen-activated protein kinase kinase 6 (Map2k6), mRNA | NM_011943 | 2.835** | 5.554** | 2.291* | 4.069** |
| *Mus musculus* matrix metallopeptidase 12 (Mmp12), mRNA | NM_008605 | 0.266** | 0.414* | 1.015 | 1.533 |
| *Mus musculus* natriuretic peptide type B (Nppb), transcript variant 2, mRNA | NM_001287348 | 0.377 | 0.240** | 0.020** | 0.008** |
| *Mus musculus* prostaglandin-endoperoxide synthase 2 (Ptgs2), mRNA | NM_011198 | 0.485** | 0.301* | 0.884 | 0.647 |
| *Mus musculus* regulator of calcineurin 1 (Rcan1), transcript variant 1, mRNA | NM_001081549 | 0.485** | 0.350** | 0.430** | 0.425** |
| *Mus musculus* serine (or cysteine) peptidase inhibitor, clade E, member 1 (Serpine1), mRNA | NM_008871 | 0.483* | 0.423* | 1.019 | 0.389* |
| *Mus musculus* small proline-rich protein 1A (Sprr1a), mRNA | NM_009264 | 0.428** | 0.331* | 0.445** | 0.597 |
| *Mus musculus* tumor necrosis factor receptor superfamily, member 12a (Tnfrsf12a), transcript variant 2, mRNA | NM_001161746 | 0.437 | 0.480* | 0.162** | 0.119** |
| *Mus musculus* uncoupling protein 3 (mitochondrial, proton carrier) (Ucp3), mRNA | NM_009464 | 1.911 | 3.723* | 1.016 | 4.636* |
| *Mus musculus* a disintegrin-like and metallopeptidase (reprolysin type) with thrombospondin type 1 motif, 8 (Adamts8), mRNA | NM_013906 | 0.545* | | | |
| *Mus musculus* predicted gene 12409 (Gm12409), long non-coding RNA | NR_046068 | 1.970* | | | |
| *Mus musculus* keratin 18 (Krt18), mRNA | NM_010664 | 0.552** | | | |
| *Mus musculus* mesoderm specific transcript (Mest), transcript variant 1, mRNA | NM_001252292 | 0.520** | | | |
| *Mus musculus* microRNA 181b-2 (Mir181b-2), microRNA | NR_029904 | 1.871* | | | |
| *Mus musculus* serine (or cysteine) peptidase inhibitor, clade B, member 1a (Serpinb1a) | NM_025429 | 0.532* | | | |
| *Mus musculus* solute carrier family 38, member 2 (Slc38a2), mRNA | NM_175121 | 0.539* | | | |
| *Mus musculus* signal peptidase complex subunit 3 homolog (*S. cerevisiae*) (Spcs3), mRNA | NM_029701 | 0.535* | | | |
| Unknown (26) not show | | | | | |

Figure 4C:
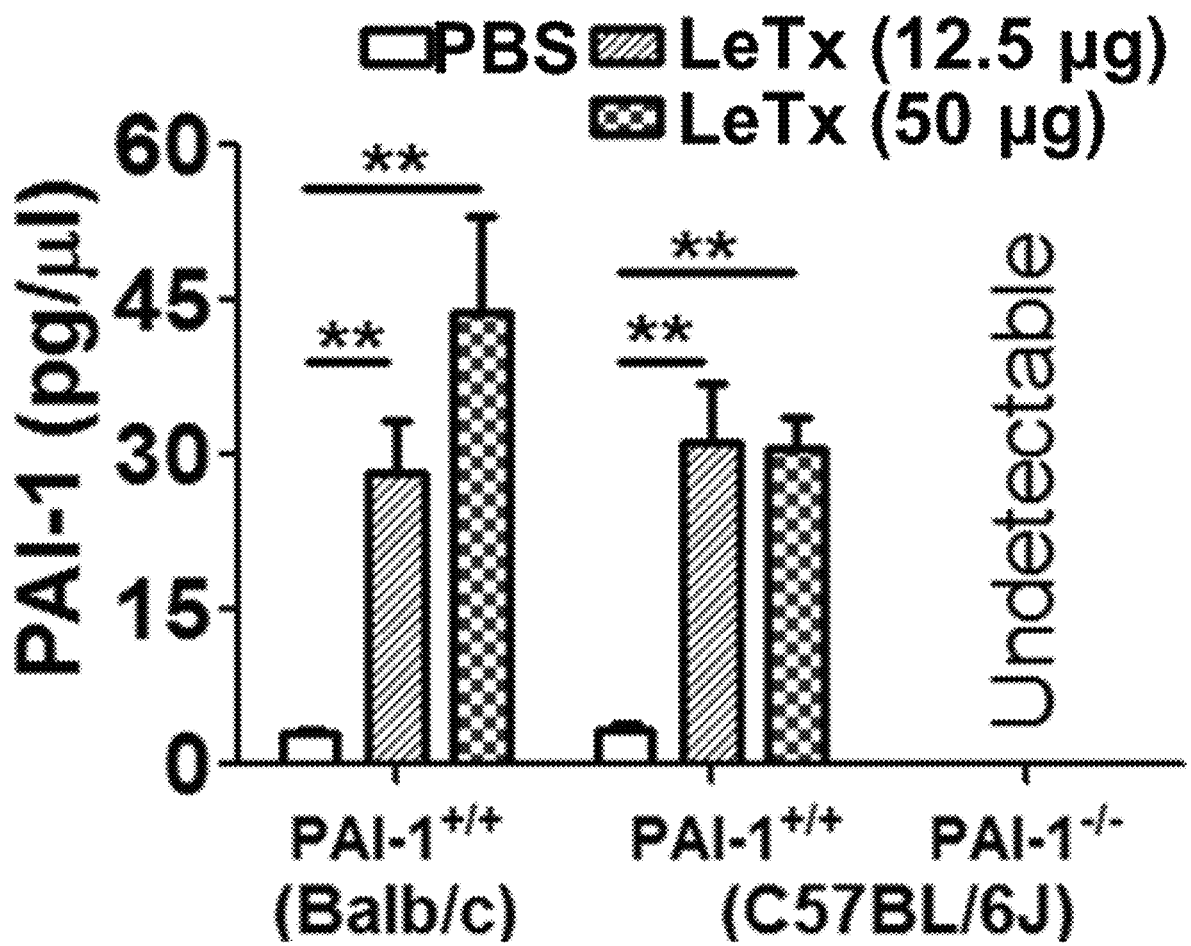
Figure 4D:
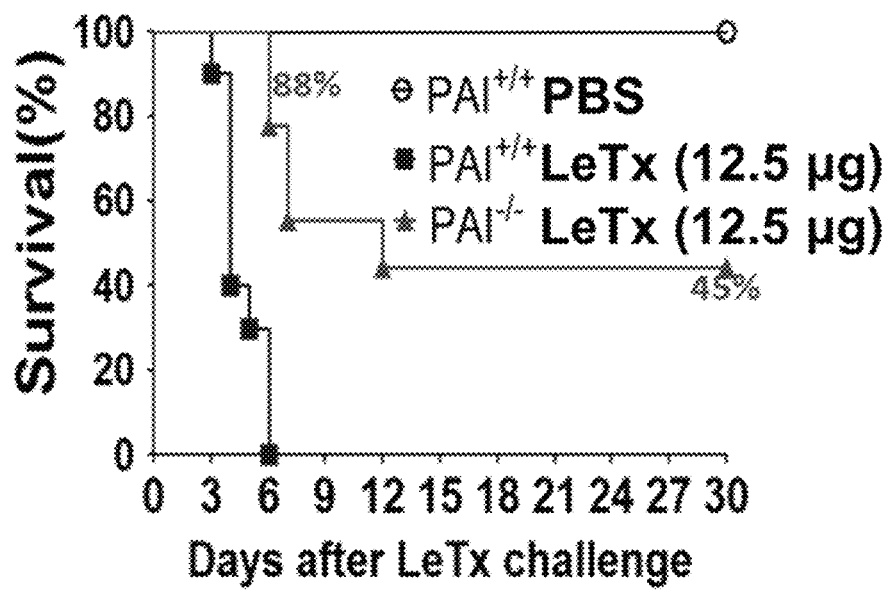
Figure 4E:
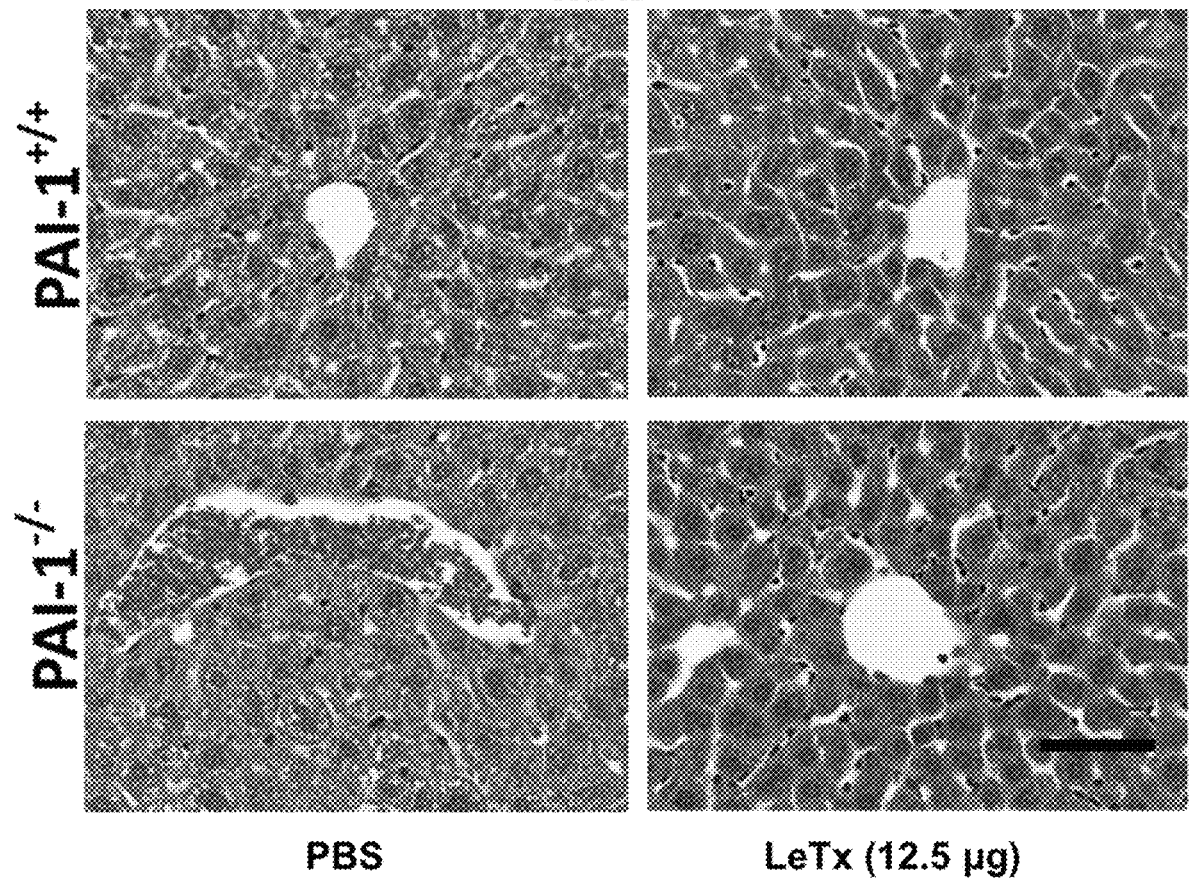

PAI-1$^{-/-}$ mice are more tolerant to LeTx than WT mice. Since Serpine1 was the most significantly upregulated gene among the 18 genes associated with LeTx-induced toxicity in mouse livers (Table 3), the inventors sought to measure the serum level of its gene product (PAI-1) in mice treated with PBS or LeTx using ELISA. As shown in FIG. 4C, the level of PAI-1 in mouse sera was significantly increased to 28.25±5.50 and 43.87±9.39 pg/µl after challenges with 12.5 and 50 µg of LeTx, respectively, in Balb/c mice compared with 3.14±0.16 pg/µl in control mice (P<0.01). Similar results were also observed in WT C57BL/6J mice. In addition, after treating with 12.5 µg of LeTx, all the WT C57BL/6J mice died within 6 days, whereas 88% of the PAI-1$^{-/-}$ C57BL/6J mice survived (FIG. 4D), suggesting that PAI-1 is associated with LeTx-induced toxicity in mice. However, the inventors also observed that neither WT and PAI-1$^{-/-}$ mice survived a higher dose of LeTx (50 µg) and died within 1 week post-administration (data not show), suggesting other possible mechanisms underlying LeTx-induced toxicity. To further investigate the role of PAI-1 in LeTx-treated mice, the inventors performed histological analyses in mouse livers using H&E staining. As shown in FIG. 4E, morphological manifestations, such as anisonucleosis (variation in the size of the cell nuclei) and centrilobular congestion, were observed in the livers of WT mice treated with 12.5 µg LeTx but not in the livers of PAI-1$^{-/-}$ mice, which indicates that PAI-1$^{-/-}$ mice are more tolerant of LeTx than WT mice.

The present inventors studied the effects of EdTx and LeTx on liver and heart functions, respectively, and to identify the signaling pathways and genes that are associated with EdTx- and LeTx-induced injury and mortality, that provide potential therapeutic targets for anthrax treatment.

The membrane-permeant dye JC-1 is widely used in apoptosis studies to evaluate mitochondrial membrane potential and health (Lugli et al., 2005). These results demonstrated that EdTx and LeTx have significant inhibitory effects on the growth of primary hepatocytes and cardiomyocytes, respectively (FIGS. 2A-H and 5A-F). This growth inhibition may have been due to induction of cytotoxicity and cell apoptosis, as evidenced by changes in mitochondrial membrane potential. In the animal study, intravenous administration of 20 µg of EdTx led to liver damage and mortality in A/J mice within 48 h. This dose is 15 µg lower than that used by Liu et al. in C57BL/6J mice (35 µg is of EdTx per mouse, intravenously). This discrepancy is possibly because the A/J mouse is one of the most susceptible mouse strains to anthrax toxins, whereas C57BL/6J strain is the least susceptible (Welkos et al., 1986).

The inventors evaluated liver function by measuring the levels of a number of biochemical indicators in mouse sera (Table 1). For example, ALT and AST were significantly increased by anthrax toxins, which indicates impaired liver function, as ALT and AST are considered to be major biomarkers of liver function. In addition, elevation of ALP suggests bile flow problems caused by liver damage. ALB and GLB, which are mainly synthesized in the liver, were found significantly decreased by EdTx, suggesting the loss of normal liver function. To the inventors' knowledge, these findings have not been reported in previous studies (Liu et al., 2013). Moreover, significant increases in renal function markers, such as BUN, CREA, and phosphorous, were also observed in this study, which is consistent with previous reports that EdTx may cause kidney lesions (Sastalla et al., 2012) and kidney function deterioration (Firoved et al., 2005; Jaswal et al., 2017). Further investigation is required to reveal the underlying mechanisms of EdTx-mediated kidney damage. Considering the fact that the ICG uptake-and-efflux assay is used to evaluate liver function clinically (Faybik and Hetz, 2006), the inventors conducted this assay to further evaluate the effects of anthrax toxins on hepatocytes and cardiomyocytes. These findings demonstrated that EdTx-/LeTx-treated primary hepatocytes/cardiomyocytes showed significantly reduced ICG uptake and efflux (FIGS. 2 and 5). Of note, ICG was removed from hepatocytes along with bile acid excretion. Reduced ICG efflux suggests a reduction of bile flow, which is possibly due to a decline of the functional bile canaliculi caused by anthrax toxins, resulting in an impaired detoxification process in the cells. In addition, LeTx affects the function of primary hepatocytes and cardiomyocytes in accelerating the lysis of glycogen.

To identify potential therapeutic targets against anthrax toxins, microarray analysis and subsequent protein-protein network analysis were applied in this study using RNA samples isolated from anthrax toxin-treated mouse livers. A panel of genes associated with anthrax toxin-induced organ damage were identified and further confirmed by real-time qPCR (FIGS. 3A-D and 6A-B). These genes are involved in various signaling pathways, including amino acid metabolism, glucose metabolism, inflammation, and apoptosis, which requires further investigation.

Figure 7:
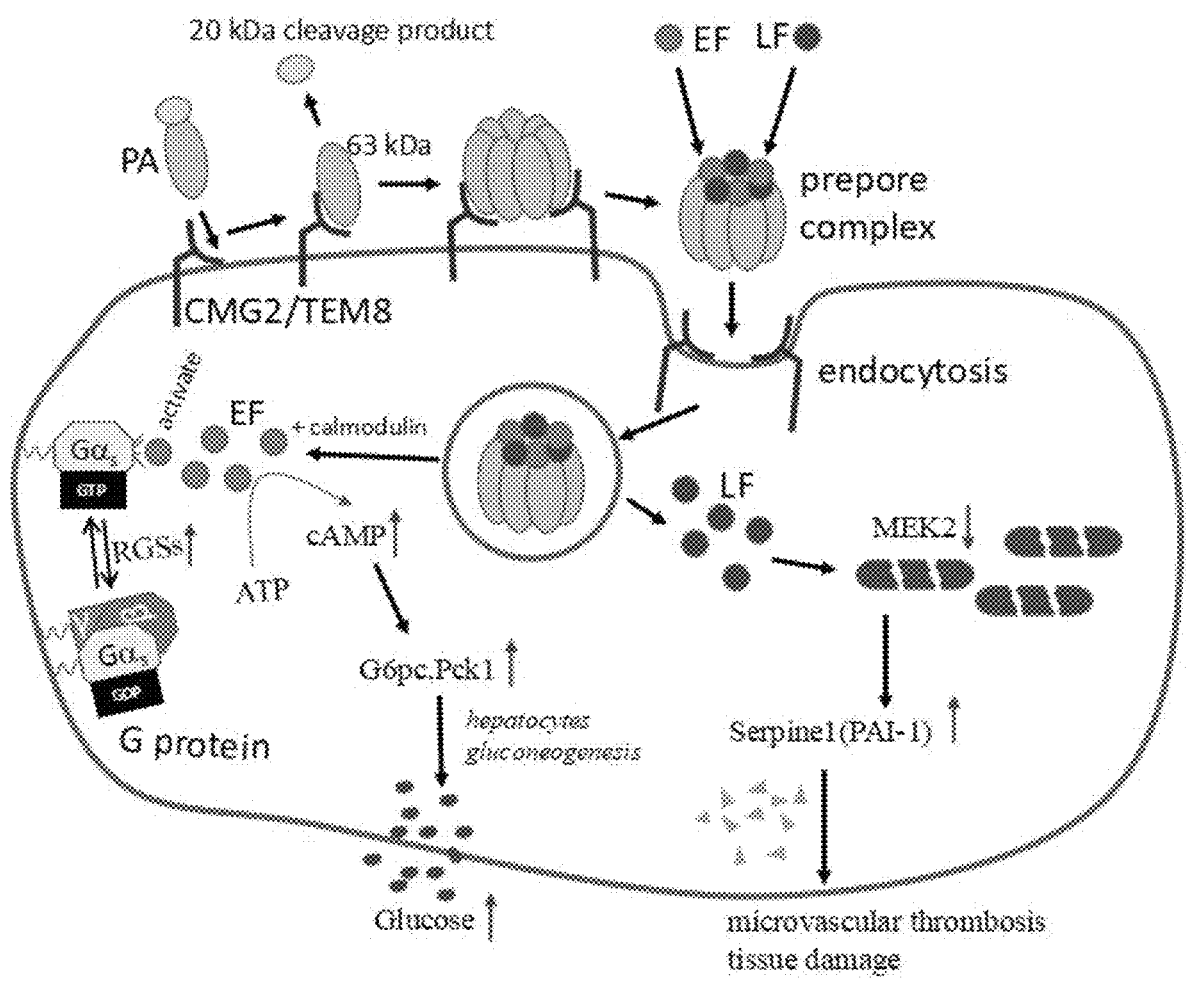
FIG. 7 highlights of anthrax toxin-induced cytotoxicity in hepatocytes and cardiomyocytes. EdTx consists of EF, a calmodulin-dependent adenylate cyclase that is activated by a GTP-bound Gα subunit. The regulators of G protein signaling (RGSs) are crucial regulatory molecules that influence the nucleotide-bound state of Gα subunits and act as GTPase-activating proteins. The Gα-RGS complex increases the rates of intrinsic GTP hydrolysis to GDP, then EdTx can be activated to convert intracellular ATP to cAMP, resulting in a dramatic increase in cAMP level. On the other hand, G6pc and Pck1 participate in the regulation of hepatic gluconeogenesis and the liver breaks down glycogen to produce blood glucose in a short period of time when exposed to EdTx. High level of PAI-1 (a serpin protein)—a risk factor for thrombosis and atherosclerosis, in the liver and serum is highly implicated in LeTx-induced cytotoxicity by our study. EF, edema factor; LF, lethal factor; PA, protective antigen; CMG2/TEM8, membrane receptor proteins for PA binding.

Like many other infectious diseases, such as influenza, cholera, and Ebola, anthrax can increase the concentration of blood glucose (Arsand et al., 2005), although, the mechanism is unclear. The inventors found that, in EdTx-treated A/J mice but not in LeTx-treated mice, the level of blood glucose was elevated immediately by EdTx, peaked at 3 h after EdTx administration, and declined thereafter but remained higher than the control group until 9 h after administration (FIGS. 1A-F). These findings suggest that the liver breaks down glycogen in a short period of time when exposed to EdTx, as the liver is the major site of endogenous glucose production (Mutel et al., 2011) and stores glycogen to supply the body with glucose when required (Bhattacharya, 2015). Intriguingly, the expression of G6pc, Pck1, and Ski1 was found to be upregulated in primary hepatocytes and livers in the present study. G6pc is a member of the glucose-6-phosphatase system, while Pck1 plays an important role in gluconeogenesis and stimulates hepatic glucose production (Mithieux et al., 2004; Oh et al., 2013). Both genes are involved in the LKB1-SIK pathway, which participates in the regulation of hepatic gluconeogenesis (Patel et al., 2014). Therefore, EdTx may enhance gluconeogenesis and glycogenolysis via the LKB1-SIK pathway at the early stages of anthrax disease, leading to a prompt rise in blood glucose level (FIG. 7).

It has been reported that EdTx-mediated effects increase the demand for intracellular calcium, leading to a decrease in calcium within the peripheral circulation. The expression of Ramp3, which is known to respond to changes in the extracellular calcium concentration and play a crucial role in calcium homeostasis, is upregulated in this process (Bouschet et al., 2005). This is consistent with the inventors' finding that Ramp3 is upregulated in EdTx-treated mouse liver (FIGS. 3A-D). On the other hand, EdTx consists of EF, a calmodulin-dependent adenylate cyclase that is activated by a GTP-bound Gα subunit (Dal Molin et al., 2008; Lubker et al., 2015). The regulators of G protein signaling (RGSs) are crucial regulatory molecules that influence the nucleotide-bound state of Gα subunits and act as GTPase-activating proteins (Croft et al., 2013; De Vries et al., 2000; Denecke et al., 1999; Han et al., 2006). The Gα-RGS complex increases the rates of intrinsic GTP hydrolysis to GDP by up to 2000-fold (Hepler, 1999). In this study, the expression levels of both Rgs1 and Rgs2 were significantly increased by EdTx in primary hepatocytes and liver tissues (FIGS. 3A-D), which suggests that EdTx can be activated to convert intracellular ATP to cAMP, resulting in a dramatic increase in cAMP level, as observed in the animal model (FIGS. 1A-F and 7). Consistent with this suggestion, knockdown of RGS1 significantly inhibits the cAMP increase induced by EdTx (FIGS. 3A-D), which further reveals the association of RGSs with EdTx-induced cytotoxicity. In addition, an increased level of cAMP is associated with clinical situations that predispose to infections, and disruption of cAMP generation is a promising therapeutic strategy against these diseases (Gille et al., 2004; Serezani et al., 2008). The Ramp3, Pck1, G6pc, Rgs1, Fos, Fosl2, Hcar2, Cxcl2, and Cxcl3 genes analyzed in this study are associated with cAMP production. These findings demonstrated that knockdown of these genes individually or in combination protected primary hepatocytes against EdTx-mediated elevation of cAMP level, which suggests that these genes are potential therapeutic targets against anthrax and other infectious diseases.

The previous study reported that knockdown of the anthrax toxin receptor Cmg2 results in protection against the increase of intracellular cAMP induced by EdTx (Arevalo et al., 2014). The inventors found that, in addition to Cmg2, Rgs1, Hcar2, Fosl2, Hcar2, Cxcl2, and Cxcl3 are also promising targets against cytotoxicity of EdTx. Extensive studies in vivo are required in order to evaluate these genes as gene therapy targets and to develop anti-EdTx drugs or vaccines.

Moreover, the inventors found that the mechanism by which LeTx damages liver function was different from that of EdTx. High levels of PAI-1 (also known as SERPINE1) in the liver and serum were highly implicated in LeTx damage by this study. PAI-1 is a serine protease inhibitor (serpin) that functions as the principal inhibitor of tissue plasminogen activator (tPA) and urokinase (uPA), the activators of plasminogen and hence fibrinolysis (the physiological breakdown of blood clots). PAI-1 is a serpin protein and a risk factor for thrombosis and atherosclerosis (Dostalova et al., 2017) (FIG. 7). Under inflammatory conditions, in which fibrin is deposited in tissues, PAI-1 appears to play a significant role in the progression to fibrosis (the pathological formation of connective tissue). Presumably, lower PAI-1 levels would lead to less suppression of fibrinolysis and conversely a more rapid degradation of fibrin (Flevaris and Vaughan, 2017). Previous studies reported that PAI-1 deficiency was characterized by mild-to-moderate bleeding (Heiman et al., 1993) and that PAI-1 deficiency markedly reduces pulmonary fibrin deposition and greatly reduces inflammation and injury without impacting upstream coagulation (Poole et al., 2017). PAI-$1^{-/-}$ mice are more tolerant to LeTx than WT mice at the early stages of LeTx challenge, and high levels of PAI-1 in liver indicated that PAI-1 plays an important role in liver injury. Serpine1 (encoding PAI-1) is a potential target gene for silencing to help in protecting the host against LeTx at the early stage of infection.

Preparation of EdTx and LeTx. EdTx (EF plus PA) and LeTx (LF plus PA) solutions in this study were prepared by dissolving recombinant EF (NR-13413, BEI Resources, Manassas, VA) and LF (NR-4368, BEI Resources) in culture medium and incubating for 10 min, followed by mixing with a double quantity of recombinant PA (NR-3780, BEI Resources) and incubating for an additional 10 min.

Animal studies. All animal studies were carried out using the same number of male and female mice whenever was possible in accordance with the protocols approved by the Animal Care and Use Committee of Texas Tech University Health Science Center. In the EdTx challenge experiments, 6-8-week-old A/J mice were randomly divided into three groups. Each mouse was injected with 20 μg or 40 μg EdTx (a combination of EF plus PA at 1:2) in 0.1 mL of PBS or PBS only. The animal experiment flow chart is shown in FIG. 1A. In the LeTx challenge experiments, 6-8-week-old C57BL/6J mice were randomly divided into 6 groups. Each mouse was intravenously injected with 8.75, 12.5, 18.75, 25, or 50 μg LeTx (a combination of LF plus PA at 1:2) in 0.2 mL PBS or PBS only. Five-to-six-week-old PAI-1 knockout (PAI-$1^{-/-}$) C57BL/6J mice were purchased from the Jackson Laboratory and intravenously injected with PBS or LeTx, as indicated. All mice were monitored after injection for signs of malaise or mortality until the end of experiments.

Cell culture. Primary cardiomyocytes were isolated from 1-3-day-old neonatal Balb/c mice using the Pierce Primary Cardiomyocyte Isolation Kit (Thermo Fisher Scientific, Grand Island, NY) following the manufacture's protocol. Primary hepatocytes were isolated from 1-3-day-old neonatal A/J mice as described by Edwards et al. with some modifications (Bai et al., 2014; Edwards et al., 2013; Houseman et al., 2015). Briefly, cell culture plates were coated with 0.01% gelatin and incubated at 37° C. for 24 h prior to isolation. The livers were removed from the neonatal mice and cut into pieces of 1 $mm^3$, followed by washing with Hank's balanced salt solution (HBSS, Thermo Fisher Scientific, Grand Island, NY), containing 3 mM $CaCl_2$ (Sigma-Aldrich, St. Louis, MO). An equal volume of collagenase H (Roche Life Science, Indianapolis, IN) was added to the solution to a final concentration of 0.08 U. After incubation at 37° C. in a water bath shaker (~80 rpm) for 1 h, the liver pieces were washed with ice-cold hepatocyte wash medium (William's E Medium; Thermo Fisher Scientific), containing 12% heat-inactivated FBS (Thermo Fisher Scientific), 0.02 VL insulin-transferrin-sodium selenite media supplement (Sigma-Aldrich), 30 mM sodium pyruvate (Sigma-Aldrich), 100 U/ml penicillin, and 100 μg/ml streptomycin. The tissues were broken up, and the cell suspension was filtered through a 70-μm nylon cell strainer, followed by centrifugation at 50 x g for 2 min at 4° C. The supernatant was decanted, and the cells were gently suspended in 20 mL of ice-cold hepatocyte wash medium. The centrifugation-and-resuspension step was repeated twice. The cells were then counted with a hemocytometer using the trypan blue method and seeded at a density of $1.5\times10^6$ cells/well in a 6-well plate, $8\times10^5$ cells/well in a 12-well plate, and $5\times10^5$ cells/well in a 24-well plate. The cells were maintained in hepatocyte culture medium (hepatocyte wash medium supplemented with 5 nM dexamethasone from Sigma-Aldrich and growth factors from human hepatocardinoma culture medium) and incubated at 37° C. in a humidified atmosphere of 5% $CO_2$. The culture medium was changed every 2 days.

Survival analysis. Ten mice from each group were randomly selected for Kaplan-Meier survival analysis, and survival curves were plotted.

Blood glucose test. Blood was drawn from the tail veins of 10 randomly selected mice from each group at 0, 3, 6, 9, 12, 24, 30, and 36 h after PBS or EdTx injection and was used for a blood glucose test using a glucose meter (Henry Schein Inc., Melville, NY).

cAMP-specific ELISA. In the animal study, 15 mice from each group were randomly selected for measurement of cAMP levels in serum and liver. Briefly, blood and livers were collected at 0, 6, 12, 24, and 36 h after injection. The blood samples were centrifuged at 3000× g for 10 min to collect the serum. Liver samples (100 mg) were immediately frozen in liquid nitrogen after collection and then ground with a stainless steel mortar and pestle into a fine powder. The cAMP concentration in serum and liver was measured using a cAMP ELISA kit (Enzo Life Sciences, Farmingdale, NY, USA) following the manufacturer's instructions.

For the in vitro study, primary hepatocytes were cultured in a 12-well plate at a density of $3 \times 10^5$ cells/well and grown overnight. Cells were then treated with 0, 0.25, 0.5, 1, 2, or 4 μg/ml EdTx, followed by lysis with 0.5 ml of 0.1 M HCl at 0, 0.25, 0.5, 1, 2, 4, 6, 8, 16, or 24 h post-treatment for 10 min. The cAMP concentrations in the cell lysates were measured using a cAMP ELISA kit (Enzo Life Sciences, Farmingdale, NY, USA) as previously described [3].

PAI-1 (also known as SERPINE1) ELISA. Balb/c (PAI-$1^{+/-}$, n=5), C57BL/6J (wild type, PAI-$1^{+/+}$, n=5), and PAI-$1^{-/-}$ (n=5) mice were challenged intravenously with 50 μg of LeTx in 0.2 ml PBS. Blood samples were collected at 24 h post-injection. The level of PAI-1 in mouse serum was measured using the Mouse PAI-1 (SERPINE1) ELISA Kit (Thermo Fisher Scientific) according to the manufacturer's protocol.

Flow cytometric detection of anthrax toxin receptors. Primary hepatocytes and cardiomyocytes were collected and washed with PBS containing 2% FBS for fluorescence-activated cell sorting (FACS). Cells were stained with primary rabbit polyclonal anti-TEM8 antibodies (Abcam, Cambridge, MA) with secondary donkey anti-rabbit IgG PE (Affymetrix eBioscience, San Diego, CA) and/or primary goat polyclonal anti-CMG2 (Abcam) with secondary chicken anti-goat Alexa Fluor 488 antibodies (Thermo Fisher Scientific). Data were analyzed with a BD FACS Canto™ II flow cytometer (BD Biosciences, San Jose, CA) using Flow Jo version 7.6.5 or version X.0.6 software (Tree Star, Ashland, OR).

siRNA transfections. siRNAs targeting the murine Ramp3 (si-Ramp3), Rgs1 (si-Rgs1), Pck1(si-Pck1), G6pc (si-G6pc), Hcar2 (si-Hcar2), Fosl2 (si-Fosl2), Fos (si-Fos), Cxcl2 (si-Cxcl2), Cxcl3 (si-Cxcl3), and Cmg2 (si-CMG2) genes were purchased from Santa Cruz Biotechnology. The sequence information is shown in Table 5. si-GFP was used as a nonspecific control (Arevalo et al., 2014). Primary hepatocytes were seeded in 24-well plates at a density of $1.5 \times 10^5$ cells/well in 0.3 ml of Opti-MEM® medium (Thermo Fisher Scientific) and grown for 5-7 days prior to transient transfection with 50 pmol siRNA using Lipofectamine RNAiMax reagent (Thermo Fisher Scientific) following the manufacturer's protocol. The cells were then incubated for 48 h and transfected again, followed by an additional incubation of 48 h.

TABLE 5

Sequence information of siRNA used in this study (SEQ ID NOS: 1-58).

| Name | Catalog no. | Duplexe | | Sequences | SEQ ID NO: |
|---|---|---|---|---|---|
| RAMP3 siRNA(m) | SC-40897 | A | Sense | GGUUCAGAUUGUCCAUACUtt | 1 |
| | | | Antisense | AGUAUGGACAAUCUGAACCtt | 2 |
| | | B | Sense | CUGAGCACAUCAUUUAUCAtt | 3 |
| | | | Antisense | UGAUAAAUGAUGUGCUCAGtt | 4 |
| | | C | Sense | CUCUGUGAUCUGUCACGAUtt | 5 |
| | | | Antisense | AUCGUGACAGAUCACAGAGtt | 6 |
| RGS1 siRNA(m) | SC-36409 | A | Sense | GACUCAGAAAGGAUUAACAtt | 7 |
| | | | Antisense | UGUUAAUCCUUUCUGAGUCtt | 8 |
| | | B | Sense | GGAAGCAUGAACAAGAAGAtt | 9 |
| | | | Antisense | UCUUCUUGUUCAUGCUUCCtt | 10 |
| | | C | Sense | GAAGCAUGAACAAGAAGAAtt | 11 |
| | | | Antisense | UUCUUCUUGUUCAUGCUUCtt | 12 |
| PCK1 siRNA(m) | SC-76107 | A | Sense | CCAUGUAUGUCAUCCCAUUtt | 13 |
| | | | Antisense | AAUGGGAUGACAUACAUGGtt | 14 |
| | | B | Sense | GCAACUUAAGGGCUAUCAAtt | 15 |
| | | | Antisense | UUGAUAGCCCUUAAGUUGCtt | 16 |
| | | C | Sense | CAGAAGGAGUACCCAUUGAtt | 17 |
| | | | Antisense | UCAAUGGGUACUCCUUCUGtt | 18 |
| G6PC siRNA(m) | SC-145294 | A | Sense | CAUGCAGAGUCUUUGGUAUtt | 19 |
| | | | Antisense | AUACCAAAGACUCUGCAUGtt | 20 |
| | | B | Sense | GCAAACCAGAUGCAAUCUAtt | 21 |
| | | | Antisense | UAGAUUGCAUCUGGUUUGCtt | 22 |
| | | C | Sense | CUCUAUCACGUCACAGUUUtt | 23 |
| | | | Antisense | AAACUGUGACGUGAUAGAGtt | 24 |
| HCAR2 siRNA(m) | SC-60793 | A | Sense | CACACCACUUCUUGAACAAtt | 25 |
| | | | Antisense | UUGUUCAAGAAGUGGUGUGtt | 26 |
| | | B | Sense | CUAUGUUCCUCUUGGAAUUtt | 27 |
| | | | Antisense | AAUUCCAAGAGGAACAUAGtt | 28 |
| | | C | Sense | CUGUCUGCGUUUCUUAGUAtt | 29 |
| | | | Antisense | UACUAAGAAACGCAGACGUtt | 30 |
| FOSL2 siRNA(m) | SC-35408 | A | Sense | GUCUCUUCUUGCUUCUAGUtt | 31 |
| | | | Antisense | ACUAGAAGCAAGAAGAGACtt | 32 |
| | | B | Sense | CACCAAAUGUCUGUAAUGAtt | 33 |
| | | | Antisense | UCAUUACAGACAUUUGGUGtt | 34 |
| | | C | Sense | CUAGGUAUCAGAUUCCUUUtt | 35 |
| | | | Antisense | AAAGGAAUCUGAUACCUAGtt | 36 |

TABLE 5-continued

Sequence information of siRNA used in this study (SEQ ID NOS: 1-58).

| Name | Catalog no. | Duplexe | | Sequences | SEQ ID NO: |
|---|---|---|---|---|---|
| FOS siRNA(m) | SC-29222 | A | Sense | GGUAGUUAGUAGAGCAUGUtt | 37 |
| | | | Antisense | ACAUGCUCUACUAACUACCtt | 38 |
| | | B | Sense | CUCCUGAAGAGGAAGAGAAtt | 39 |
| | | | Antisense | UUCUCUUCCUCUUCAGGAGtt | 40 |
| | | C | Sense | CGGAGACAGAUCAACUUGAtt | 41 |
| | | | Antisense | UCAAGUUGAUCUGUCUCCGtt | 42 |
| | | D | Sense | CACCUCUUCCAGAGAUGUAtt | 43 |
| | | | Antisense | UACAUCUCUGGAAGAGGUGtt | 44 |
| CXCL2 siRNA(m) | SC-45997 | A | Sense | CAAGGGUUGACUUCAAGAAtt | 45 |
| | | | Antisense | UUCUUGAAGUCAACCCUUGtt | 46 |
| | | B | Sense | GAUGCUGGAUUUCAAUGUAtt | 47 |
| | | | Antisense | UACAUUGAAAUCCAGCAUCtt | 48 |
| CXCL3 siRNA(m) | SC-142642 | A | Sense | GGGUAUAAUUGCAUCUACUtt | 49 |
| | | | Antisense | AGUAGAUGCAAUUAUACCCtt | 50 |
| | | B | Sense | GCAUGUGCACAUCUAGUUUtt | 51 |
| | | | Antisense | AAACUAGAUGUGCACAUGCtt | 52 |
| CMG2 siRNA(m) | Sc-60232 | A | Sense | GUGUGACAGUGUAUCUUCAtt | 53 |
| | | | Antisense | UGAAGAUACACUGUCACACtt | 54 |
| | | B | Sense | CGACAUGAGGUGAUGAAtt | 55 |
| | | | Antisense | UUCAUCACCUCUCAUGUCGtt | 56 |
| | | C | Sense | GAAGGAAAUAGCUCAGAUAtt | 57 |
| | | | Antisense | UAUCUGAGCUAUUUCCUUCtt | 58 |

MTT assay. Cells were seeded in 24-well or 96-well plates and treated with 4 µg/ml EdTx or 2 µg/ml LeTx for the indicated times, with PBS used as a negative control. MTT solution (5 mg/ml) was added into each well, followed by a 2-h incubation at 37° C. The medium was then removed, and dimethyl sulfoxide was added (0.2 ml/well in 96-well plates and 0.5 ml/well in 24-well plates) in order to solubilize the formazan crystals that formed. The absorbance was read at 570 nm using a PowerWave XS2 spectrophotometer (BioTek, Winooski, VT), and the data were normalized to the viable cells in the control group.

Mitochondria-regulated apoptosis assay by JC-1 staining. Visualization of mitochondrial membrane potential was accomplished using hepatocyte uptake of JC-1 (5,5',6,6'-tetrachloro-1,1',3,3'-tetraethylbenzimidazolycarbocyanine iodide, Thermo Fisher Scientific), a cationic carbocyanine dye that accumulates in mitochondria according to its membrane potential. At low membrane potential, JC-1 exerts a green fluorescence ($\lambda$em, 525 nm). At higher potentials, JC-1 forms red fluorescent "J-aggregates" ($\lambda$em, 590 nm). Hepatocytes were incubated with 10 µM JC-1 (dissolved in William's E medium) in a humidified atmosphere containing 95% air and 5% $CO_2$ at 37° C. for 30 min, followed by two washes with fresh medium. All images were acquired using a Nikon ECLIPSE Ti inverted fluorescence microscope with a digital CMOS camera (magnification, ×20) and controlled using NIS-Element software (Nikon Instruments, Tokyo, Japan).

Western blot assay. The hearts and livers were collected from three randomly selected mice in each group at 24 h after administration of 50 µg of LeTx. All the cells were cultured in 6-well plates and treated with 2 ml of 2 µg/ml LeTx for 0, 2, 6, 12, or 18 h. The cells and organs were lysed using cell lysis buffer and RIPA buffer (Cell Signal Technology, Boston, MA), respectively, with 1 µM PMSF protease inhibitor. Protein samples (30 µg) were separated by 10% SDS-PAGE and then transferred onto nitrocellulose membranes using a semi-dry transblot apparatus (Bio-Rad, Hercules, CA). The membranes were blocked with 5% nonfat milk in PBS containing 1% Tween (PBST) for 1 h and incubated with mouse monoclonal anti-MEK2 antibody (Santa Cruz Biotechnology, Dallas, TX) or mouse monoclonal anti-$\beta$-actin antibody (Cell Signaling Technology) at 4° C. overnight. After washing with PBST, the membranes were incubated with alkaline phosphatase-conjugated anti-mouse IgG at room temperature for 1 h. Following PBST rinses, the chemiluminescent signals were developed using 5-bromo-4-chloro-3-indolyl phosphate/nitro blue tetrazolium substrate (Sigma-Aldrich).

Indocyanine green (ICG) uptake-and-efflux assay. Primary hepatocytes or cardiomyocytes were treated with 2 µg/ml EdTx or LeTx for 6 h followed by an incubation with DMSO-dissolved ICG (final concentration, 0.5 mg/ml; Sigma-Aldrich) at 37° C. in a humidified atmosphere of 5% $CO_2$ for 2 h. Cells were monitored for an additional 24 h at 37° C. in culture medium prior to measurement of ICG efflux (Vaghjiani et al., 2014). Representative images were acquired using a Nikon ECLIPSE Ti inverted microscope.

Blood chemistry analysis. Four mice were randomly selected from each group, and the serum samples were collected at 18 h after injection and sent to IDEXX BioResearch (West Sacramento, CA) for blood chemistry analysis.

Histology analyses. Three mice were randomly selected from each group, and the liver of each mouse was harvested at 18 h after injection. One part of the liver tissues was fixed with 4% paraformaldehyde, followed by preparation of paraffin-embedded tissue sections with a thickness of 4 µm, which were then stained by the H&E and periodic acid-Schiff (PAS) methods before sending to Duke University Medical Center for a blinded histology analysis by independent pathologists.

Intracellular PAS staining. PAS staining was applied to detect glycogen in primary hepatocytes and cardiomyocytes. Cells were cultured in 8-well chamber slides (Thermo Fisher Scientific) and treated with 4 µg/ml EdTx or 2 µg/ml LeTx for 6 h, followed by fixation with formaldehyde and staining with PAS using a PAS staining system (Sigma-Aldrich) or a Glycogen Colorimetric Assay Kit II (BioVision, Milpitas, CA), according to the respective manufacturers' protocols.

Microarray. Primary hepatocytes and cardiomyocytes were exposed to 4 µg/ml EdTx for 6 h and 2 µg/mL LeTx for 18 h, with PBS as a negative control. Cells were incubated in William's E medium and processed as four independent replicates. Total RNA was extracted from the cells and sent to the Genomics & Microarray Core Facility at UT Southwestern Medical Center in Dallas for microarray assay using the GeneChips Mouse Transcriptome Assay 1.0 (Affymetrix). The data were analyzed using Partek Genomic Suite software (Partek Inc., St. Louis, MO, USA).

Polymerase chain reaction (PCR). Cells were cultured in 6-well plates to 90-95% confluence and treated with 4 µg/ml EdTx for 6 h or 2 µg/ml LeTx for 18 h. The livers and hearts were collected from mice challenged with 20 µg EdTx for 18 h or 50 µg LeTx for 24 h. Total RNA was isolated from cells or tissues using the RNeasy Mini kit (Qiagen, Valencia, CA), and cDNA was synthesized using the ProtoScript® First Strand cDNA Synthesis Kit (New England BioLabs, Inc., Ipswich, MA) following the manufacturer's instructions. Murine Tem8 (584 bp), Cmg2 (364 bp), and glyceraldehyde-3-phosphate dehydrogenase (Gapdh; 239 bp) fragments were amplified using Master Mix, and specific primers are listed in Table 6, as previously described (Arevalo et al., 2014).

TABLE 6

Primers used for qPCR in this paper.

| | Gene bank ID | | Primers(5'-3') | SEQ. ID. NO. |
|---|---|---|---|---|
| Arg2 | NM_009705 | sense | CCCACAAGATGATCCCTACAAT | 59 |
| | | antisense | CACCTGACACAGCTCTACTAAC | 60 |
| Ass1 | NM_007494 | sense | GAAGAGCTGGTGAGCATGAA | 61 |
| | | antisense | AGCCTGAGCGAGTTGATATTG | 62 |
| Cbs | NM_001271353 | sense | TCCTAACACCCAGCTACCTAAA | 63 |
| | | antisense | CCATCCTTCCTGGCTAACATTC | 64 |
| Cps1 | NM_001080809 | sense | GAGACGAACTGGGACTGAATAA | 65 |
| | | antisense | GTAGCCAGCCAGTGGTTATAG | 66 |
| Got1 | NM_010324 | sense | CCCAAGCAGGTCGAGTATTT | 67 |
| | | antisense | TGGAGGTAGCGACGTAATCTA | 68 |
| Pab | NM_008777 | sense | ATACACAGAGGAGGAGAGGAAG | 69 |
| | | antisense | AAGAGGGAAGATGTGGTTGTG | 70 |
| Tat | NM_146214 | sense | CCTGGACAGAACATCCTCATTC | 71 |
| | | antisense | CCCAAGACTTCTCAGGCAATAG | 72 |
| Gfpt1 | NM_013528 | sense | GCAAGAGAGACGCAAAGAGA | 73 |
| | | antisense | GACCGACTTCTGGTGGTAAAG | 74 |
| Gfpt2 | NM_013529 | sense | GTCCTCCGAGGTTATGATGTTG | 75 |
| | | antisense | GGTGACGACAGTCTTGTGATAG | 76 |
| Akr1b7 | NM_009731 | sense | CCTGAACAAGCCTGGACTAAA | 77 |
| | | antisense | GATGCCCTTGGATTGACAGTA | 78 |
| B3gnt5 | NM_001159407 | sense | CTGCACTACCCATCCATTGT | 79 |
| | | antisense | TTTCCCACAGTCACAGCATAG | 80 |
| Crem | NM_001110850 | sense | GAAGAAGGGACACCACCTAAC | 81 |
| | | antisense | GTCACCTGTGGCAGTGTATT | 82 |
| Csf2rb | NM_007780 | sense | GGTCAAGCCCATCTCTAACTAC | 83 |
| | | antisense | GGATGAGAAAGACCAGGATGAG | 84 |
| Csf2rb2 | NM_001287389 | sense | AGCTCTGCATGGTCTGTTTAG | 85 |
| | | antisense | GGCAGAAATGTGCTGTGTTATC | 86 |
| Cyp17a1 | NM_007809 | sense | ACCAGCCAGATCGGTTTATG | 87 |
| | | antisense | TAACTGGGTGTGGGTGTAATG | 88 |
| Dgat1 | NM_010046 | sense | GGCCTTACTGGTTGAGTCTATC | 89 |
| | | antisense | GTTGACATCCCGGTAGGAATAA | 90 |
| Entpd1 | NM_009848 | sense | GCCCTAACTCAAGCTGTCTATC | 91 |
| | | antisense | GATTCAGGACACTTGGCTTCTA | 92 |
| Etnppl | NM_001163587 | sense | GGGACTTTGATTCTGGCTACTC | 93 |
| | | antisense | CAGTGGGATGCAGGTGATAAT | 94 |

TABLE 6-continued

Primers used for qPCR in this paper.

| Gene | bank ID | | Primers(5'-3') | SEQ. ID. NO. |
|---|---|---|---|---|
| G6pc | NM_008061 | sense | GCATTTGCCAGGAAGAGAAAG | 95 |
| | | antisense | AACTGAAGCCGGTTAGACATAG | 96 |
| Gem | NM_010276 | sense | TGTGAGGTCTTGGGAGAAGATA | 97 |
| | | antisense | CCACATGTCCAGGAGGATAATG | 98 |
| Hpgds | NM_019455 | sense | GCTCCTAGTGTTGCTGTGAA | 99 |
| | | antisense | CCCTGTAAGCTGTTGTGTATCT | 100 |
| Lepr | NM_001122899 | sense | GAGATGGCTCAGTGGTTAAGAG | 101 |
| | | antisense | GGATTTCATTACGGATGGTTGTG | 102 |
| Pck1 | NM_011044 | sense | TTTGTAGGAGCAGCCATGAG | 103 |
| | | antisense | CCGAAGTTGTAGCCGAAGAA | 104 |
| Pde3b | NM_011055 | sense | GTCTGCTGGCTCTCTAACTAATC | 105 |
| | | antisense | GAAATCTGCTGCACTTGATACAC | 106 |
| Pde4b | NM_001177980 | sense | GGAGAAGGCCACAGCTATTT | 107 |
| | | antisense | CCACACAGAGGGAGAGAGATTA | 108 |
| Ppargc1a | NM_008904 | sense | GACAATCCCGAAGACACTACAG | 109 |
| | | antisense | AGAGAGGAGAGAGAGAGAGA | 110 |
| Ptprn | NM_008985 | sense | ATCTTCCCTCTACCACGTCTAT | 111 |
| | | antisense | GGTCTGCAGGTTCTTAAGGTAG | 112 |
| Ramp3 | NM_019511 | sense | TTGGGCTAGTGGAAGAAAGTG | 113 |
| | | antisense | CTGCCAAGAAACGGCTAGAA | 114 |
| Rdh12 | NM_030017 | sense | GGATCCTGGGAAGTTGGATTAG | 115 |
| | | antisense | CTAGAGCTGGAGGGAATAGAAATG | 116 |
| Rgs1 | NM_015811 | sense | CGAGAATCGACAGCCAAGAA | 117 |
| | | antisense | TGATTTCAGGAACCTGGGATAAG | 118 |
| Rgs2 | NM_009061 | sense | TCGGGAAAGCAGAGTTTGAG | 119 |
| | | antisense | CCAACTAGCTAAGGCCACATAA | 120 |
| Sgk1 | NM_001161845 | sense | CTAGGCACAAGGCAGAAGAA | 121 |
| | | antisense | AGAACATTCCGCTCTGACATAA | 122 |
| Sik1 | NM_010831 | sense | AAACCTCCCTTGGTCACATTAG | 123 |
| | | antisense | TCTTCCCTGACACCTCTACTC | 124 |
| Slc25a25 | NM_001164357 | sense | GGACCGGAGGATTTCTTTATT | 125 |
| | | antisense | CTTCAGTCCTCACCCTCAAAC | 126 |
| Tbxas1 | NM_011539 | sense | TTCACATACCTGCCCTTTGG | 127 |
| | | antisense | CTTGTGTAGGACCTGGAGTATTG | 128 |
| Tgfbr1 | NM_009370 | sense | CCTTGAGTCACTGGGTGTTATG | 129 |
| | | antisense | CCACTTAGCTGTCACCCTAATC | 130 |
| Tgm2 | NM_009373 | sense | CATCACCAGCACTCTGTATCTC | 131 |
| | | antisense | GGTTCCTTCGGTTCCTTCAT | 132 |
| Uap1 | NM_133806 | sense | GAGAGGGCCTTGAAGGTTATG | 133 |
| | | antisense | CTATGTGGCCCGTTAGGATTT | 134 |
| Uck2 | NM_030724 | sense | CGAGACCTGTTCCAGATGAAG | 135 |
| | | antisense | TTCGCTGATGTCCCTCAATAC | 136 |
| BMP7 | NM_007557 | sense | AGAGGTGGGATGTTGGTTATG | 137 |
| | | antisense | CCAGTTTAACCCTCTGCATTTG | 138 |
| C3ar1 | NM_009779 | sense | GAGCAAGTGAGCACAGATACA | 139 |
| | | antisense | GCAGAATACACAGGGAAGAGAG | 140 |
| Cd180 | NM_008533 | sense | CTCCGAAACCTGTCTCACTTAC | 141 |
| | | antisense | GTTCTAGCTGAGGGCATTCTT | 142 |
| Cd55 | NM_010016 | sense | GACAGACAGACAGACAGACATAC | 143 |
| | | antisense | GTCTCCAACCACTTCCTCTTAAT | 144 |

TABLE 6-continued

Primers used for qPCR in this paper.

| Gene | bank ID | | Primers(5'-3') | SEQ. ID. NO. |
|---|---|---|---|---|
| Cd86 | NM_019388 | sense | CCTGGAAAGGTCTGGAGAATG | 145 |
| | | antisense | GGCAGATCAGTCCTTCCATAAA | 146 |
| Cxcl2 | NM_009140 | sense | TAAGCACCGAGGAGAGTAGAA | 147 |
| | | antisense | GTCCAAGGGTTACTCACAACA | 148 |
| Cxcl3 | NM_203320 | sense | GCACCCAGACAGAAGTCATAG | 149 |
| | | antisense | ACTTGCCGCTCTTCAGTATC | 150 |
| Cyr61 | NM_010516 | sense | CCAGTGTACAGCAGCCTAAA | 151 |
| | | antisense | CTGGAGCATCCTGCATAAGTAA | 152 |
| Egln3 | NM_028133 | sense | GCCCAGGACTGCTTCTTATT | 153 |
| | | antisense | TGGCATCTGTCACCAACTTTA | 154 |
| F5 | NM_007976 | sense | GTCCAGTTTATCCTCTGCTCTTG | 155 |
| | | antisense | CACAGGTCACAGTCCCTTATTG | 156 |
| Fos | NM_010234 | sense | GAATCCGAAGGGAACGGAATAA | 157 |
| | | antisense | TCTCCGCTTGGAGTGTATCT | 158 |
| Fosl2 | NM_008037 | sense | GCCTGCTTGCTTTGTCTTAC | 159 |
| | | antisense | GAGGTCACACCCAGAGTTTAG | 160 |
| Hcar2 | NM_030701 | sense | CCTTATCTGGCTTCCACATCTC | 161 |
| | | antisense | GTTCAACGAACGGCCAAATC | 162 |
| Hilpda | NM_001190461 | sense | GCAGGATCTAGCAGCAGAAA | 163 |
| | | antisense | CATGATGCCCAGCACATAGA | 164 |
| Igf1 | NM_001111274 | sense | GCTGCTGAAGCCATTCATTTAG | 165 |
| | | antisense | CGTGGGAAGAGGTGAAGATAAG | 166 |
| Il11 | NM_008350 | sense | GGGATCACCTGTGGCTTATT | 167 |
| | | antisense | GATCTCAGTTCCCTGCTCTTC | 168 |
| Il1b | NM_008361 | sense | ATGGGCAACCACTTACCTATTT | 169 |
| | | antisense | GTTCTAGAGAGTGCTGCCTAATG | 170 |
| Il1r2 | NM_010555 | sense | CTGATAGTCCCGTGCAAAGT | 171 |
| | | antisense | GGGTAAGCAGCCGAGATAAA | 172 |
| Il33 | NM_001164724 | sense | CCTACTCCCTCAGCTTTCTTTC | 173 |
| | | antisense | GCAGGGTAAAGACAGTGGAATA | 174 |
| Il6 | NM_031168 | sense | GTCTGTAGCTCATTCTGCTCTG | 175 |
| | | antisense | GAAGGCAACTGGATGGAAGT | 176 |
| Il7r | NM_008372 | sense | GCGTATGTCACCATGTCTAGTT | 177 |
| | | antisense | AGCATTCCAGACTTTCCATCTC | 178 |
| Ngf | NM_001112698 | sense | CAGTGAGGTGCATAGCGTAAT | 179 |
| | | antisense | CTCCTTCTGGGACATTGCTATC | 180 |
| Nr4a2 | NM_001139509 | sense | CAGAGCTACAGTTACCACTCTTC | 181 |
| | | antisense | TGGTGAGGTCCATGCTAAAC | 182 |
| Nr4a3 | NM_015743 | sense | CTCAGTGTCGGGATGGTAAG | 183 |
| | | antisense | CCTGTTGTAGTGGGCTCTTT | 184 |
| Procr | NM_011171 | sense | GCCTCCCTTCTCTTTCCTAATC | 185 |
| | | antisense | GGCAGAAACTTCGTCAACATC | 186 |
| Rasgef1b | NM_145839 | sense | GAGCGAGGATGATCGAGTATTT | 187 |
| | | antisense | CGGGCTCATATTCATACCAGAG | 188 |
| Star | NM_011485 | sense | GCTGTGAAGGCTAAGGGATAAG | 189 |
| | | antisense | GTGACATTTGGAGCTGGTAAGA | 190 |
| Tlr7 | NM_133211 | sense | GCCATCCAGCTTACATCTTCT | 191 |
| | | antisense | TTTGACCCAGGTAGAGTGTTTC | 192 |
| Tnfaip6 | NM_009398 | sense | TGGCCTCGAACTCAGAAATC | 193 |
| | | antisense | CGAGGTCCAAGAGCTACAAATA | 194 |

TABLE 6-continued

Primers used for qPCR in this paper.

| Gene | bank ID | | Primers(5'-3') | SEQ. ID. NO. |
|---|---|---|---|---|
| Trem1 | NM_021406 | sense | GTCCAGTTTATCCTCTGCTCTTG | 195 |
| | | antisense | CACAGGTCACAGTCCCTTATTG | 196 |
| Vegfa | NM_001025250 | sense | TGGTTCTTCACTCCCTCAAATC | 197 |
| | | antisense | GGTCTCTCTCTCTCTTCCTTGA | 198 |
| Ucp3 | NM_009464 | sense | CATCAGGGTGTTGGGAAGATAG | 199 |
| | | antisense | CATTGTCCTCAGGCTTACATTTG | 200 |
| Egln3 | NM_028133 | sense | GCCCAGGACTGCTTCTTATT | 201 |
| | | antisense | TGGCATCTGTCACCAACTTTA | 202 |
| Gp49a | NM_008147 | sense | CTGTCAGTCTATCCCAGCTCTA | 203 |
| | | antisense | CCATGCTTTCCTTCCTGTATCA | 204 |
| Map2k6 | NM_011943 | sense | GGATACGGGCCACAGTTAATAG | 205 |
| | | antisense | GTAGAAGGTCACGGTGAATGG | 206 |
| Mmp12 | NM_008605 | sense | GACATCTTGGCTCCCTATCTTC | 207 |
| | | antisense | TGGACAATACACCAGTCAGTTTT | 208 |
| Rcan1 | NM_001081549 | sense | CCGACAAACAGTTCCTCATCT | 209 |
| | | antisense | CCAGCTTGGAGATGGCATATAA | 210 |
| Hbegf | NM_010415 | sense | CTGGGTCCTATTTGCTCTGTAA | 211 |
| | | antisense | CTCTGACCATACACAACCTACC | 212 |
| Sprr1a | NM_009264 | sense | CTGAAGACCTGATCACCAGATG | 213 |
| | | antisense | GTGCAAGGAGAGAGGGATTAAG | 214 |
| Lilrb4 | NM_013532 | sense | CCCTCTGGAAACCAGGAATAAG | 215 |
| | | antisense | CCAGCAGCACTCTCATAGTAAC | 216 |
| Bmp10 | NM_009756 | sense | CTGGGTATGAAGCCTATGAGTG | 217 |
| | | antisense | GTGGACCAAGGCCTGAATAA | 218 |
| Abra | NM_175456 | sense | CTGTAAGGCCCATCGGAAATA | 219 |
| | | antisense | ACTGAAGGGATTGAGCTTCTG | 220 |
| Ctgf | NM_010217 | sense | CAAATGCTGTGCAGGTGATAAA | 221 |
| | | antisense | CCTGAGCCAGCCATTTCTTA | 222 |
| Nppb | NM_001287348 | sense | ACCACCTTTGAAGTGATCCTATT | 223 |
| | | antisense | GCAAGTTTGTGCTCCAAGATAAG | 224 |
| Dusp1 | NM_013642 | sense | CATGGGAGCTGGTCCTTATTT | 225 |
| | | antisense | CTTGCGGTCAAGTCATTGTTG | 226 |
| Ier3 | NM_133662 | sense | GGTCACAGTCCGAAGAAACA | 227 |
| | | antisense | CTGAGTTAGCGTTGCCTTAGA | 228 |
| Serpine1 | NM_008871 | sense | GGGACGAAACTGGAGATGTTAT | 229 |
| | | antisense | GAGGAGTTGCCTTCTCTTTCTC | 230 |
| Ptgs2 | NM_011198 | sense | CGGACTGGATTCTATGGTGAAA | 231 |
| | | antisense | CTTGAAGTGGGTCAGGATGTAG | 232 |
| Tnfrsf12a | NM_001161746 | sense | CATAGAGGAGACTGGTGGAGA | 233 |
| | | antisense | AGGCTGACTCCAGAATGAATG | 234 |
| GAPDH | NM_001289726 | sense | AACAGCAACTCCCACTCTTC | 235 |
| | | antisense | CCTGTTGCTGTAGCCGTATT | 236 |
| GAPDH (PCR only) | Arevalo et al., 2014 | sense | TGAAGGTCGGTGTGAACGGATTTGGC | 237 |
| | | antisense | TAGTGGGGTCTCGCTCCTGGAAGATG | 238 |
| Cmg2 | Arevalo et al., 2014 | sense | CTGACAGAGAGATTTGTGAGC | 239 |
| | | antisense | GCAATTCTTTCCAGCTGA | 240 |

Statistical analysis. In the microarray study, the data were analyzed using Partek software version 6.6, and the two-tailed paired t-test was utilized to identify differences in the expression levels. For other studies, GraphPad Prism version 5.04 was used to perform statistical analyses. The differences among multiple groups were compared using two-tailed, one-way analysis of variance, followed by Dunnett's multiple comparison tests. A p value less than 0.05 was considered statistically significant.

In one embodiment, the present invention includes a composition for decreasing Bacillus anthracis virulence or toxicity comprising, consists essentially of, or consists of: at least one inhibitor that decreases an expression of one or more host genes selected from G6pc, Rgs1, Fosl2, Hcar2, Cxcl2 and Cxcl3, or Serpine1 (PAI-1), wherein the composition decreases the virulence or toxicity of Bacillus anthracis. In one aspect, the inhibitor is an RNA molecule active for gene silencing through RNA interference (RNAi) or a small molecule inhibitor of the proteins. In another aspect, the composition further comprises a pharmaceutically acceptable carrier. In another aspect, the carrier is a lipid molecule or liposome. In another aspect, the inhibitor comprises a polynucleotide sense strand and a polynucleotide antisense strand that are connected as a single strand, and form a duplex region connected at one end by a loop. In another aspect, wherein at least one polynucleotide in any strand is at least chemically modified at one base. In another aspect, the inhibitor targets disruption or knockdown of the G6pc, Rgs1, Fosl2, Hcar2, Cxcl2 and Cxcl3, or Serpine1 (PAI-1) gene in a living cell. In another aspect, the composition further comprises a delivery system or expression system for antisense oligonucleotide, ribozyme or an inhibitory RNA. In another aspect, the inhibitory RNA is selected from the group consisting of an siRNA, shRNA, a bishRNA, and miRNA. In another aspect, the virulence is cardiotoxicity or hepatotoxicity. In another aspect, the inhibitors are polynucleotides selected from SEQ ID NOS: 1-58.

In another embodiment, the present invention includes a method of decreasing the virulence or toxicity of Bacillus anthracis comprising, consists essentially of, or consists of: identifying a subject in need of treatment for an infection with or exposure to one or more Bacillus anthracis spores, vegetative cells, toxins; and providing the subject with an effective amount of an inhibitor of an expression of one or more host genes selected from G6pc, Rgs1, Fosl2, Hcar2, Cxcl2 and Cxcl3, or Serpine1 (PAI-1) sufficient to decrease Bacillus anthracis virulence or toxicity. In one aspect, the inhibitor is an RNA molecule active for gene silencing through RNA interference (RNAi) or a small molecule inhibitor of the proteins. In another aspect, the composition further comprises a pharmaceutically acceptable carrier. In another aspect, the carrier is a lipid molecule or liposome. In another aspect, the inhibitor comprises a polynucleotide sense strand and a polynucleotide antisense strand that are connected as a single strand, and form a duplex region connected at one end by a loop. In another aspect, wherein at least one polynucleotide in any strand is at least chemically modified at one base. In another aspect, the inhibitor targets disruption or knockdown of the G6pc, Rgs1, Fosl2, Hcar2, Cxcl2 and Cxcl3, or Serpine1 (PAI-1) gene in a living cell. In another aspect, the composition further comprises a delivery system or expression system for antisense oligonucleotide, ribozyme or an inhibitory RNA. In another aspect, the inhibitory RNA is selected from the group consisting of an siRNA, shRNA, a bishRNA, and miRNA. In another aspect, the virulence is cardiotoxicity or hepatotoxicity. In another aspect, the inhibitors are polynucleotides selected from SEQ ID NOS: 1-58.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

Arevalo, M. T., Navarro, A., Arico, C. D., Li, J., Alkhatib, O., Chen, S., Diaz-Arevalo, D., and Zeng, M. (2014). Targeted silencing of anthrax toxin receptors protects against anthrax toxins. The Journal of biological chemistry 289, 15730-15738.

Arsand, E., Walseth, O. A., Andersson, N., Fernando, R., Granberg, O., Bellika, J. G., and Hartvigsen, G. (2005). Using blood glucose data as an indicator for epidemic disease outbreaks. Studies in health technology and informatics 116, 217-222.

Bai, Y. N., Zhang, T., Wu, H., and Zeng, Y. (2014). [Isolation of mouse primary hepatocytes by retrograde liver perfusion with catheterization via heart]. Sichuan da xue xue bao Yi xue ban=Journal of Sichuan University Medical science edition 45, 138-141.

Bhattacharya, K. (2015). Investigation and management of the hepatic glycogen storage diseases. Translational pediatrics 4, 240-248.

Bouschet, T., Martin, S., and Henley, J. M. (2005). Receptor-activity-modifying proteins are required for forward trafficking of the calcium-sensing receptor to the plasma membrane. Journal of cell science 118, 4709-4720.

Croft, W., Hill, C., McCann, E., Bond, M., Esparza-Franco, M., Bennett, J., Rand, D., Davey, J., and Ladds, G. (2013). A physiologically required G protein-coupled receptor (GPCR)-regulator of G protein signaling (RGS) interaction that compartmentalizes RGS activity. The Journal of biological chemistry 288, 27327-27342.

Dal Molin, F., Zornetta, I., Puhar, A., Tonello, F., Zaccolo, M., and Montecucco, C. (2008). cAMP imaging of cells treated with pertussis toxin, cholera toxin, and anthrax edema toxin. Biochemical and biophysical research communications 376, 429-433.

De Vries, L., Zheng, B., Fischer, T., Elenko, E., and Farquhar, M. G. (2000). The regulator of G protein signaling family. Annual review of pharmacology and toxicology 40, 235-271.

Denecke, B., Meyerdierks, A., and Bottger, E. C. (1999). RGS1 is expressed in monocytes and acts as a GTPase-activating protein for G-protein-coupled chemoattractant receptors. The Journal of biological chemistry 274, 26860-26868.

Dostalova, G., Belohlavek, J., Hlubocka, Z., Bayerova, K., Bobcikova, P., Kvasnicka, T., Kvasnicka, J., Linhart, A., and Karetova, D. (2017). Multiple thrombophilia mutations as a possible cause of premature myocardial infarction. Wiener klinische Wochenschrift 129, 503-508.

Edwards, M., Houseman, L., Phillips, I. R., and Shephard, E. A. (2013). Isolation of mouse hepatocytes. Methods Mol Biol 987, 283-293.

Faybik, P., and Hetz, H. (2006). Plasma disappearance rate of indocyanine green in liver dysfunction. Transplantation proceedings 38, 801-802.

Firoved, A. M., Miller, G. F., Moayeri, M., Kakkar, R., Shen, Y., Wiggins, J. F., McNally, E. M., Tang, W. J., and Leppla, S. H. (2005). *Bacillus anthracis* edema toxin causes extensive tissue lesions and rapid lethality in mice. The American journal of pathology 167, 1309-1320.

Flevaris, P., and Vaughan, D. (2017). The Role of Plasminogen Activator Inhibitor Type-1 in Fibrosis. Seminars in thrombosis and hemostasis 43, 169-177.

Gille, A., Lushington, G. H., Mou, T. C., Doughty, M. B., Johnson, R. A., and Seifert, R. (2004). Differential inhibition of adenylyl cyclase isoforms and soluble guanylyl cyclase by purine and pyrimidine nucleotides. The Journal of biological chemistry 279, 19955-19969.

Grundmann, O. (2014). The current state of bioterrorist attack surveillance and preparedness in the US. Risk management and healthcare policy 7, 177-187.

Han, J. I., Huang, N. N., Kim, D. U., and Kehrl, J. H. (2006). RGS1 and RGS13 mRNA silencing in a human B lymphoma line enhances responsiveness to chemoattractants and impairs desensitization. Journal of leukocyte biology 79, 1357-1368.

Heiman, M., Gupta, S., Khan, S. S., Vaughan, D. E., and Shapiro, A. D. (1993). Complete Plasminogen Activator Inhibitor 1 Deficiency. In GeneReviews®, R. A. Pagon, M. P. Adam, H. H. Ardinger, S. E. Wallace, A. Amemiya, L. J. H. Bean, T. D. Bird, N. Ledbetter, H. C. Mefford, R. J. H. Smith, et al., eds. (Seattle (Wash.)).

Henderson, D. A. (2014). John Bartlett and bioterrorism. Clinical infectious diseases: an official publication of the Infectious Diseases Society of America 59 Suppl 2, S76-79.

Hepler, J. R. (1999). Emerging roles for RGS proteins in cell signaling. Trends in pharmacological sciences 20, 376-382.

Houseman, L., Edwards, M., Phillips, I. R., and Shephard, E. A. (2015). Isolation and Culture of Mouse Hepatocytes: Gender-Specific Gene Expression Responses to Chemical Treatments. Methods Mol Biol 1250, 3-12.

Jaswal, D. S., Cui, X., Torabi-Parizi, P., Ohanjanian, L., Sampath-Kumar, H., Fitz, Y., Li, Y., Xu, W., and Eichacker, P. Q. (2017). *Bacillus anthracis* Edema Toxin Increases Fractional Free Water and Sodium Reabsorption in an Isolated Perfused Rat Kidney Model. Infect Immun 85.

Liu, S., Moayeri, M., and Leppla, S. H. (2014). Anthrax lethal and edema toxins in anthrax pathogenesis. Trends in microbiology 22, 317-325.

Liu, S., Zhang, Y., Moayeri, M., Liu, J., Crown, D., Fattah, R. J., Wein, A. N., Yu, Z. X., Finkel, T., and Leppla, S. H. (2013). Key tissue targets responsible for anthrax-toxin-induced lethality. Nature 501, 63-68.

Lubker, C., Dove, S., Tang, W. J., Urbauer, R. J., Moskovitz, J., Urbauer, J. L., and Seifert, R. (2015). Different Roles of N-Terminal and C-Terminal Domains in Calmodulin for Activation of *Bacillus anthracis* Edema Factor. Toxins 7, 2598-2614.

Lugli, E., Troiano, L., Ferraresi, R., Roat, E., Prada, N., Nasi, M., Pinti, M., Cooper, E. L., and Cossarizza, A. (2005). Characterization of cells with different mitochondrial membrane potential during apoptosis. Cytometry Part A: the journal of the International Society for Analytical Cytology 68, 28-35.

Mithieux, G., Rajas, F., and Gautier-Stein, A. (2004). A novel role for glucose 6-phosphatase in the small intestine in the control of glucose homeostasis. The Journal of biological chemistry 279, 44231-44234.

Mutel, E., Gautier-Stein, A., Abdul-Wahed, A., Amigo-Correig, M., Zitoun, C., Stefanutti, A., Houberdon, I., Tourette, J. A., Mithieux, G., and Rajas, F. (2011). Control of blood glucose in the absence of hepatic glucose production during prolonged fasting in mice: induction of renal and intestinal gluconeogenesis by glucagon. Diabetes 60, 3121-3131.

Oh, K. J., Han, H. S., Kim, M. J., and Koo, S. H. (2013). CREB and FoxO1: two transcription factors for the regulation of hepatic gluconeogenesis. BMB reports 46, 567-574.

Patel, K., Foretz, M., Marion, A., Campbell, D. G., Gourlay, R., Boudaba, N., Tournier, E., Titchenell, P., Peggie, M., Deak, M., et al. (2014). The LKB1-salt-inducible kinase pathway functions as a key gluconeogenic suppressor in the liver. Nature communications 5, 4535.

Poole, L. G., Massey, V. L., Siow, D. L., Tones-Gonzalez, E., Warner, N. L., Luyendyk, J. P., Ritzenthaler, J. D., Roman, J., and Arteel, G. E. (2017). Plasminogen Activator Inhibitor-1 is Critical in Alcohol-enhanced Acute Lung Injury in Mice. American journal of respiratory cell and molecular biology.

Sastalla, I., Tang, S., Crown, D., Liu, S., Eckhaus, M. A., Hewlett, I. K., Leppla, S. H., and Moayeri, M. (2012). Anthrax edema toxin impairs clearance in mice. Infect Immun 80, 529-538.

Serezani, C. H., Ballinger, M. N., Aronoff, D. M., and Peters-Golden, M. (2008). Cyclic AMP: master regulator of innate immune cell function. American journal of respiratory cell and molecular biology 39, 127-132.

Sugden, B. W., and Katchmar, R. (2005). Bioterrorism and its aftermath: dealing individually and organizationally with the emotional reactions to an anthrax attack. International journal of emergency mental health 7, 203-211.

Vaghjiani, V., Vaithilingam, V., Saraswati, I., Sali, A., Murthi, P., Kalionis, B., Tuch, B. E., and Manuelpillai, U. (2014). Hepatocyte-like cells derived from human amniotic epithelial cells can be encapsulated without loss of viability or function in vitro. Stem cells and development 23, 866-876.

Welkos, S. L., Keener, T. J., and Gibbs, P. H. (1986). Differences in susceptibility of inbred mice to *Bacillus anthracis*. Infect Immun 51, 795-800.

What is claimed is:

1. A composition for decreasing virulence or toxicity of *Bacillus anthracis* to a host comprising:
   inhibitors that decrease an expression of host genes Fosl2, Hcar2, Cxcl2, and Cxcl3, wherein a decrease in the expression of the host genes reduces a cell surface expression of Hcar2, and expression of Fosl2, Cxcl2 and Cxcl3, and wherein the reduction in expression of Hcar2, and Fosl2, Cxcl2, and Cxcl3, decreases the virulence or toxicity of the *Bacillus anthracis* to the host cell, wherein the inhibitors comprise an RNA molecule active for gene silencing through RNA interference (RNAi) against Fosl2 selected from SEQ ID NOS: 32, 34, or 36; against Hcar2 selected from SEQ ID NOS: 26, 28, or 30; against Cxcl2 selected from SEQ ID NOS: 46 and 48; and against Cxcl3 selected from SEQ ID NOS: 50 and 52.

2. The composition of claim 1, further comprising a pharmaceutically acceptable carrier.

3. The composition of claim 2, wherein the carrier is a lipid molecule or liposome.

4. The composition of claim 1, wherein the RNA molecule comprises a polynucleotide sense strand and a polynucleotide antisense strand that are connected as a single strand, and form a duplex region connected at one end by a loop.

5. The composition of claim 4, wherein at least one polynucleotide in any strand is at least chemically modified at one base.

6. The composition of claim 1, wherein the RNA molecule is selected from the group consisting of siRNA, shRNA, a bishRNA, and miRNA.

7. The composition of claim 1, wherein the virulence is cardiotoxicity or hepatotoxicity.

8. The composition of claim 1, wherein each of the inhibitors is a polynucleotide selected from SEQ ID NOS: 1-58.

9. A composition comprising of:
   inhibitors that decreases an expression of host genes Fosl2, Hcar2, or Cxcl2 and Cxcl3, in an amount sufficient to decrease the virulence or toxicity of a *Bacillus anthracis* to a host, wherein the inhibitors are RNA molecules active for gene silencing through RNA interference (RNAi) against Fosl2 selected from SEQ ID NO: 32, 34 or 36; against Hcar2 selected from SEQ ID NO:26, 28, or 30; against Cxcl2 selected from SEQ ID NO: 46 and 48; and against Cxcl3 selected from SEQ ID NOS: 50 and 52.

\* \* \* \* \*

SEQUENCE LISTING

```
<160> NUMBER OF SEQ ID NOS: 240

<210> SEQ ID NO 1
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 1
gguucagauu guccauacun n                                             21

<210> SEQ ID NO 2
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 2
```
aguauggaca aucugaaccn n					21

<210> SEQ ID NO 3
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 3
cugagcacau cauuuaucan n					21

<210> SEQ ID NO 4
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 4
ugauaaauga ugugcucagn n					21

<210> SEQ ID NO 5
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 5
cucugugauc ugucacgaun n					21

<210> SEQ ID NO 6
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 6
aucgugacag aucacagagn n					21

<210> SEQ ID NO 7
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 7

```
gacucagaaa ggauuaacan n                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 8
uguuaauccu uucugagucn n                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 9
ggaagcauga acaagaagan n                                              21

<210> SEQ ID NO 10
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 10
ucuucuuguu caugcuuccn n                                              21

<210> SEQ ID NO 11
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 11
gaagcaugaa caagaagaan n                                              21

<210> SEQ ID NO 12
<211> LENGTH: 21
<212> TYPE: DNA
<213> ORGANISM: Artificial Sequence
<220> FEATURE:
<223> OTHER INFORMATION: siiRNA antisense
<220> FEATURE:
<221> NAME/KEY: misc_feature
<222> LOCATION: (20)..(21)
<223> OTHER INFORMATION: n is t
```

```
<400> SEQUENCE: 12
uucuucuugu ucaugcuucn n                                              21

<210> SEQ ID NO 13
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 13
ccauguaugu caucccauun n                                              21

<210> SEQ ID NO 14
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 14
aaugggauga cauacauggn n                                              21

<210> SEQ ID NO 15
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 15
gcaacuuaag ggcuaucaan n                                              21

<210> SEQ ID NO 16
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 16
uugauagccc uuaaguugcn n                                              21

<210> SEQ ID NO 17
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t
```

```
<400> SEQUENCE: 17
cagaaggagu acccauugan n                                              21

<210> SEQ ID NO 18
<211> LENGTH: 21
<212> TYPE: RNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 18
ucaaugggua cuccuucugn n                                              21

<210> SEQ ID NO 19
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 19
caugcagagu cuuugguaun n                                              21

<210> SEQ ID NO 20
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 20
auaccaaaga cucugcaugn n                                              21

<210> SEQ ID NO 21
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 21
gcaaaccaga ugcaaucuan n                                              21

<210> SEQ ID NO 22
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
```

```
<223> OTHER INFORMATION: n is t

<400> SEQUENCE: 22
uagauugcau cugguuugcn n                                              21

<210> SEQ ID NO 23
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 23
cucuaucacg ucacaguuun n                                              21

<210> SEQ ID NO 24
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 24
aaacugugac gugauagagn n                                              21

<210> SEQ ID NO 25
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 25
cacaccacuu cuugaacaan n                                              21

<210> SEQ ID NO 26
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 26
uuguucaaga aguggugugn n                                              21

<210> SEQ ID NO 27
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
```

```
<222> LOCATION: (20)..(21)
<223> OTHER INFORMATION: n is t

<400> SEQUENCE: 27
cuauguuccu cuuggaauun n                                              21

<210> SEQ ID NO 28
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 28
aauuccaaga ggaacauagn n                                              21

<210> SEQ ID NO 29
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 29
cugucugcgu uucuuaguan n                                              21

<210> SEQ ID NO 30
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 30
uacuaagaaa cgcagacagn n                                              21

<210> SEQ ID NO 31
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 31
gucucuucuu gcuucuagun n                                              21

<210> SEQ ID NO 32
<211> LENGTH: 21
<212> TYPE: DNA
<213> ORGANISM: Artificial Sequence
<220> FEATURE:
<223> OTHER INFORMATION: siRNA antisense
<220> FEATURE:
```

```
<221> NAME/KEY: misc_feature
<222> LOCATION: (20)..(21)
<223> OTHER INFORMATION: n is t

<400> SEQUENCE: 32
acuagaagca agaagagacn n                                              21

<210> SEQ ID NO 33
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 33
caccaaaugu cuguaaugan n                                              21

<210> SEQ ID NO 34
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 34
ucauuacaga cauuuggugn n                                              21

<210> SEQ ID NO 35
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 35
cuagguauca gauuccuuun n                                              21

<210> SEQ ID NO 36
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 36
aaaggaaucu gauaccuagn n                                              21

<210> SEQ ID NO 37
<211> LENGTH: 21
<212> TYPE: DNA
<213> ORGANISM: Artificial Sequence
<220> FEATURE:
<223> OTHER INFORMATION: siRNA sense
```

```
<220> FEATURE:
<221> NAME/KEY: misc_feature
<222> LOCATION: (20)..(21)
<223> OTHER INFORMATION: n is t

<400> SEQUENCE: 37
gguaguuagu agagcaugun n                                              21

<210> SEQ ID NO 38
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 38
acaugcucua cuaacuaccn n                                              21

<210> SEQ ID NO 39
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 39
cuccugaaga ggaagagaan n                                              21

<210> SEQ ID NO 40
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 40
uucucuuccu cuucaggagn n                                              21

<210> SEQ ID NO 41
<211> LENGTH: 21
<212> TYPE: DNA
<213> ORGANISM: Artificial Sequence
<220> FEATURE:
<223> OTHER INFORMATION: siRNA  sense
<220> FEATURE:
<221> NAME/KEY: misc_feature
<222> LOCATION: (20)..(21)
<223> OTHER INFORMATION: n is t

<400> SEQUENCE: 41
cggagacaga ucaacuugan n                                              21

<210> SEQ ID NO 42
<211> LENGTH: 21
<212> TYPE: DNA
<213> ORGANISM: Artificial Sequence
<220> FEATURE:
```

<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 42
ucaaguugau cugucuccgn n                                      21

<210> SEQ ID NO 43
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 43
caccucuucc agagauguan n                                      21

<210> SEQ ID NO 44
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 44
uacaucucug gaagaggugn n                                      21

<210> SEQ ID NO 45
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 45
caaggguuga cuucaagaan n                                      21

<210> SEQ ID NO 46
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 46
uucuugaagu caacccuugn n                                      21

<210> SEQ ID NO 47
<211> LENGTH: 21
<212> TYPE: DNA
<213> ORGANISM: Artificial Sequence

```
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 47
gaugcuggau uucaauguan n                                              21

<210> SEQ ID NO 48
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 48
uacauugaaa uccagcaucn n                                              21

<210> SEQ ID NO 49
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 49
ggguauaauu gcaucuacun n                                              21

<210> SEQ ID NO 50
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 50
aguagaugca auuauacccn n                                              21

<210> SEQ ID NO 51
<211> LENGTH: 21
<212> TYPE: DNA
<213> ORGANISM: Artificial Sequence
<220> FEATURE:
<223> OTHER INFORMATION: siRNA  sense
<220> FEATURE:
<221> NAME/KEY: misc_feature
<222> LOCATION: (20)..(21)
<223> OTHER INFORMATION: n is t

<400> SEQUENCE: 51
gcaugugcac aucuaguuun n                                              21

<210> SEQ ID NO 52
<211> LENGTH: 21
<212> TYPE: DNA
```

```
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 52
aaacuagaug ugcacaugcn n                                              21

<210> SEQ ID NO 53
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 53
gugugacagu guaucuucan n                                              21

<210> SEQ ID NO 54
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 54
ugaagauaca cugucacacn n                                              21

<210> SEQ ID NO 55
<211> LENGTH: 21
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 55
cgacaugaga ggugaugaan n                                              21

<210> SEQ ID NO 56
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 56
uucaucaccu cucaugucgn n                                              21

<210> SEQ ID NO 57
<211> LENGTH: 21
```

```
<212> TYPE: DNA
<213> ORGANISM: Artificial Sequence
<220> FEATURE:
<223> OTHER INFORMATION: siRNA sense
<220> FEATURE:
<221> NAME/KEY: misc_feature
<222> LOCATION: (20)..(21)
<223> OTHER INFORMATION: n is t

<400> SEQUENCE: 57
gaaggaaaua gcucagauan n                                              21

<210> SEQ ID NO 58
<211> LENGTH: 21
<212> TYPE: DNA
<213> ORGANISM: Artificial Sequence
<220> FEATURE:
<223> OTHER INFORMATION: siRNA antisense
<220> FEATURE:
<221> NAME/KEY: misc_feature
<222> LOCATION: (20)..(21)
<223> OTHER INFORMATION: n is t

<400> SEQUENCE: 58
uaucugagcu auuccuucn n                                               21

<210> SEQ ID NO 59
<211> LENGTH: 22
<212> TYPE: DNA
<213> ORGANISM: Artificial Sequence
<220> FEATURE:
<223> OTHER INFORMATION: Synthetic primer

<400> SEQUENCE: 59
cccacaagat gatccctaca at                                             22

<210> SEQ ID NO 60
<211> LENGTH: 22
<212> TYPE: DNA
<213> ORGANISM: Artificial Sequence
<220> FEATURE:
<223> OTHER INFORMATION: Synthetic primer

<400> SEQUENCE: 60
cacctgacac agctctacta ac                                             22

<210> SEQ ID NO 61
<211> LENGTH: 20
<212> TYPE: DNA
<213> ORGANISM: Artificial Sequence
<220> FEATURE:
<223> OTHER INFORMATION: Synthetic primer

<400> SEQUENCE: 61
gaagagctgg tgagcatgaa                                                20

<210> SEQ ID NO 62
<211> LENGTH: 21
<212> TYPE: DNA
<213> ORGANISM: Artificial Sequence
<220> FEATURE:
<223> OTHER INFORMATION: Synthetic primer

<400> SEQUENCE: 62
agcctgagcg agttgatatt g                                              21

<210> SEQ ID NO 63
```

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 63
tcctaacacc cagctaccta aa                                              22

<210> SEQ ID NO 64
<211> LENGTH: 22
<212> TYPE: DNA
<213> ORGANISM: Artificial Sequence
<220> FEATURE:
<223> OTHER INFORMATION: Synthetic primer

<400> SEQUENCE: 64
ccatccttcc tggctaacat tc                                              22

<210> SEQ ID NO 65
<211> LENGTH: 22
<212> TYPE: DNA
<213> ORGANISM: Artificial Sequence
<220> FEATURE:
<223> OTHER INFORMATION: Synthetic primer

<400> SEQUENCE: 65
gagacgaact gggactgaat aa                                              22

<210> SEQ ID NO 66
<211> LENGTH: 21
<212> TYPE: DNA
<213> ORGANISM: Artificial Sequence
<220> FEATURE:
<223> OTHER INFORMATION: Synthetic primer

<400> SEQUENCE: 66
gtagccagcc agtggttata g                                               21

<210> SEQ ID NO 67
<211> LENGTH: 20
<212> TYPE: DNA
<213> ORGANISM: Artificial Sequence
<220> FEATURE:
<223> OTHER INFORMATION: Synthetic primer

<400> SEQUENCE: 67
cccaagcagg tcgagtattt                                                 20

<210> SEQ ID NO 68
<211> LENGTH: 21
<212> TYPE: DNA
<213> ORGANISM: Artificial Sequence
<220> FEATURE:
<223> OTHER INFORMATION: Synthetic primer

<400> SEQUENCE: 68
tggaggtagc gacgtaatct a                                               21

<210> SEQ ID NO 69
<211> LENGTH: 22
<212> TYPE: DNA
<213> ORGANISM: Artificial Sequence
<220> FEATURE:
<223> OTHER INFORMATION: Synthetic primer

<400> SEQUENCE: 69
```
atacacagag gaggagagga ag    22

<210> SEQ ID NO 70
<211> LENGTH: 21
<212> TYPE: DNA
<213> ORGANISM: Artificial Sequence
<220> FEATURE:
<223> OTHER INFORMATION: Synthetic primer

<400> SEQUENCE: 70
aagagggaag atgtggttgt g    21

<210> SEQ ID NO 71
<211> LENGTH: 22
<212> TYPE: DNA
<213> ORGANISM: Artificial Sequence
<220> FEATURE:
<223> OTHER INFORMATION: Synthetic primer

<400> SEQUENCE: 71
cctggacaga acatcctcat tc    22

<210> SEQ ID NO 72
<211> LENGTH: 22
<212> TYPE: DNA
<213> ORGANISM: Artificial Sequence
<220> FEATURE:
<223> OTHER INFORMATION: Synthetic primer

<400> SEQUENCE: 72
cccaagactt ctcaggcaat ag    22

<210> SEQ ID NO 73
<211> LENGTH: 20
<212> TYPE: DNA
<213> ORGANISM: Artificial Sequence
<220> FEATURE:
<223> OTHER INFORMATION: Synthetic primer

<400> SEQUENCE: 73
gcaagagaga cgcaaagaga    20

<210> SEQ ID NO 74
<211> LENGTH: 21
<212> TYPE: DNA
<213> ORGANISM: Artificial Sequence
<220> FEATURE:
<223> OTHER INFORMATION: Synthetic primer

<400> SEQUENCE: 74
gaccgacttc tggtggtaaa g    21

<210> SEQ ID NO 75
<211> LENGTH: 22
<212> TYPE: DNA
<213> ORGANISM: Artificial Sequence
<220> FEATURE:
<223> OTHER INFORMATION: Synthetic primer

<400> SEQUENCE: 75
gtcctccgag gttatgatgt tg    22

<210> SEQ ID NO 76
<211> LENGTH: 22
<212> TYPE: DNA

<213> ORGANISM: Artificial Sequence
<220> FEATURE:
<223> OTHER INFORMATION: Synthetic primer

<400> SEQUENCE: 76
ggtgacgaca gtcttgtgat ag          22

<210> SEQ ID NO 77
<211> LENGTH: 21
<212> TYPE: DNA
<213> ORGANISM: Artificial Sequence
<220> FEATURE:
<223> OTHER INFORMATION: Synthetic primer

<400> SEQUENCE: 77
cctgaacaag cctggactaa a          21

<210> SEQ ID NO 78
<211> LENGTH: 21
<212> TYPE: DNA
<213> ORGANISM: Artificial Sequence
<220> FEATURE:
<223> OTHER INFORMATION: Synthetic primer

<400> SEQUENCE: 78
gatgcccttg gattgacagt a          21

<210> SEQ ID NO 79
<211> LENGTH: 20
<212> TYPE: DNA
<213> ORGANISM: Artificial Sequence
<220> FEATURE:
<223> OTHER INFORMATION: Synthetic primer

<400> SEQUENCE: 79
ctgcactacc catccattgt          20

<210> SEQ ID NO 80
<211> LENGTH: 21
<212> TYPE: DNA
<213> ORGANISM: Artificial Sequence
<220> FEATURE:
<223> OTHER INFORMATION: Synthetic primer

<400> SEQUENCE: 80
tttcccacag tcacagcata g          21

<210> SEQ ID NO 81
<211> LENGTH: 21
<212> TYPE: DNA
<213> ORGANISM: Artificial Sequence
<220> FEATURE:
<223> OTHER INFORMATION: Synthetic primer

<400> SEQUENCE: 81
gaagaaggga caccacctaa c          21

<210> SEQ ID NO 82
<211> LENGTH: 20
<212> TYPE: DNA
<213> ORGANISM: Artificial Sequence
<220> FEATURE:
<223> OTHER INFORMATION: Synthetic primer

<400> SEQUENCE: 82
gtcacctgtg gcagtgtatt          20

<210> SEQ ID NO 83
<211> LENGTH: 22
<212> TYPE: DNA
<213> ORGANISM: Artificial Sequence
<220> FEATURE:
<223> OTHER INFORMATION: Synthetic primer

<400> SEQUENCE: 83
ggtcaagccc atctctaact ac                                          22

<210> SEQ ID NO 84
<211> LENGTH: 22
<212> TYPE: DNA
<213> ORGANISM: Artificial Sequence
<220> FEATURE:
<223> OTHER INFORMATION: Synthetic primer

<400> SEQUENCE: 84
ggatgagaaa gaccaggatg ag                                          22

<210> SEQ ID NO 85
<211> LENGTH: 21
<212> TYPE: DNA
<213> ORGANISM: Artificial Sequence
<220> FEATURE:
<223> OTHER INFORMATION: Synthetic primer

<400> SEQUENCE: 85
agctctgcat ggtctgttta g                                           21

<210> SEQ ID NO 86
<211> LENGTH: 22
<212> TYPE: DNA
<213> ORGANISM: Artificial Sequence
<220> FEATURE:
<223> OTHER INFORMATION: Synthetic primer

<400> SEQUENCE: 86
ggcagaaatg tgctgtgtta tc                                          22

<210> SEQ ID NO 87
<211> LENGTH: 20
<212> TYPE: DNA
<213> ORGANISM: Artificial Sequence
<220> FEATURE:
<223> OTHER INFORMATION: Synthetic primer

<400> SEQUENCE: 87
accagccaga tcggtttatg                                             20

<210> SEQ ID NO 88
<211> LENGTH: 21
<212> TYPE: DNA
<213> ORGANISM: Artificial Sequence
<220> FEATURE:
<223> OTHER INFORMATION: Synthetic primer

<400> SEQUENCE: 88
taactgggtg tgggtgtaat g                                           21

<210> SEQ ID NO 89
<211> LENGTH: 22
<212> TYPE: DNA
<213> ORGANISM: Artificial Sequence
<220> FEATURE:

<223> OTHER INFORMATION: Synthetic primer

<400> SEQUENCE: 89
ggccttactg gttgagtcta tc                                              22

<210> SEQ ID NO 90
<211> LENGTH: 22
<212> TYPE: DNA
<213> ORGANISM: Artificial Sequence
<220> FEATURE:
<223> OTHER INFORMATION: Synthetic primer

<400> SEQUENCE: 90
gttgacatcc cggtaggaat aa                                              22

<210> SEQ ID NO 91
<211> LENGTH: 22
<212> TYPE: DNA
<213> ORGANISM: Artificial Sequence
<220> FEATURE:
<223> OTHER INFORMATION: Synthetic primer

<400> SEQUENCE: 91
gccctaactc aagctgtcta tc                                              22

<210> SEQ ID NO 92
<211> LENGTH: 22
<212> TYPE: DNA
<213> ORGANISM: Artificial Sequence
<220> FEATURE:
<223> OTHER INFORMATION: Synthetic primer

<400> SEQUENCE: 92
gattcaggac acttggcttc ta                                              22

<210> SEQ ID NO 93
<211> LENGTH: 22
<212> TYPE: DNA
<213> ORGANISM: Artificial Sequence
<220> FEATURE:
<223> OTHER INFORMATION: Synthetic primer

<400> SEQUENCE: 93
gggactttga ttctggctac tc                                              22

<210> SEQ ID NO 94
<211> LENGTH: 21
<212> TYPE: DNA
<213> ORGANISM: Artificial Sequence
<220> FEATURE:
<223> OTHER INFORMATION: Synthetic primer

<400> SEQUENCE: 94
cagtgggatg caggtgataa t                                               21

<210> SEQ ID NO 95
<211> LENGTH: 21
<212> TYPE: DNA
<213> ORGANISM: Artificial Sequence
<220> FEATURE:
<223> OTHER INFORMATION: Synthetic primer

<400> SEQUENCE: 95
gcatttgcca ggaagagaaa g                                               21

<210> SEQ ID NO 96
<211> LENGTH: 22
<212> TYPE: DNA
<213> ORGANISM: Artificial Sequence
<220> FEATURE:
<223> OTHER INFORMATION: Synthetic primer

<400> SEQUENCE: 96
aactgaagcc ggttagacat ag                                        22

<210> SEQ ID NO 97
<211> LENGTH: 22
<212> TYPE: DNA
<213> ORGANISM: Artificial Sequence
<220> FEATURE:
<223> OTHER INFORMATION: Synthetic primer

<400> SEQUENCE: 97
tgtgaggtct tgggagaaga ta                                        22

<210> SEQ ID NO 98
<211> LENGTH: 22
<212> TYPE: DNA
<213> ORGANISM: Artificial Sequence
<220> FEATURE:
<223> OTHER INFORMATION: Synthetic primer

<400> SEQUENCE: 98
ccacatgtcc aggaggataa tg                                        22

<210> SEQ ID NO 99
<211> LENGTH: 20
<212> TYPE: DNA
<213> ORGANISM: Artificial Sequence
<220> FEATURE:
<223> OTHER INFORMATION: Synthetic primer

<400> SEQUENCE: 99
gctcctagtg ttgctgtgaa                                           20

<210> SEQ ID NO 100
<211> LENGTH: 22
<212> TYPE: DNA
<213> ORGANISM: Artificial Sequence
<220> FEATURE:
<223> OTHER INFORMATION: Synthetic primer

<400> SEQUENCE: 100
ccctgtaagc tgttgtgtat ct                                        22

<210> SEQ ID NO 101
<211> LENGTH: 22
<212> TYPE: DNA
<213> ORGANISM: Artificial Sequence
<220> FEATURE:
<223> OTHER INFORMATION: Synthetic primer

<400> SEQUENCE: 101
gagatggctc agtggttaag ag                                        22

<210> SEQ ID NO 102
<211> LENGTH: 23
<212> TYPE: DNA
<213> ORGANISM: Artificial Sequence
<220> FEATURE:
<223> OTHER INFORMATION: Synthetic primer

```
<400> SEQUENCE: 102
ggatttcatt acggatggtt gtg                                          23

<210> SEQ ID NO 103
<211> LENGTH: 20
<212> TYPE: DNA
<213> ORGANISM: Artificial Sequence
<220> FEATURE:
<223> OTHER INFORMATION: Synthetic primer

<400> SEQUENCE: 103
tttgtaggag cagccatgag                                              20

<210> SEQ ID NO 104
<211> LENGTH: 20
<212> TYPE: DNA
<213> ORGANISM: Artificial Sequence
<220> FEATURE:
<223> OTHER INFORMATION: Synthetic primer

<400> SEQUENCE: 104
ccgaagttgt agccgaagaa                                              20

<210> SEQ ID NO 105
<211> LENGTH: 23
<212> TYPE: DNA
<213> ORGANISM: Artificial Sequence
<220> FEATURE:
<223> OTHER INFORMATION: Synthetic primer

<400> SEQUENCE: 105
gtctgctggc tctctaacta atc                                          23

<210> SEQ ID NO 106
<211> LENGTH: 23
<212> TYPE: DNA
<213> ORGANISM: Artificial Sequence
<220> FEATURE:
<223> OTHER INFORMATION: Synthetic primer

<400> SEQUENCE: 106
gaaatctgct gcacttgata cac                                          23

<210> SEQ ID NO 107
<211> LENGTH: 20
<212> TYPE: DNA
<213> ORGANISM: Artificial Sequence
<220> FEATURE:
<223> OTHER INFORMATION: Synthetic primer

<400> SEQUENCE: 107
ggagaaggcc acagctattt                                              20

<210> SEQ ID NO 108
<211> LENGTH: 22
<212> TYPE: DNA
<213> ORGANISM: Artificial Sequence
<220> FEATURE:
<223> OTHER INFORMATION: Synthetic primer

<400> SEQUENCE: 108
ccacacagag ggagagagat ta                                           22

<210> SEQ ID NO 109
<211> LENGTH: 22
```

<212> TYPE: DNA
<213> ORGANISM: Artificial Sequence
<220> FEATURE:
<223> OTHER INFORMATION: Synthetic primer

<400> SEQUENCE: 109
gacaatcccg aagacactac ag        22

<210> SEQ ID NO 110
<211> LENGTH: 22
<212> TYPE: DNA
<213> ORGANISM: Artificial Sequence
<220> FEATURE:
<223> OTHER INFORMATION: Synthetic primer

<400> SEQUENCE: 110
agagaggaga gagagagaga ga        22

<210> SEQ ID NO 111
<211> LENGTH: 22
<212> TYPE: DNA
<213> ORGANISM: Artificial Sequence
<220> FEATURE:
<223> OTHER INFORMATION: Synthetic primer

<400> SEQUENCE: 111
atcttccctc taccacgtct at        22

<210> SEQ ID NO 112
<211> LENGTH: 22
<212> TYPE: DNA
<213> ORGANISM: Artificial Sequence
<220> FEATURE:
<223> OTHER INFORMATION: Synthetic primer

<400> SEQUENCE: 112
ggtctgcagg ttcttaaggt ag        22

<210> SEQ ID NO 113
<211> LENGTH: 21
<212> TYPE: DNA
<213> ORGANISM: Artificial Sequence
<220> FEATURE:
<223> OTHER INFORMATION: Synthetic primer

<400> SEQUENCE: 113
ttgggctagt ggaagaaagt g        21

<210> SEQ ID NO 114
<211> LENGTH: 20
<212> TYPE: DNA
<213> ORGANISM: Artificial Sequence
<220> FEATURE:
<223> OTHER INFORMATION: Synthetic primer

<400> SEQUENCE: 114
ctgccaagaa acggctagaa        20

<210> SEQ ID NO 115
<211> LENGTH: 22
<212> TYPE: DNA
<213> ORGANISM: Artificial Sequence
<220> FEATURE:
<223> OTHER INFORMATION: Synthetic primer

<400> SEQUENCE: 115
ggatcctggg aagttggatt ag                                              22

<210> SEQ ID NO 116
<211> LENGTH: 24
<212> TYPE: DNA
<213> ORGANISM: Artificial Sequence
<220> FEATURE:
<223> OTHER INFORMATION: Synthetic primer

<400> SEQUENCE: 116
ctagagctgg agggaataga aatg                                            24

<210> SEQ ID NO 117
<211> LENGTH: 20
<212> TYPE: DNA
<213> ORGANISM: Artificial Sequence
<220> FEATURE:
<223> OTHER INFORMATION: Synthetic primer

<400> SEQUENCE: 117
cgagaatcga cagccaagaa                                                 20

<210> SEQ ID NO 118
<211> LENGTH: 23
<212> TYPE: DNA
<213> ORGANISM: Artificial Sequence
<220> FEATURE:
<223> OTHER INFORMATION: Synthetic primer

<400> SEQUENCE: 118
tgatttcagg aacctgggat aag                                             23

<210> SEQ ID NO 119
<211> LENGTH: 20
<212> TYPE: DNA
<213> ORGANISM: Artificial Sequence
<220> FEATURE:
<223> OTHER INFORMATION: Synthetic primer

<400> SEQUENCE: 119
tcgggaaagc agagtttgag                                                 20

<210> SEQ ID NO 120
<211> LENGTH: 22
<212> TYPE: DNA
<213> ORGANISM: Artificial Sequence
<220> FEATURE:
<223> OTHER INFORMATION: Synthetic primer

<400> SEQUENCE: 120
ccaactagct aaggccacat aa                                              22

<210> SEQ ID NO 121
<211> LENGTH: 20
<212> TYPE: DNA
<213> ORGANISM: Artificial Sequence
<220> FEATURE:
<223> OTHER INFORMATION: Synthetic primer

<400> SEQUENCE: 121
ctaggcacaa ggcagaagaa                                                 20

<210> SEQ ID NO 122
<211> LENGTH: 22
<212> TYPE: DNA
<213> ORGANISM: Artificial Sequence

```
<220> FEATURE:
<223> OTHER INFORMATION: Synthetic primer

<400> SEQUENCE: 122
agaacattcc gctctgacat aa                                          22

<210> SEQ ID NO 123
<211> LENGTH: 22
<212> TYPE: DNA
<213> ORGANISM: Artificial Sequence
<220> FEATURE:
<223> OTHER INFORMATION: Synthetic primer

<400> SEQUENCE: 123
aaacctccct tggtcacatt ag                                          22

<210> SEQ ID NO 124
<211> LENGTH: 21
<212> TYPE: DNA
<213> ORGANISM: Artificial Sequence
<220> FEATURE:
<223> OTHER INFORMATION: Synthetic primer

<400> SEQUENCE: 124
tcttccctga cacctctact c                                           21

<210> SEQ ID NO 125
<211> LENGTH: 22
<212> TYPE: DNA
<213> ORGANISM: Artificial Sequence
<220> FEATURE:
<223> OTHER INFORMATION: Synthetic primer

<400> SEQUENCE: 125
ggaccgggag gatttcttta tt                                          22

<210> SEQ ID NO 126
<211> LENGTH: 21
<212> TYPE: DNA
<213> ORGANISM: Artificial Sequence
<220> FEATURE:
<223> OTHER INFORMATION: Synthetic primer

<400> SEQUENCE: 126
cttcagtcct caccctcaaa c                                           21

<210> SEQ ID NO 127
<211> LENGTH: 20
<212> TYPE: DNA
<213> ORGANISM: Artificial Sequence
<220> FEATURE:
<223> OTHER INFORMATION: Synthetic primer

<400> SEQUENCE: 127
ttcacatacc tgcccttgg                                              20

<210> SEQ ID NO 128
<211> LENGTH: 23
<212> TYPE: DNA
<213> ORGANISM: Artificial Sequence
<220> FEATURE:
<223> OTHER INFORMATION: Synthetic primer

<400> SEQUENCE: 128
cttgtgtagg acctggagta ttg                                         23
```

<210> SEQ ID NO 129
<211> LENGTH: 22
<212> TYPE: DNA
<213> ORGANISM: Artificial Sequence
<220> FEATURE:
<223> OTHER INFORMATION: Synthetic primer

<400> SEQUENCE: 129
ccttgagtca ctgggtgtta tg                                              22

<210> SEQ ID NO 130
<211> LENGTH: 22
<212> TYPE: DNA
<213> ORGANISM: Artificial Sequence
<220> FEATURE:
<223> OTHER INFORMATION: Synthetic primer

<400> SEQUENCE: 130
ccacttagct gtcaccctaa tc                                              22

<210> SEQ ID NO 131
<211> LENGTH: 22
<212> TYPE: DNA
<213> ORGANISM: Artificial Sequence
<220> FEATURE:
<223> OTHER INFORMATION: Synthetic primer

<400> SEQUENCE: 131
catcaccagc actctgtatc tc                                              22

<210> SEQ ID NO 132
<211> LENGTH: 20
<212> TYPE: DNA
<213> ORGANISM: Artificial Sequence
<220> FEATURE:
<223> OTHER INFORMATION: Synthetic primer

<400> SEQUENCE: 132
ggttccttcg gttccttcat                                                 20

<210> SEQ ID NO 133
<211> LENGTH: 21
<212> TYPE: DNA
<213> ORGANISM: Artificial Sequence
<220> FEATURE:
<223> OTHER INFORMATION: Synthetic primer

<400> SEQUENCE: 133
gagagggcct tgaaggttat g                                               21

<210> SEQ ID NO 134
<211> LENGTH: 21
<212> TYPE: DNA
<213> ORGANISM: Artificial Sequence
<220> FEATURE:
<223> OTHER INFORMATION: Synthetic primer

<400> SEQUENCE: 134
ctatgtggcc cgttaggatt t                                               21

<210> SEQ ID NO 135
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 135
cgagacctgt tccagatgaa g                                              21

<210> SEQ ID NO 136
<211> LENGTH: 21
<212> TYPE: DNA
<213> ORGANISM: Artificial Sequence
<220> FEATURE:
<223> OTHER INFORMATION: Synthetic primer

<400> SEQUENCE: 136
ttcgctgatg tccctcaata c                                              21

<210> SEQ ID NO 137
<211> LENGTH: 21
<212> TYPE: DNA
<213> ORGANISM: Artificial Sequence
<220> FEATURE:
<223> OTHER INFORMATION: Synthetic primer

<400> SEQUENCE: 137
agaggtggga tgttggttat g                                              21

<210> SEQ ID NO 138
<211> LENGTH: 22
<212> TYPE: DNA
<213> ORGANISM: Artificial Sequence
<220> FEATURE:
<223> OTHER INFORMATION: Synthetic primer

<400> SEQUENCE: 138
ccagtttaac cctctgcatt tg                                             22

<210> SEQ ID NO 139
<211> LENGTH: 21
<212> TYPE: DNA
<213> ORGANISM: Artificial Sequence
<220> FEATURE:
<223> OTHER INFORMATION: Synthetic primer

<400> SEQUENCE: 139
gagcaagtga gcacagatac a                                              21

<210> SEQ ID NO 140
<211> LENGTH: 22
<212> TYPE: DNA
<213> ORGANISM: Artificial Sequence
<220> FEATURE:
<223> OTHER INFORMATION: Synthetic primer

<400> SEQUENCE: 140
gcagaataca cagggaagag ag                                             22

<210> SEQ ID NO 141
<211> LENGTH: 22
<212> TYPE: DNA
<213> ORGANISM: Artificial Sequence
<220> FEATURE:
<223> OTHER INFORMATION: Synthetic primer

<400> SEQUENCE: 141
ctccgaaacc tgtctcactt ac                                             22

<210> SEQ ID NO 142
```

```
<211> LENGTH: 21
<212> TYPE: DNA
<213> ORGANISM: Artificial Sequence
<220> FEATURE:
<223> OTHER INFORMATION: Synthetic primer

<400> SEQUENCE: 142
gttctagctg agggcattct t                                              21

<210> SEQ ID NO 143
<211> LENGTH: 23
<212> TYPE: DNA
<213> ORGANISM: Artificial Sequence
<220> FEATURE:
<223> OTHER INFORMATION: Synthetic primer

<400> SEQUENCE: 143
gacagacaga cagacagaca tac                                            23

<210> SEQ ID NO 144
<211> LENGTH: 23
<212> TYPE: DNA
<213> ORGANISM: Artificial Sequence
<220> FEATURE:
<223> OTHER INFORMATION: Synthetic primer

<400> SEQUENCE: 144
gtctccaacc acttcctctt aat                                            23

<210> SEQ ID NO 145
<211> LENGTH: 21
<212> TYPE: DNA
<213> ORGANISM: Artificial Sequence
<220> FEATURE:
<223> OTHER INFORMATION: Synthetic primer

<400> SEQUENCE: 145
cctggaaagg tctggagaat g                                              21

<210> SEQ ID NO 146
<211> LENGTH: 22
<212> TYPE: DNA
<213> ORGANISM: Artificial Sequence
<220> FEATURE:
<223> OTHER INFORMATION: Synthetic primer

<400> SEQUENCE: 146
ggcagatcag tccttccata aa                                             22

<210> SEQ ID NO 147
<211> LENGTH: 21
<212> TYPE: DNA
<213> ORGANISM: Artificial Sequence
<220> FEATURE:
<223> OTHER INFORMATION: Synthetic primer

<400> SEQUENCE: 147
taagcaccga ggagagtaga a                                              21

<210> SEQ ID NO 148
<211> LENGTH: 21
<212> TYPE: DNA
<213> ORGANISM: Artificial Sequence
<220> FEATURE:
<223> OTHER INFORMATION: Synthetic primer

<400> SEQUENCE: 148
```
gtccaagggt tactcacaac a                                              21

<210> SEQ ID NO 149
<211> LENGTH: 21
<212> TYPE: DNA
<213> ORGANISM: Artificial Sequence
<220> FEATURE:
<223> OTHER INFORMATION: Synthetic primer

<400> SEQUENCE: 149
gcacccagac agaagtcata g                                              21

<210> SEQ ID NO 150
<211> LENGTH: 20
<212> TYPE: DNA
<213> ORGANISM: Artificial Sequence
<220> FEATURE:
<223> OTHER INFORMATION: Synthetic primer

<400> SEQUENCE: 150
acttgccgct cttcagtatc                                                20

<210> SEQ ID NO 151
<211> LENGTH: 20
<212> TYPE: DNA
<213> ORGANISM: Artificial Sequence
<220> FEATURE:
<223> OTHER INFORMATION: Synthetic primer

<400> SEQUENCE: 151
ccagtgtaca gcagcctaaa                                                20

<210> SEQ ID NO 152
<211> LENGTH: 22
<212> TYPE: DNA
<213> ORGANISM: Artificial Sequence
<220> FEATURE:
<223> OTHER INFORMATION: Synthetic primer

<400> SEQUENCE: 152
ctggagcatc ctgcataagt aa                                             22

<210> SEQ ID NO 153
<211> LENGTH: 20
<212> TYPE: DNA
<213> ORGANISM: Artificial Sequence
<220> FEATURE:
<223> OTHER INFORMATION: Synthetic primer

<400> SEQUENCE: 153
gcccaggact gcttcttatt                                                20

<210> SEQ ID NO 154
<211> LENGTH: 21
<212> TYPE: DNA
<213> ORGANISM: Artificial Sequence
<220> FEATURE:
<223> OTHER INFORMATION: Synthetic primer

<400> SEQUENCE: 154
tggcatctgt caccaacttt a                                              21

<210> SEQ ID NO 155
<211> LENGTH: 23
<212> TYPE: DNA

```
<213> ORGANISM: Artificial Sequence
<220> FEATURE:
<223> OTHER INFORMATION: Synthetic primer

<400> SEQUENCE: 155
gtccagttta tcctctgctc ttg                                              23

<210> SEQ ID NO 156
<211> LENGTH: 22
<212> TYPE: DNA
<213> ORGANISM: Artificial Sequence
<220> FEATURE:
<223> OTHER INFORMATION: Synthetic primer

<400> SEQUENCE: 156
cacaggtcac agtcccttat tg                                               22

<210> SEQ ID NO 157
<211> LENGTH: 22
<212> TYPE: DNA
<213> ORGANISM: Artificial Sequence
<220> FEATURE:
<223> OTHER INFORMATION: Synthetic primer

<400> SEQUENCE: 157
gaatccgaag ggaacggaat aa                                               22

<210> SEQ ID NO 158
<211> LENGTH: 20
<212> TYPE: DNA
<213> ORGANISM: Artificial Sequence
<220> FEATURE:
<223> OTHER INFORMATION: Synthetic primer

<400> SEQUENCE: 158
tctccgcttg gagtgtatct                                                  20

<210> SEQ ID NO 159
<211> LENGTH: 20
<212> TYPE: DNA
<213> ORGANISM: Artificial Sequence
<220> FEATURE:
<223> OTHER INFORMATION: Synthetic primer

<400> SEQUENCE: 159
gcctgcttgc tttgtcttac                                                  20

<210> SEQ ID NO 160
<211> LENGTH: 21
<212> TYPE: DNA
<213> ORGANISM: Artificial Sequence
<220> FEATURE:
<223> OTHER INFORMATION: Synthetic primer

<400> SEQUENCE: 160
gaggtcacac ccagagttta g                                                21

<210> SEQ ID NO 161
<211> LENGTH: 22
<212> TYPE: DNA
<213> ORGANISM: Artificial Sequence
<220> FEATURE:
<223> OTHER INFORMATION: Synthetic primer

<400> SEQUENCE: 161
ccttatctgg cttccacatc tc                                               22
```

<210> SEQ ID NO 162
<211> LENGTH: 20
<212> TYPE: DNA
<213> ORGANISM: Artificial Sequence
<220> FEATURE:
<223> OTHER INFORMATION: Synthetic primer

<400> SEQUENCE: 162
gttcaacgaa cggccaaatc                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic primer

<400> SEQUENCE: 163
gcaggatcta gcagcagaaa                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic primer

<400> SEQUENCE: 164
catgatgccc agcacataga                                               20

<210> SEQ ID NO 165
<211> LENGTH: 22
<212> TYPE: DNA
<213> ORGANISM: Artificial Sequence
<220> FEATURE:
<223> OTHER INFORMATION: Synthetic primer

<400> SEQUENCE: 165
gctgctgaag ccattcattt ag                                            22

<210> SEQ ID NO 166
<211> LENGTH: 22
<212> TYPE: DNA
<213> ORGANISM: Artificial Sequence
<220> FEATURE:
<223> OTHER INFORMATION: Synthetic primer

<400> SEQUENCE: 166
cgtgggaaga ggtgaagata ag                                            22

<210> SEQ ID NO 167
<211> LENGTH: 20
<212> TYPE: DNA
<213> ORGANISM: Artificial Sequence
<220> FEATURE:
<223> OTHER INFORMATION: Synthetic primer

<400> SEQUENCE: 167
gggatcacct gtggcttatt                                               20

<210> SEQ ID NO 168
<211> LENGTH: 21
<212> TYPE: DNA
<213> ORGANISM: Artificial Sequence
<220> FEATURE:

<223> OTHER INFORMATION: Synthetic primer

<400> SEQUENCE: 168
gatctcagtt ccctgctctt c                                              21

<210> SEQ ID NO 169
<211> LENGTH: 22
<212> TYPE: DNA
<213> ORGANISM: Artificial Sequence
<220> FEATURE:
<223> OTHER INFORMATION: Synthetic primer

<400> SEQUENCE: 169
atgggcaacc acttacctat tt                                             22

<210> SEQ ID NO 170
<211> LENGTH: 23
<212> TYPE: DNA
<213> ORGANISM: Artificial Sequence
<220> FEATURE:
<223> OTHER INFORMATION: Synthetic primer

<400> SEQUENCE: 170
gttctagaga gtgctgccta atg                                            23

<210> SEQ ID NO 171
<211> LENGTH: 20
<212> TYPE: DNA
<213> ORGANISM: Artificial Sequence
<220> FEATURE:
<223> OTHER INFORMATION: Synthetic primer

<400> SEQUENCE: 171
ctgatagtcc cgtgcaaagt                                                20

<210> SEQ ID NO 172
<211> LENGTH: 20
<212> TYPE: DNA
<213> ORGANISM: Artificial Sequence
<220> FEATURE:
<223> OTHER INFORMATION: Synthetic primer

<400> SEQUENCE: 172
gggtaagcag ccgagataaa                                                20

<210> SEQ ID NO 173
<211> LENGTH: 22
<212> TYPE: DNA
<213> ORGANISM: Artificial Sequence
<220> FEATURE:
<223> OTHER INFORMATION: Synthetic primer

<400> SEQUENCE: 173
cctactccct cagctttctt tc                                             22

<210> SEQ ID NO 174
<211> LENGTH: 22
<212> TYPE: DNA
<213> ORGANISM: Artificial Sequence
<220> FEATURE:
<223> OTHER INFORMATION: Synthetic primer

<400> SEQUENCE: 174
gcagggtaaa gacagtggaa ta                                             22

<210> SEQ ID NO 175
<211> LENGTH: 22
<212> TYPE: DNA
<213> ORGANISM: Artificial Sequence
<220> FEATURE:
<223> OTHER INFORMATION: Synthetic primer

<400> SEQUENCE: 175
gtctgtagct cattctgctc tg                                              22

<210> SEQ ID NO 176
<211> LENGTH: 20
<212> TYPE: DNA
<213> ORGANISM: Artificial Sequence
<220> FEATURE:
<223> OTHER INFORMATION: Synthetic primer

<400> SEQUENCE: 176
gaaggcaact ggatggaagt                                                 20

<210> SEQ ID NO 177
<211> LENGTH: 22
<212> TYPE: DNA
<213> ORGANISM: Artificial Sequence
<220> FEATURE:
<223> OTHER INFORMATION: Synthetic primer

<400> SEQUENCE: 177
gcgtatgtca ccatgtctag tt                                              22

<210> SEQ ID NO 178
<211> LENGTH: 22
<212> TYPE: DNA
<213> ORGANISM: Artificial Sequence
<220> FEATURE:
<223> OTHER INFORMATION: Synthetic primer

<400> SEQUENCE: 178
agcattccag actttccatc tc                                              22

<210> SEQ ID NO 179
<211> LENGTH: 21
<212> TYPE: DNA
<213> ORGANISM: Artificial Sequence
<220> FEATURE:
<223> OTHER INFORMATION: Synthetic primer

<400> SEQUENCE: 179
cagtgaggtg catagcgtaa t                                               21

<210> SEQ ID NO 180
<211> LENGTH: 22
<212> TYPE: DNA
<213> ORGANISM: Artificial Sequence
<220> FEATURE:
<223> OTHER INFORMATION: Synthetic primer

<400> SEQUENCE: 180
ctccttctgg gacattgcta tc                                              22

<210> SEQ ID NO 181
<211> LENGTH: 23
<212> TYPE: DNA
<213> ORGANISM: Artificial Sequence
<220> FEATURE:
<223> OTHER INFORMATION: Synthetic primer

```
<400> SEQUENCE: 181
cagagctaca gttaccactc ttc                                          23

<210> SEQ ID NO 182
<211> LENGTH: 20
<212> TYPE: DNA
<213> ORGANISM: Artificial Sequence
<220> FEATURE:
<223> OTHER INFORMATION: Synthetic primer

<400> SEQUENCE: 182
tggtgaggtc catgctaaac                                              20

<210> SEQ ID NO 183
<211> LENGTH: 21
<212> TYPE: DNA
<213> ORGANISM: Artificial Sequence
<220> FEATURE:
<223> OTHER INFORMATION: Synthetic primer

<400> SEQUENCE: 183
ctcagtgtcg ggatggttaa g                                            21

<210> SEQ ID NO 184
<211> LENGTH: 20
<212> TYPE: DNA
<213> ORGANISM: Artificial Sequence
<220> FEATURE:
<223> OTHER INFORMATION: Synthetic primer

<400> SEQUENCE: 184
cctgttgtag tgggctcttt                                              20

<210> SEQ ID NO 185
<211> LENGTH: 22
<212> TYPE: DNA
<213> ORGANISM: Artificial Sequence
<220> FEATURE:
<223> OTHER INFORMATION: Synthetic primer

<400> SEQUENCE: 185
gcctcccttc tctttcctaa tc                                           22

<210> SEQ ID NO 186
<211> LENGTH: 21
<212> TYPE: DNA
<213> ORGANISM: Artificial Sequence
<220> FEATURE:
<223> OTHER INFORMATION: Synthetic primer

<400> SEQUENCE: 186
ggcagaaact tcgtcaacat c                                            21

<210> SEQ ID NO 187
<211> LENGTH: 22
<212> TYPE: DNA
<213> ORGANISM: Artificial Sequence
<220> FEATURE:
<223> OTHER INFORMATION: Synthetic primer

<400> SEQUENCE: 187
gagcgaggat gatcgagtat tt                                           22

<210> SEQ ID NO 188
<211> LENGTH: 22
```

```
<212> TYPE: DNA
<213> ORGANISM: Artificial Sequence
<220> FEATURE:
<223> OTHER INFORMATION: Synthetic primer

<400> SEQUENCE: 188
cgggctcata ttcataccag ag                                              22

<210> SEQ ID NO 189
<211> LENGTH: 22
<212> TYPE: DNA
<213> ORGANISM: Artificial Sequence
<220> FEATURE:
<223> OTHER INFORMATION: Synthetic primer

<400> SEQUENCE: 189
gctgtgaagg ctaagggata ag                                              22

<210> SEQ ID NO 190
<211> LENGTH: 22
<212> TYPE: DNA
<213> ORGANISM: Artificial Sequence
<220> FEATURE:
<223> OTHER INFORMATION: Synthetic primer

<400> SEQUENCE: 190
gtgacatttg gagctggtaa ga                                              22

<210> SEQ ID NO 191
<211> LENGTH: 21
<212> TYPE: DNA
<213> ORGANISM: Artificial Sequence
<220> FEATURE:
<223> OTHER INFORMATION: Synthetic primer

<400> SEQUENCE: 191
gccatccagc ttacatcttc t                                               21

<210> SEQ ID NO 192
<211> LENGTH: 22
<212> TYPE: DNA
<213> ORGANISM: Artificial Sequence
<220> FEATURE:
<223> OTHER INFORMATION: Synthetic primer

<400> SEQUENCE: 192
tttgacccag gtagagtgtt tc                                              22

<210> SEQ ID NO 193
<211> LENGTH: 20
<212> TYPE: DNA
<213> ORGANISM: Artificial Sequence
<220> FEATURE:
<223> OTHER INFORMATION: Synthetic primer

<400> SEQUENCE: 193
tggcctcgaa ctcagaaatc                                                 20

<210> SEQ ID NO 194
<211> LENGTH: 22
<212> TYPE: DNA
<213> ORGANISM: Artificial Sequence
<220> FEATURE:
<223> OTHER INFORMATION: Synthetic primer

<400> SEQUENCE: 194
```
cgaggtccaa gagctacaaa ta                                                      22

<210> SEQ ID NO 195
<211> LENGTH: 23
<212> TYPE: DNA
<213> ORGANISM: Artificial Sequence
<220> FEATURE:
<223> OTHER INFORMATION: Synthetic primer

<400> SEQUENCE: 195
gtccagttta tcctctgctc ttg                                                     23

<210> SEQ ID NO 196
<211> LENGTH: 22
<212> TYPE: DNA
<213> ORGANISM: Artificial Sequence
<220> FEATURE:
<223> OTHER INFORMATION: Synthetic primer

<400> SEQUENCE: 196
cacaggtcac agtcccttat tg                                                      22

<210> SEQ ID NO 197
<211> LENGTH: 22
<212> TYPE: DNA
<213> ORGANISM: Artificial Sequence
<220> FEATURE:
<223> OTHER INFORMATION: Synthetic primer

<400> SEQUENCE: 197
tggttcttca ctccctcaaa tc                                                      22

<210> SEQ ID NO 198
<211> LENGTH: 22
<212> TYPE: DNA
<213> ORGANISM: Artificial Sequence
<220> FEATURE:
<223> OTHER INFORMATION: Synthetic primer

<400> SEQUENCE: 198
ggtctctctc tctcttcctt ga                                                      22

<210> SEQ ID NO 199
<211> LENGTH: 22
<212> TYPE: DNA
<213> ORGANISM: Artificial Sequence
<220> FEATURE:
<223> OTHER INFORMATION: Synthetic primer

<400> SEQUENCE: 199
catcagggtg ttgggaagat ag                                                      22

<210> SEQ ID NO 200
<211> LENGTH: 23
<212> TYPE: DNA
<213> ORGANISM: Artificial Sequence
<220> FEATURE:
<223> OTHER INFORMATION: Synthetic primer

<400> SEQUENCE: 200
cattgtcctc aggcttacat ttg                                                     23

<210> SEQ ID NO 201
<211> LENGTH: 20
<212> TYPE: DNA
<213> ORGANISM: Artificial Sequence -continued
<220> FEATURE:
<223> OTHER INFORMATION: Synthetic primer

<400> SEQUENCE: 201
gcccaggact gcttcttatt                                                  20

<210> SEQ ID NO 202
<211> LENGTH: 21
<212> TYPE: DNA
<213> ORGANISM: Artificial Sequence
<220> FEATURE:
<223> OTHER INFORMATION: Synthetic primer

<400> SEQUENCE: 202
tggcatctgt caccaacttt a                                                21

<210> SEQ ID NO 203
<211> LENGTH: 22
<212> TYPE: DNA
<213> ORGANISM: Artificial Sequence
<220> FEATURE:
<223> OTHER INFORMATION: Synthetic primer

<400> SEQUENCE: 203
ctgtcagtct atcccagctc ta                                               22

<210> SEQ ID NO 204
<211> LENGTH: 22
<212> TYPE: DNA
<213> ORGANISM: Artificial Sequence
<220> FEATURE:
<223> OTHER INFORMATION: Synthetic primer

<400> SEQUENCE: 204
ccatgctttc cttcctgtat ca                                               22

<210> SEQ ID NO 205
<211> LENGTH: 22
<212> TYPE: DNA
<213> ORGANISM: Artificial Sequence
<220> FEATURE:
<223> OTHER INFORMATION: Synthetic primer

<400> SEQUENCE: 205
ggatacgggc cacagttaat ag                                               22

<210> SEQ ID NO 206
<211> LENGTH: 21
<212> TYPE: DNA
<213> ORGANISM: Artificial Sequence
<220> FEATURE:
<223> OTHER INFORMATION: Synthetic primer

<400> SEQUENCE: 206
gtagaaggtc acggtgaatg g                                                21

<210> SEQ ID NO 207
<211> LENGTH: 22
<212> TYPE: DNA
<213> ORGANISM: Artificial Sequence
<220> FEATURE:
<223> OTHER INFORMATION: Synthetic primer

<400> SEQUENCE: 207
gacatcttgg ctccctatct tc                                               22

<210> SEQ ID NO 208
<211> LENGTH: 22
<212> TYPE: DNA
<213> ORGANISM: Artificial Sequence
<220> FEATURE:
<223> OTHER INFORMATION: Synthetic primer

<400> SEQUENCE: 208
tggacaatac accagtcagt tt                                              22

<210> SEQ ID NO 209
<211> LENGTH: 21
<212> TYPE: DNA
<213> ORGANISM: Artificial Sequence
<220> FEATURE:
<223> OTHER INFORMATION: Synthetic primer

<400> SEQUENCE: 209
ccgacaaaca gttcctcatc t                                               21

<210> SEQ ID NO 210
<211> LENGTH: 22
<212> TYPE: DNA
<213> ORGANISM: Artificial Sequence
<220> FEATURE:
<223> OTHER INFORMATION: Synthetic primer

<400> SEQUENCE: 210
ccagcttgga gatggcatat aa                                              22

<210> SEQ ID NO 211
<211> LENGTH: 22
<212> TYPE: DNA
<213> ORGANISM: Artificial Sequence
<220> FEATURE:
<223> OTHER INFORMATION: Synthetic primer

<400> SEQUENCE: 211
ctgggtccta tttgctctgt aa                                              22

<210> SEQ ID NO 212
<211> LENGTH: 22
<212> TYPE: DNA
<213> ORGANISM: Artificial Sequence
<220> FEATURE:
<223> OTHER INFORMATION: Synthetic primer

<400> SEQUENCE: 212
ctctgaccat acacaaccta cc                                              22

<210> SEQ ID NO 213
<211> LENGTH: 22
<212> TYPE: DNA
<213> ORGANISM: Artificial Sequence
<220> FEATURE:
<223> OTHER INFORMATION: Synthetic primer

<400> SEQUENCE: 213
ctgaagacct gatcaccaga tg                                              22

<210> SEQ ID NO 214
<211> LENGTH: 22
<212> TYPE: DNA
<213> ORGANISM: Artificial Sequence
<220> FEATURE:
<223> OTHER INFORMATION: Synthetic primer

```
<400> SEQUENCE: 214
gtgcaaggag agaggattta ag                                        22

<210> SEQ ID NO 215
<211> LENGTH: 22
<212> TYPE: DNA
<213> ORGANISM: Artificial Sequence
<220> FEATURE:
<223> OTHER INFORMATION: Synthetic primer

<400> SEQUENCE: 215
ccctctggaa accaggaata ag                                        22

<210> SEQ ID NO 216
<211> LENGTH: 22
<212> TYPE: DNA
<213> ORGANISM: Artificial Sequence
<220> FEATURE:
<223> OTHER INFORMATION: Synthetic primer

<400> SEQUENCE: 216
ccagcagcac tctcatagta ac                                        22

<210> SEQ ID NO 217
<211> LENGTH: 22
<212> TYPE: DNA
<213> ORGANISM: Artificial Sequence
<220> FEATURE:
<223> OTHER INFORMATION: Synthetic primer

<400> SEQUENCE: 217
ctgggtatga agcctatgag tg                                        22

<210> SEQ ID NO 218
<211> LENGTH: 20
<212> TYPE: DNA
<213> ORGANISM: Artificial Sequence
<220> FEATURE:
<223> OTHER INFORMATION: Synthetic primer

<400> SEQUENCE: 218
gtggaccaag gcctgaataa                                           20

<210> SEQ ID NO 219
<211> LENGTH: 21
<212> TYPE: DNA
<213> ORGANISM: Artificial Sequence
<220> FEATURE:
<223> OTHER INFORMATION: Synthetic primer

<400> SEQUENCE: 219
ctgtaaggcc catcggaaat a                                         21

<210> SEQ ID NO 220
<211> LENGTH: 21
<212> TYPE: DNA
<213> ORGANISM: Artificial Sequence
<220> FEATURE:
<223> OTHER INFORMATION: Synthetic primer

<400> SEQUENCE: 220
actgaaggga ttgagcttct g                                         21

<210> SEQ ID NO 221
```

```
<211> LENGTH: 22
<212> TYPE: DNA
<213> ORGANISM: Artificial Sequence
<220> FEATURE:
<223> OTHER INFORMATION: Synthetic primer

<400> SEQUENCE: 221
caaatgctgt gcaggtgata aa                                              22

<210> SEQ ID NO 222
<211> LENGTH: 20
<212> TYPE: DNA
<213> ORGANISM: Artificial Sequence
<220> FEATURE:
<223> OTHER INFORMATION: Synthetic primer

<400> SEQUENCE: 222
cctgagccag ccatttctta                                                 20

<210> SEQ ID NO 223
<211> LENGTH: 23
<212> TYPE: DNA
<213> ORGANISM: Artificial Sequence
<220> FEATURE:
<223> OTHER INFORMATION: Synthetic primer

<400> SEQUENCE: 223
accacctttg aagtgatcct att                                             23

<210> SEQ ID NO 224
<211> LENGTH: 23
<212> TYPE: DNA
<213> ORGANISM: Artificial Sequence
<220> FEATURE:
<223> OTHER INFORMATION: Synthetic primer

<400> SEQUENCE: 224
gcaagtttgt gctccaagat aag                                             23

<210> SEQ ID NO 225
<211> LENGTH: 21
<212> TYPE: DNA
<213> ORGANISM: Artificial Sequence
<220> FEATURE:
<223> OTHER INFORMATION: Synthetic primer

<400> SEQUENCE: 225
catgggagct ggtccttatt t                                               21

<210> SEQ ID NO 226
<211> LENGTH: 21
<212> TYPE: DNA
<213> ORGANISM: Artificial Sequence
<220> FEATURE:
<223> OTHER INFORMATION: Synthetic primer

<400> SEQUENCE: 226
cttgcggtca agtcattgtt g                                               21

<210> SEQ ID NO 227
<211> LENGTH: 20
<212> TYPE: DNA
<213> ORGANISM: Artificial Sequence
<220> FEATURE:
<223> OTHER INFORMATION: Synthetic primer

<400> SEQUENCE: 227
```
ggtcacagtc cgaagaaaca                                                     20

<210> SEQ ID NO 228
<211> LENGTH: 21
<212> TYPE: DNA
<213> ORGANISM: Artificial Sequence
<220> FEATURE:
<223> OTHER INFORMATION: Synthetic primer

<400> SEQUENCE: 228
ctgagttagc gttgccttag a                                                   21

<210> SEQ ID NO 229
<211> LENGTH: 22
<212> TYPE: DNA
<213> ORGANISM: Artificial Sequence
<220> FEATURE:
<223> OTHER INFORMATION: Synthetic primer

<400> SEQUENCE: 229
gggacgaaac tggagatgtt at                                                  22

<210> SEQ ID NO 230
<211> LENGTH: 22
<212> TYPE: DNA
<213> ORGANISM: Artificial Sequence
<220> FEATURE:
<223> OTHER INFORMATION: Synthetic primer

<400> SEQUENCE: 230
gaggagttgc cttctctttc tc                                                  22

<210> SEQ ID NO 231
<211> LENGTH: 22
<212> TYPE: DNA
<213> ORGANISM: Artificial Sequence
<220> FEATURE:
<223> OTHER INFORMATION: Synthetic primer

<400> SEQUENCE: 231
cggactggat tctatggtga aa                                                  22

<210> SEQ ID NO 232
<211> LENGTH: 22
<212> TYPE: DNA
<213> ORGANISM: Artificial Sequence
<220> FEATURE:
<223> OTHER INFORMATION: Synthetic primer

<400> SEQUENCE: 232
cttgaagtgg gtcaggatgt ag                                                  22

<210> SEQ ID NO 233
<211> LENGTH: 21
<212> TYPE: DNA
<213> ORGANISM: Artificial Sequence
<220> FEATURE:
<223> OTHER INFORMATION: Synthetic primer

<400> SEQUENCE: 233
catagaggag actggtggag a                                                   21

<210> SEQ ID NO 234
<211> LENGTH: 21
<212> TYPE: DNA

<213> ORGANISM: Artificial Sequence
<220> FEATURE:
<223> OTHER INFORMATION: Synthetic primer

<400> SEQUENCE: 234
aggctgactc cagaatgaat g                                              21

<210> SEQ ID NO 235
<211> LENGTH: 20
<212> TYPE: DNA
<213> ORGANISM: Artificial Sequence
<220> FEATURE:
<223> OTHER INFORMATION: Synthetic primer

<400> SEQUENCE: 235
aacagcaact cccactcttc                                                20

<210> SEQ ID NO 236
<211> LENGTH: 20
<212> TYPE: DNA
<213> ORGANISM: Artificial Sequence
<220> FEATURE:
<223> OTHER INFORMATION: Synthetic primer

<400> SEQUENCE: 236
cctgttgctg tagccgtatt                                                20

<210> SEQ ID NO 237
<211> LENGTH: 26
<212> TYPE: DNA
<213> ORGANISM: Artificial Sequence
<220> FEATURE:
<223> OTHER INFORMATION: Synthetic primer

<400> SEQUENCE: 237
tgaaggtcgg tgtgaacgga tttggc                                         26

<210> SEQ ID NO 238
<211> LENGTH: 26
<212> TYPE: DNA
<213> ORGANISM: Artificial Sequence
<220> FEATURE:
<223> OTHER INFORMATION: Synthetic primer

<400> SEQUENCE: 238
tagtggggtc tcgctcctgg aagatg                                         26

<210> SEQ ID NO 239
<211> LENGTH: 21
<212> TYPE: DNA
<213> ORGANISM: Artificial Sequence
<220> FEATURE:
<223> OTHER INFORMATION: Synthetic primer

<400> SEQUENCE: 239
ctgacagaga gatttgtgag c                                              21

<210> SEQ ID NO 240
<211> LENGTH: 18
<212> TYPE: DNA
<213> ORGANISM: Artificial Sequence

```
<220> FEATURE:
<223> OTHER INFORMATION: Synthetic primer

<400> SEQUENCE: 240
gcaattcttt ccagctga                                                    18
```